(12) United States Patent
Komatsu et al.

(10) Patent No.: US 7,919,260 B2
(45) Date of Patent: Apr. 5, 2011

(54) SCREENING METHODS USING GPR52

(75) Inventors: Hidetoshi Komatsu, Osaka (JP); Yasuaki Itoh, Tokyo (JP); Masaaki Mori, Osaka (JP); Minoru Maruyama, Osaka (JP)

(73) Assignee: Takeda Pharmaceutical Company Limited, Tsukuba-Shi (JP)

( * ) Notice: Subject to any disclaimer, the term of this patent is extended or adjusted under 35 U.S.C. 154(b) by 418 days.

(21) Appl. No.: 11/886,513

(22) PCT Filed: Mar. 17, 2006

(86) PCT No.: PCT/JP2006/305900
§ 371 (c)(1),
(2), (4) Date: Sep. 17, 2007

(87) PCT Pub. No.: WO2006/098520
PCT Pub. Date: Sep. 21, 2006

(65) Prior Publication Data
US 2009/0069228 A1    Mar. 12, 2009

(30) Foreign Application Priority Data

Mar. 18, 2005 (JP) ................................. 2005-079963
Nov. 17, 2005 (JP) ................................. 2005-332976

(51) Int. Cl.
*G01N 33/53* (2006.01)
*G01N 33/00* (2006.01)

(52) U.S. Cl. .......................................... 435/7.1; 436/86

(58) Field of Classification Search .................. None
See application file for complete search history.

(56) References Cited

U.S. PATENT DOCUMENTS 7,241,579 B2 *  7/2007  Andrews et al. ................ 435/7.1
7,303,889 B2 * 12/2007  Le Poul et al. ................ 435/7.21
7,354,726 B2 *  4/2008  Hinuma et al. ................ 435/7.21

FOREIGN PATENT DOCUMENTS

EP          1 477 806 A1      11/2004
WO        WO-2004/040000      5/2004
WO        WO-2005/095990     10/2005

OTHER PUBLICATIONS

M. Sawzdargo, et al., "Identification and cloning of three novel human G protein-coupled receptor genes GPR52, GPR53 and GPR55: GPR55 is extensively expressed in human brain" Molecular Brain Research, vol. 64, 1999, pp. 193-198.

D. Koike, et al., "Analysis of G protein-coupled receptors: Ligand searches through high-throughput screening", Igaku-no-Ayumi, vol. 212, No. 1, 2005, pp. 29-34, English Abstract.

F. Nara, "G-protein coupled receptor (GPCR)- Targeted recent drug discovery", Igaku-no-Ayumi, vol. 212, No. 1, 2005, pp. 35-40, English Abstract.

C. Melchiorre, et al., "Antimuscarinic action of methoctramine, a new cardioselective M-2 muscarinic receptor antagonist, alone and in combination with atropine and gallamine", European Journal of Pharmacology, vol. 144, 1987, pp. 117-124.

V. Petkov, et al., "Plants with Hypotensive, Antiatheromatous and Coronarodilatating Action", American Journal of Chinese Medicine, vol. VII, No. 3, pp. 197-236.

Supplementary European Search Report for corresponding EP 06 72 9848.

* cited by examiner

*Primary Examiner* — Robert Landsman
(74) *Attorney, Agent, or Firm* — Edwards Angell Palmer & Dodge LLP; David G. Conlin; Lisa Swiszcz

(57) ABSTRACT

Disclosed are compounds or their salts that promote or inhibit the activities of a protein comprising the same or substantially the same as the amino acid sequence represented by SEQ ID NO: 1, compounds or their salts that promote or inhibit the activities of a gene for the protein, antisense polynucleotides comprising the whole or part of a base sequence complimentary or substantially complimentary to the base sequence of a polynucleotide encoding the protein or its partial peptide, antibodies to the protein, etc. These compounds or their salts, antisense nucleotides, antibodies, etc. can be used as agents for the prevention/treatment of mental disorders, prolactin-related disorders, etc.

21 Claims, 3 Drawing Sheets

SEQUENCE LISTING

```
<160> NUMBER OF SEQ ID NOS: 17

<210> SEQ ID NO 1
<211> LENGTH: 361
<212> TYPE: PRT
<213> ORGANISM: Homo sapiens

<400> SEQUENCE: 1

Met Asn Glu Ser Arg Trp Thr Glu Trp Arg Ile Leu Asn Met Ser Ser
1               5                   10                  15

Gly Ile Val Asn Val Ser Glu Arg His Ser Cys Pro Leu Gly Phe Gly
            20                  25                  30

His Tyr Ser Val Val Asp Val Cys Ile Phe Glu Thr Val Val Ile Val
        35                  40                  45

Leu Leu Thr Phe Leu Ile Ile Ala Gly Asn Leu Thr Val Ile Phe Val
    50                  55                  60

Phe His Cys Ala Pro Leu Leu His His Tyr Thr Thr Ser Tyr Phe Ile
65                  70                  75                  80

Gln Thr Met Ala Tyr Ala Asp Leu Phe Val Gly Val Ser Cys Leu Val
                85                  90                  95

Pro Thr Leu Ser Leu Leu His Tyr Ser Thr Gly Val His Glu Ser Leu
            100                 105                 110

Thr Cys Gln Val Phe Gly Tyr Ile Ile Ser Val Leu Lys Ser Val Ser
        115                 120                 125

Met Ala Cys Leu Ala Cys Ile Ser Val Asp Arg Tyr Leu Ala Ile Thr
    130                 135                 140

Lys Pro Leu Ser Tyr Asn Gln Leu Val Thr Pro Cys Arg Leu Arg Ile
145                 150                 155                 160

Cys Ile Ile Leu Ile Trp Ile Tyr Ser Cys Leu Ile Phe Leu Pro Ser
                165                 170                 175

Phe Phe Gly Trp Gly Lys Pro Gly Tyr His Gly Asp Ile Phe Glu Trp
            180                 185                 190

Cys Ala Thr Ser Trp Leu Thr Ser Ala Tyr Phe Thr Gly Phe Ile Val
        195                 200                 205

Cys Leu Leu Tyr Ala Pro Ala Ala Phe Val Val Cys Phe Thr Tyr Phe
    210                 215                 220
```

```
His Ile Phe Lys Ile Cys Arg Gln His Thr Lys Glu Ile Asn Asp Arg
225                 230                 235                 240

Arg Ala Arg Phe Pro Ser His Glu Val Asp Ser Ser Arg Glu Thr Gly
            245                 250                 255

His Ser Pro Asp Arg Arg Tyr Ala Met Val Leu Phe Arg Ile Thr Ser
        260                 265                 270

Val Phe Tyr Met Leu Trp Leu Pro Tyr Ile Ile Tyr Phe Leu Leu Glu
    275                 280                 285

Ser Ser Arg Val Leu Asp Asn Pro Thr Leu Ser Phe Leu Thr Thr Trp
290                 295                 300

Leu Ala Ile Ser Asn Ser Phe Cys Asn Cys Val Ile Tyr Ser Leu Ser
305                 310                 315                 320

Asn Ser Val Phe Arg Leu Gly Leu Arg Arg Leu Ser Glu Thr Met Cys
                325                 330                 335

Thr Ser Cys Met Cys Val Lys Asp Gln Glu Ala Gln Glu Pro Lys Pro
            340                 345                 350

Arg Lys Arg Ala Asn Ser Cys Ser Ile
        355                 360

<210> SEQ ID NO 2
<211> LENGTH: 1083
<212> TYPE: DNA
<213> ORGANISM: Homo sapiens

<400> SEQUENCE: 2
atgaatgaat ccaggtggac tgaatggagg atcctgaaca tgagcagtgg cattgtgaat      60
gtgtccgagc gtcactcctg cccacttgga tttggccact acagtgtggt ggatgtctgc    120
atcttcgaga cagtggttat tgtgttgctg acatttctga tcattgctgg aatctaaca    180
gttatctttg tctttcattg tgctccactg ttacatcatt atactaccag ctatttcatt    240
cagacgatgg catatgctga tcttttcgtt ggagttagct gcttggttcc tactctgtca    300
cttctccact actccacagg tgtccacgag tcattgactt gccaggtttt tggatatatc    360
atctcagttc taaaaagtgt ttctatggca tgtcttgctt gcatcagtgt ggatcgttat    420
cttgcaataa ccaagcctct ttcctacaat caactggtca ccccttgtcg cttgagaatt    480
tgcattattt tgatctggat ctactcctgc taatttttct tgccttcctt ttttggctgg    540
gggaaacctg gttaccatgg tgacattttt gaatggtgtg ccacgtcttg gctcaccagt    600
gcctatttta ctggctttat tgtttgttta ctttatgctc ctgctgcctt tgttgtctgc    660
ttcacttact ccacattttt caaaatttgc cgtcagcaca ccaaagagat aaatgaccga    720
agagcccgat tccctagtca tgaggtagat tcttccagag agactggaca cagccctgac    780
cgtcgctacg ccatggtttt gtttaggata accagtgtat tttatatgct gtggctcccc    840
tatataattt actttcttct agaaagctcc cgggtcttgg acaatccaac tctgtccttc    900
ttaacaacct ggcttgcaat aagtaatagt ttttgtaact gtgtaatata cagcctctcc    960
aacagcgttt tccggctagg cctccgaaga ctgtctgaga caatgtgcac atcctgtatg   1020
tgtgtgaagg atcaggaagc acaagaaccc aaacctagga acgggctaa ttcttgctcc   1080
att                                                                  1083

<210> SEQ ID NO 3
<211> LENGTH: 361
<212> TYPE: PRT
<213> ORGANISM: Norvegicus rattus
```

<400> SEQUENCE: 3

| | | | | | | | | | | | | | | |
|---|---|---|---|---|---|---|---|---|---|---|---|---|---|---|
| Met | Asn | Glu | Ser | Arg | Trp | Thr | Glu | Trp | Arg | Ile | Leu | Asn | Val | Ser | Ser |
| 1 | | | | 5 | | | | | 10 | | | | | 15 | |
| Ser | Ile | Val | Asn | Val | Ser | Glu | His | His | Ser | Cys | Pro | Leu | Gly | Phe | Gly |
| | | | 20 | | | | | 25 | | | | | 30 | | |
| His | Tyr | Ser | Val | Glu | Asp | Val | Cys | Ile | Phe | Glu | Thr | Val | Val | Ile | Val |
| | | 35 | | | | | 40 | | | | | 45 | | | |
| Leu | Leu | Thr | Phe | Leu | Ile | Ile | Ser | Gly | Asn | Leu | Thr | Val | Ile | Phe | Val |
| | 50 | | | | | 55 | | | | | 60 | | | | |
| Phe | His | Cys | Ala | Pro | Leu | Leu | His | His | Tyr | Thr | Thr | Ser | Tyr | Phe | Ile |
| 65 | | | | 70 | | | | | 75 | | | | | 80 | |
| Gln | Thr | Met | Ala | Tyr | Ala | Asp | Leu | Leu | Val | Gly | Val | Thr | Cys | Leu | Val |
| | | | | 85 | | | | | 90 | | | | | 95 | |
| Pro | Thr | Leu | Ser | Leu | Leu | His | Tyr | Ser | Thr | Gly | Val | His | Glu | Ser | Leu |
| | | | 100 | | | | | 105 | | | | | 110 | | |
| Thr | Cys | Gln | Val | Phe | Gly | Tyr | Ile | Ile | Ser | Val | Leu | Lys | Ser | Val | Ser |
| | | 115 | | | | | 120 | | | | | 125 | | | |
| Met | Ala | Cys | Leu | Ala | Cys | Ile | Ser | Val | Asp | Arg | Tyr | Leu | Ala | Ile | Thr |
| 130 | | | | | 135 | | | | | 140 | | | | | |
| Lys | Pro | Leu | Ser | Tyr | Asn | Gln | Leu | Val | Thr | Pro | Cys | Arg | Leu | Arg | Ile |
| 145 | | | | | 150 | | | | | 155 | | | | | 160 |
| Cys | Ile | Ile | Met | Ile | Trp | Ile | Tyr | Ser | Cys | Leu | Ile | Phe | Leu | Pro | Ser |
| | | | | 165 | | | | | 170 | | | | | 175 | |
| Phe | Phe | Gly | Trp | Gly | Lys | Pro | Gly | Tyr | His | Gly | Asp | Ile | Phe | Glu | Trp |
| | | | 180 | | | | | 185 | | | | | 190 | | |
| Cys | Ala | Thr | Ser | Trp | Leu | Thr | Ser | Ala | Tyr | Phe | Thr | Cys | Phe | Ile | Val |
| | | | 195 | | | | | 200 | | | | | 205 | | |
| Cys | Leu | Leu | Tyr | Ala | Pro | Ala | Ala | Leu | Val | Val | Cys | Phe | Thr | Tyr | Phe |
| | 210 | | | | | 215 | | | | | 220 | | | | |
| His | Ile | Phe | Lys | Ile | Cys | Arg | Gln | His | Thr | Lys | Glu | Ile | Asn | Asp | Arg |
| 225 | | | | | 230 | | | | | 235 | | | | | 240 |
| Arg | Ala | Arg | Phe | Pro | Ser | His | Glu | Val | Asp | Ala | Ser | Arg | Glu | Ala | Gly |
| | | | | 245 | | | | | 250 | | | | | 255 | |
| His | Ser | Pro | Asp | Arg | Arg | Tyr | Ala | Met | Val | Leu | Phe | Arg | Ile | Thr | Ser |
| | | | 260 | | | | | 265 | | | | | 270 | | |
| Val | Phe | Tyr | Met | Leu | Trp | Leu | Pro | Tyr | Ile | Ile | Tyr | Phe | Leu | Leu | Glu |
| | | | 275 | | | | | 280 | | | | | 285 | | |
| Ser | Ser | Arg | Val | Leu | Asp | Asn | Pro | Thr | Leu | Ser | Phe | Leu | Thr | Thr | Trp |
| | 290 | | | | | 295 | | | | | 300 | | | | |
| Leu | Ala | Ile | Ser | Asn | Ser | Phe | Cys | Asn | Cys | Val | Ile | Tyr | Ser | Leu | Ser |
| 305 | | | | | 310 | | | | | 315 | | | | | 320 |
| Asn | Ser | Val | Phe | Arg | Leu | Gly | Leu | Arg | Arg | Leu | Ser | Gln | Thr | Met | Cys |
| | | | | 325 | | | | | 330 | | | | | 335 | |
| Thr | Ser | Cys | Val | Cys | Gly | Lys | Asp | Gln | Glu | Ala | Arg | Asp | Pro | Lys | Pro |
| | | | 340 | | | | | 345 | | | | | 350 | | |
| Arg | Arg | Arg | Ala | Asn | Ser | Cys | Ser | Ile | | | | | | | |
| | | | | 355 | | | | | 360 | | | | | | |

<210> SEQ ID NO 4
<211> LENGTH: 1083
<212> TYPE: DNA
<213> ORGANISM: Norvegicus rattus

<400> SEQUENCE: 4
atgaatgaat ccaggtggac tgaatggagg atcctgaacg tgagcagtag cattgtgaat    60

```
gtgtccgagc atcactcctg ccctcttgga tttggtcact acagtgtgga ggatgtctgc    120
atctttgaga cagttgtcat tgtcttgctg acatttctga tcatctctgg gaatttaacc    180
gtcatctttg tctttcactg tgctccgctg ttacaccatt atactaccag ctacttcata    240
cagacgatgg catatgctga cctcctcgtt ggagttacct gcttggttcc tactctgtcc    300
cttcttcatt actctacagg tgtccacgag tcattgacct gccaggtgtt tggatatatt    360
atttcagttc taaaaagtgt ttctatggca tgtcttgctt gcatcagtgt ggatcgatat    420
cttgcaataa ccaagcctct ttcctacaat caactggtca ctccttgtcg cctgagaatt    480
tgcattatta tgatttggat ttactcctgc ctaattttct tgccttcctt ttttggctgg    540
ggcaaacctg gttaccatgg tgacattttt gaatggtgtg ccacatcttg gcttaccagt    600
gcctatttta cttgttttat tgtttgttta ctttatgctc ctgctgcctt ggttgtctgc    660
ttcacttact ttcacatttt caaaatctgc cggcagcaca ccaaagagat aaatgaccgg    720
agggcccgat tccctagcca cgaggtagat gcctctaggg aagcaggaca cagccctgat    780
cgtcgctacg ccatggtttt atttagaata actagcgtgt tttacatgct atggcttccg    840
tatattattt actttcttct agaaagttct cgtgtcttgg acaatccaac actgtccttc    900
ttaaccacct ggcttgctat aagcaatagt ttctgcaact gtgtaatata cagcctctcc    960
aacagtgttt tccgtctcgg cctccgaagg ctttctcaga caatgtgtac atcttgtgtg   1020
tgtgggaagg atcaggaagc acgagatccc aaacctagga gacgggcaaa ttcctgctcc   1080
att                                                                 1083

<210> SEQ ID NO 5
<211> LENGTH: 361
<212> TYPE: PRT
<213> ORGANISM: Mus musculus

<400> SEQUENCE: 5

Met Asn Glu Ser Arg Trp Thr Glu Trp Arg Ile Leu Asn Met Ser Ser
1               5                   10                  15

Ser Ile Val Asn Val Ser Glu His His Ser Cys Pro Leu Gly Phe Gly
            20                  25                  30

His Tyr Ser Val Glu Asp Val Cys Ile Phe Glu Thr Val Val Ile Val
        35                  40                  45

Leu Leu Thr Phe Leu Ile Ile Ser Gly Asn Leu Thr Val Ile Phe Val
    50                  55                  60

Phe His Cys Ala Pro Leu Leu His Tyr Thr Thr Ser Tyr Phe Ile
65                  70                  75                  80

Gln Thr Met Ala Tyr Ala Asp Leu Leu Val Gly Val Thr Cys Leu Val
                85                  90                  95

Pro Thr Leu Ser Leu Leu His Tyr Ser Thr Gly Val His Glu Ser Leu
            100                 105                 110

Thr Cys Gln Val Phe Gly Tyr Ile Ile Ser Val Leu Lys Ser Val Ser
        115                 120                 125

Met Ala Cys Leu Ala Cys Ile Ser Val Asp Arg Tyr Leu Ala Ile Thr
    130                 135                 140

Lys Pro Leu Ser Tyr Asn Gln Leu Val Thr Pro Cys Arg Leu Arg Ile
145                 150                 155                 160

Cys Ile Ile Met Ile Trp Ile Tyr Ser Cys Leu Ile Phe Leu Pro Ser
                165                 170                 175

Phe Phe Gly Trp Gly Lys Pro Gly Tyr His Gly Asp Ile Phe Glu Trp
            180                 185                 190
```

```
Cys Ala Thr Ser Trp Leu Thr Ser Ala Tyr Phe Thr Cys Phe Ile Val
            195                 200                 205

Cys Leu Leu Tyr Ala Pro Ala Ala Leu Val Val Cys Phe Thr Tyr Phe
            210                 215                 220

His Ile Phe Lys Ile Cys Arg Gln His Thr Lys Glu Ile Asn Asp Arg
225                 230                 235                 240

Arg Ala Arg Phe Pro Ser His Glu Val Glu Ala Ser Arg Glu Ala Gly
                245                 250                 255

His Ser Pro Asp Arg Arg Tyr Ala Met Val Leu Phe Arg Ile Thr Ser
            260                 265                 270

Val Phe Tyr Met Leu Trp Leu Pro Tyr Ile Ile Tyr Phe Leu Leu Glu
            275                 280                 285

Ser Ser Arg Val Leu Asp Asn Pro Thr Leu Ser Phe Leu Thr Thr Trp
            290                 295                 300

Leu Ala Ile Ser Asn Ser Phe Cys Asn Cys Val Ile Tyr Ser Leu Ser
305                 310                 315                 320

Asn Ser Val Phe Arg Leu Gly Leu Arg Arg Leu Ser Glu Thr Met Cys
                325                 330                 335

Thr Ser Cys Val Cys Ala Lys Asp Gln Glu Ala Gln Asp Pro Lys Pro
            340                 345                 350

Arg Arg Arg Ala Asn Ser Cys Ser Ile
            355                 360

<210> SEQ ID NO 6
<211> LENGTH: 1083
<212> TYPE: DNA
<213> ORGANISM: Mus musculus

<400> SEQUENCE: 6
atgaatgaat ccaggtggac tgaatggagg atcctgaaca tgagcagtag cattgtgaat      60
gtgtccgagc accactcctg ccctcttgga tttggtcact acagtgtgga ggatgtctgc     120
atctttgaga cagttgtcat tgtcttgctg acatttctga tcatctctgg gaatttaaca     180
gtcatctttg tctttcactg tgctccgctg ttacaccatt atactaccag ctactttata     240
cagaccatgg catacgctga cctcctcgtt ggagttacct gcttggttcc tactctgtcc     300
cttcttcatt actctacagg tgtccatgag tcattgactg ccaggtgtt tggatatatt      360
atttcagttc taaaaagcgt gtctatggca tgtcttgctt gcatcagtgt ggatcgatat     420
cttgcaataa ccaagcctct atcctacaat caactggtca ctccttgtcg cctgagaatt     480
tgcattatta tgatttggat ttactcctgc taatttttct tgccttcctt ttttggctgg     540
ggcaaacctg gttaccatgg tgacattttt gaatggtgtg ccacatcttg cttaccagt     600
gcctatttta cttgctttat tgtttgttta ctttatgctc ctgctgcctt ggttgtctgc     660
ttcacttact ttcacatttt caaaatttgc cggcagcaca ccaaagagat aaatgaccgg     720
agggccagat ccctagtca cgaggtagag gcctctaggg aagcagggca cagccctgac     780
cgtcgctacg ccatggtttt atttaggata actagcgtgt tttacatgct gtggcttcca     840
tatattattt actttcttct agaaagttct cgtgtcttgg acaatcccac actgtccttc     900
ttaaccacct ggcttgcgat aagcaatagt ttttgtaact gtgtaatata cagcctctcc     960
aacagtgttt tccgccttgg cctccgaagg ctttctgaaa caatgtgcac atcttgtgtg    1020
tgtgcgaagg atcaggaagc acaagatccc aaacctagga cgggcaaa ttcctgctcc    1080
att                                                                  1083
```

```
<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctcgagccac catgaatgaa tccaggtgga ctg                                    33

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gctagctcaa atggagcagg aatttgcc                                          28

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gtcagcacac caaagagata aatga                                             25

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtgtccagtc tctctggaag aatcta                                            26

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
cgaagagccc gattccctag tcatgag                                           27

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gttgtctgct tcacttactt tcacatt                                           27

<210> SEQ ID NO 13
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggccctccgg tcatttatct                                                  20

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
tcaaaatttg caggcagcac accaa                                            25

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gattccctag ccacgaggta ga                                               22

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccatggcgta gcgacgat                                                    18

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
cctctaggga agcaggacac agccct                                           26
```

SCREENING METHODS USING GPR52

TECHNICAL FIELD

The present invention relates to screening methods and screening kits for medicaments which comprises using ligands capable of specifically binding to GPR52 receptors and GPR52 receptors, compounds which are obtainable by the screening methods or kits, etc. More particularly, the present invention relates to screening methods and screening kits for preventive/therapeutic agents for mental disorders, prolactin-related disorders, and so on.

BACKGROUND ART

G protein-coupled receptors (GPCR) are seven-transmembrane receptors and are responsible for actions to transduce the signals of hormones, neurotransmitters, cytokines and other molecules, across the cell membrane.

Human GPR52 (Molecular Brain Research, 64, 193-198, 1999) is one of GPCR, for which no ligand has been reported, and its role or function has also not been reported.

It is known that reserpine (formula below) is an alkaloid contained in *Rauwolfia serpentina* and has a central depressant effect and hypotensive effect (Am. J. Chin. Med. 7, 197-236, 1979). Reserpine is used as a drug for improving schizophrenia, antipsychotic drug, hypotensive drug and sedative.

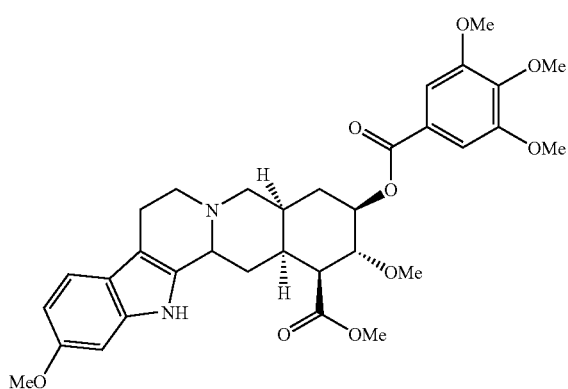

Methoctramine (formula below) is known as an antagonist of muscarinic acetylcholine receptor M2 (Eur. J. Pharmacol., 144, 117-124, 1987).

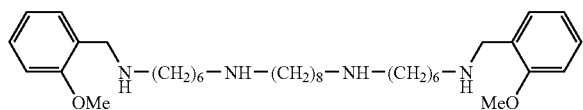

DISCLOSURE OF INVENTION

There is a need for safe and excellent drugs for the prevention/treatment of mental disorders, prolactin-related disease, etc.

In order to solve the foregoing problems, the present inventors made extensive studies and found that reserpine and methoctramine are ligands for GPR52. The inventors inferred that search of drugs effective for mental disorders could be performed by using GPR52 and these ligands. Based on these findings, the inventors have made further studies and as a result have come to accomplish the present invention.

That is, the present invention relates to the following features:

[1] A method of screening a compound or a salt thereof that changes the binding property of a protein comprising the same or substantially the same amino acid sequence as the amino acid sequence represented by SEQ ID NO: 1 or a salt thereof, to a ligand capable of specifically binding to said protein or a salt thereof, which comprises using (a) said protein, its partial peptide, or a salt thereof, and (b) said ligand.

[2] The screening method according to [1] above, wherein the ligand is a reserpine compound.

[3] The screening method according to [2] above, wherein the reserpine compound is a compound represented by the formula:

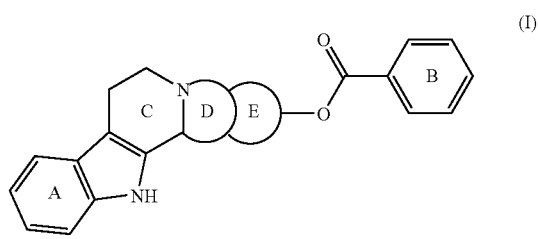

wherein each of Ring A and Ring B is an optionally substituted benzene ring, Ring C is an optionally substituted 6-membered ring, Ring D is an optionally substituted 5- to 7-membered nitrogen-containing hetero ring, and, Ring E is an optionally substituted 5- to 7-membered ring; or a salt thereof (hereinafter simply referred to as Compound (I)).

[3a] The screening method according to [3] above, wherein Compound (I) is represented by formula below:

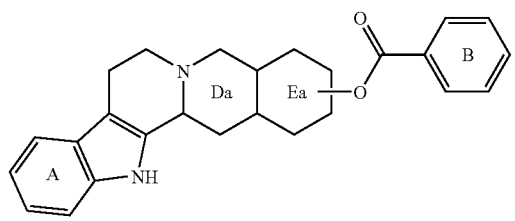

wherein Ring Da is an optionally substituted 6-membered nitrogen-containing hetero ring;

Ring Ea is an optionally substituted 6-membered ring; and,

Ring A and Ring B have the same significance as defined above; or a salt thereof.

[4] The screening method according to [2] above, wherein the reserpine compound is reserpine.

[5] The screening method according to [1] above, wherein the ligand is an indole alkaloid.

[5a] The screening method according to [2] above, wherein the indole alkaloid is a *rauwolfia* alkaloid.

[6] The screening method according to [1] above, wherein the ligand is a methoctramine compound.

[7] The screening method according to [6] above, wherein the methoctramine compound is a compound represented by the formula:

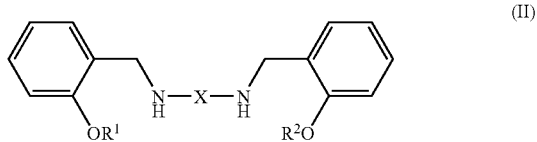

(II)

wherein each of $R^1$ and $R^2$ represents an optionally substituted hydrocarbon group and X represents a spacer; or a salt thereof (hereinafter simply referred to as Compound (II)).

[8] The screening method according to [6] above, wherein the methoctramine compound is methoctramine.

[9] The screening method according to [1] above, wherein substantially the same amino acid sequence as the amino acid sequence represented by SEQ ID NO: 1 is the amino acid sequence represented by SEQ ID NO: 3 or SEQ ID NO: 5.

[10] The screening method according to [1] above, which comprises assaying the binding amounts of a ligand capable of specifically binding to a protein comprising the same or substantially the same amino acid sequence as the amino acid sequence represented by SEQ ID NO: 1, its partial peptide, or a salt thereof, to said protein, its partial peptide, or a salt thereof, (a) in the case of contacting said ligand with said protein, its partial peptide, or a salt thereof and (b) in the case of contacting said ligand and a test compound with said protein, its partial peptide, or a salt thereof, and comparing the binding amounts.

[11] The screening method according to [1] above, which comprises assaying the binding amounts of a ligand capable of specifically binding to a protein comprising the same or substantially the same amino acid sequence as the amino acid sequence represented by SEQ ID NO: 1, its partial peptide, or a salt thereof, to a cell containing said protein, its partial peptide, or a salt thereof, or a membrane fraction of the cell, (a) in the case of contacting said ligand with said cell or a membrane fraction of the cell and (b) in the case of contacting said ligand and a test compound with said cell or said membrane fraction, and comparing the binding amounts.

[12] The screening method according to [10] above, wherein the protein comprising the same or substantially the same amino acid sequence as the amino acid sequence represented by SEQ ID NO: 1, its partial peptide, or a salt thereof is a protein, its partial peptide, or a salt thereof, which protein is expressed on a cell membrane by culturing a transformant containing a DNA encoding said protein, its partial peptide, or a salt thereof.

[13] The screening method according to [10] to [12] above, wherein the ligand is a labeled ligand.

[14] The screening method according to [1] above, which comprises assaying cell stimulating activities mediated by a protein comprising the same or substantially the same amino acid sequence as the amino acid sequence represented by SEQ ID NO: 1, its partial peptide, or a salt thereof, (a) in the case of contacting a ligand capable of specifically binding to said protein, its partial peptide, or a salt thereof with said protein, its partial peptide, or a salt thereof and (b) in the case of contacting said ligand and a test compound with said protein, its partial peptide, or a salt thereof, and comparing the cell stimulating activities.

[15] The screening method according to [1] above, which comprises assaying cell stimulating activities mediated by a protein comprising the same or substantially the same amino acid sequence as the amino acid sequence represented by SEQ ID NO: 1, its partial peptide, or a salt thereof, (a) in the case of contacting a ligand capable of specifically binding to said protein, its partial peptide, or a salt thereof with a cell containing said protein, its partial peptide, or a salt thereof or a membrane fraction of said cell and (b) in the case of contacting said ligand and a test compound with a cell containing said protein, its partial peptide, or a salt thereof, or a membrane fraction of said cell, and comparing the cell stimulating activities.

[16] The screening method according to [15] above, wherein the cell stimulating activity is a Gs activity.

[17] The screening method according to [15] above, wherein the protein comprising the same or substantially the same amino acid sequence as the amino acid sequence represented by SEQ ID NO: 1, its partial peptide, or a salt thereof is a protein, its partial peptide, or a salt thereof, which protein is expressed on a cell membrane by culturing a transformant containing a DNA encoding said protein, its partial peptide, or a salt thereof.

[17a] A method of screening an agonist or antagonist to a protein comprising the same or substantially the same amino acid sequence as the amino acid sequence represented by SEQ ID NO: 1 or a salt thereof, which comprises using (a) said protein, its partial peptide, or a salt thereof, and (b) a ligand capable of specifically binding to said protein or a salt thereof.

[17b] A method of screening an agonist or antagonist to a protein comprising the same or substantially the same amino acid sequence as the amino acid sequence represented by SEQ ID NO: 1 or a salt thereof, which comprises using a compound or a salt thereof that changes the binding properties of (a) said protein, its partial peptide, or a salt thereof, and (b) a ligand capable of specifically binding to said protein or a salt thereof.

[18] A method of screening an agonist for a protein comprising the same or substantially the same amino acid sequence as the amino acid sequence represented by SEQ ID NO: 1, or a salt thereof, which comprises (i) assaying cell stimulating activities mediated by said protein, its partial peptide, or a salt thereof, (a) in the case of contacting a ligand capable of specifically binding to said protein, its partial peptide, or a salt thereof with a cell containing said protein, its partial peptide, or a salt thereof, and (b) in the case of contacting a test compound with a cell containing said protein, its partial peptide, or a salt thereof, and comparing the cell stimulating activities, or (ii) assaying cell stimulating activities mediated by said protein, its partial peptide, or a salt thereof, in the case of contacting a test compound with a cell containing said protein, its partial peptide, or a salt thereof.

[19] A method of screening an antagonist to a protein comprising the same or substantially the same amino acid sequence as the amino acid sequence represented by SEQ ID NO: 1, or a salt thereof, which comprises assaying cell stimulating activities mediated by said protein, its partial peptide, or a salt thereof, in the case of contacting a test compound with a cell containing said protein, its partial peptide, or a salt thereof, in the presence of a ligand capable of specifically binding to said protein, its partial peptide, or a salt thereof.

[20] A kit for screening a compound or a salt thereof that changes the binding properties of a protein comprising the same or substantially the same amino acid sequence as the amino acid sequence represented by SEQ ID NO: 1, or a salt thereof to a ligand capable of specifically binding to said protein or a salt thereof, which comprises (a) said protein or a salt thereof and (b) said ligand.

[20a] A compound or a salt thereof, which is obtainable by using the screening method according to [1] above or the screening kit according to [20] above.

[20b] The compound or a salt thereof according to [20a] above, wherein the compound is a compound or a salt thereof that inhibits the binding of a protein comprising the same or substantially the same amino acid sequence as the amino acid sequence represented by SEQ ID NO: 1, its partial peptide, or a salt thereof, to a ligand.

[20c] The compound or a salt thereof according to [20b] above, which is an agonist.

[20d] The compound or a salt thereof according to [20b] above, which is an antagonist.

[20e] A medicament comprising a compound or a salt thereof that inhibits the binding of a protein comprising the same or substantially the same amino acid sequence as the amino acid sequence represented by SEQ ID NO: 1, its partial peptide, or a salt thereof, to a ligand.

[20f] An agent for the prevention/treatment of schizophrenia or cognitive impairment, which comprises the compound or a salt thereof according to [20c] above.

[20g] An agent for the prevention/treatment of Parkinson's disease, which comprises the compound or a salt thereof according to [20d] above.

[21] An agent for preventing/treating schizophrenia or cognitive impairment, which comprises a compound or a salt thereof that promotes the activity of a protein comprising the same or substantially the same amino acid sequence as the amino acid sequence represented by SEQ ID NO: 1, its partial peptide, or a salt thereof.

[22] An agent for preventing/treating prolactin hyposecretion, which comprises a compound or a salt thereof that promotes the activity of a protein comprising the same or substantially the same amino acid sequence as the amino acid sequence represented by SEQ ID NO: 1, its partial peptide, or a salt thereof.

[23] An agent for preventing/treating Parkinson's disease, which comprises a compound or a salt thereof that inhibits the activity of a protein comprising the same or substantially the same amino acid sequence as the amino acid sequence represented by SEQ ID NO: 1, its partial peptide, or a salt thereof.

[24] An agent for preventing/treating hyperprolactinemia, which comprises a compound or a salt thereof that inhibits the activity of a protein comprising the same or substantially the same amino acid sequence as the amino acid sequence represented by SEQ ID NO: 1, its partial peptide, or a salt thereof.

[25] A ligand capable of specifically binding to a protein comprising the same or substantially the same amino acid sequence as the amino acid sequence represented by SEQ ID NO: 1 or a salt thereof.

[26] A method for preventing/treating schizophrenia or cognitive impairment, which comprises promoting the activity of a protein comprising the same or substantially the same amino acid sequence as the amino acid sequence represented by SEQ ID NO: 1, its partial peptide, or a salt thereof.

[27] A method for preventing/treating prolactin hyposecretion, which comprises promoting the activity of a protein comprising the same or substantially the same amino acid sequence as the amino acid sequence represented by SEQ ID NO: 1, its partial peptide, or a salt thereof.

[28] A method for preventing/treating Parkinson's disease, which comprises inhibiting the activity of a protein comprising the same or substantially the same amino acid sequence as the amino acid sequence represented by SEQ ID NO: 1, its partial peptide, or a salt thereof.

[29] A method for preventing/treating hyperprolactinemia, which comprises inhibiting the activity of a protein comprising the same or substantially the same amino acid sequence as the amino acid sequence represented by SEQ ID NO: 1, its partial peptide, or a salt thereof.

[30] A method for preventing/treating schizophrenia or cognitive impairment, which comprises administering to a mammal an effective dose of a compound or a salt thereof that promotes the activity of a protein comprising the same or substantially the same amino acid sequence as the amino acid sequence represented by SEQ ID NO: 1, its partial peptide, or a salt thereof.

[31] A method for preventing/treating prolactin hyposecretion, which comprises administering to a mammal an effective dose of a compound or a salt thereof that promotes the activity of a protein comprising the same or substantially the same amino acid sequence as the amino acid sequence represented by SEQ ID NO: 1, its partial peptide, or a salt thereof.

[32] A method for preventing/treating Parkinson's disease, which comprises administering to a mammal an effective dose of a compound or a salt thereof that inhibits the activity of a protein comprising the same or substantially the same amino acid sequence as the amino acid sequence represented by SEQ ID NO: 1, its partial peptide, or a salt thereof.

[33] A method for preventing/treating hyperprolactinemia, which comprises administering to a mammal an effective dose of a compound or a salt thereof that inhibits the activity of a protein comprising the same or substantially the same amino acid sequence as the amino acid sequence represented by SEQ ID NO: 1, its partial peptide, or a salt thereof.

[34] Use of a compound or a salt thereof that promotes the activity of a protein comprising the same or substantially the same amino acid sequence as the amino acid sequence represented by SEQ ID NO: 1, its partial peptide, or a salt thereof, to manufacture an agent for preventing/treating schizophrenia or cognitive impairment.

[35] Use of a compound or a salt thereof that promotes the activity of a protein comprising the same or substantially the same amino acid sequence as the amino acid sequence represented by SEQ ID NO: 1, its partial peptide, or a salt thereof, to manufacture an agent for preventing/treating prolactin hyposecretion.

[36] Use of a compound or a salt thereof that inhibits the activity of a protein comprising the same or substantially the same amino acid sequence as the amino acid sequence represented by SEQ ID NO: 1, its partial peptide, or a salt thereof, to manufacture an agent for preventing/treating Parkinson's disease.

[37] Use of a compound or a salt thereof that inhibits the activity of a protein comprising the same or substantially the same amino acid sequence as the amino acid sequence represented by SEQ ID NO: 1, its partial peptide, or a salt thereof, to manufacture an agent for preventing/treating hyperprolactinemia.

Moreover, the present invention provides the following features:

(1) a protein comprises the same or substantially the same amino acid sequence as the amino acid sequence represented by SEQ ID NO: 3 or SEQ ID NO: 5, or a salt thereof;

(2) a partial peptide of the protein according to (1) above, or a salt thereof;

(3) a polynucleotide comprising a polynucleotide encoding the protein according to (1) above;
(4) the polynucleotide according to (3) above, which is a DNA;
(5) the DNA according to (4) above, which comprises the base sequence represented by SEQ ID NO: 4 or SEQ ID NO: 6;
(6) a recombinant vector comprising the polynucleotide according to (3) above;
(7) a transformant transformed with the recombinant vector according to (6) above;
(8) a method for producing the protein according to (1) above or a salt thereof, which comprises culturing the transformant according to (7) above and producing the protein according to (1) above or a salt thereof,
(9) an antibody to the protein according to (1) above, its partial peptide, or a salt thereof;
(10) a method for determining a ligand to the protein according to (1) above or a salt thereof, which comprises using the protein according to (1) above, its partial peptide, or a salt thereof;
(11) a polynucleotide hybridizable to the polynucleotide according to (3) above under highly stringent conditions;
(12) an antisense polynucleotide, which comprises a complementary or substantially complementary base sequence to the polynucleotide according to (3) above, or a part thereof;
(13) a method for quantifying mRNA of the protein according to (1) above, which comprises using the polynucleotide according to (3) above or a part thereof;
(14) a method for quantifying the protein according to (1) above, which comprises using the antibody according to (9) above;
(15) a non-human transgenic animal bearing a DNA encoding the protein according to (1) above or its variant DNA, which is exogenous;
(16) the animal according to (15) above, wherein the non-human animal is a rodent;
(17) the animal according to (16) above, wherein the rodent is mouse or rat;
(18) a recombinant vector comprising a DNA encoding the protein according to (1) above or its variant DNA, which is exogenous, and capable of expressing in a non-human animal;
(19) a non-human mammal embryonic stem cell, in which the DNA encoding the protein according to (1) above is inactivated;
(20) the embryonic stem cell according to (19) above, wherein the non-human mammal is a rodent;
(21) the embryonic stem cell according to (20) above, wherein the rodent is mouse;
(22) a non-human mammal deficient in expressing a DNA encoding the protein according to (1) above, wherein the DNA is inactivated;
(23) the non-human mammal according to (22) above, wherein the non-human mammal is a rodent, and so on.

Hereinafter, the "protein comprising the same or substantially the same amino acid sequence as the amino acid sequence represented by SEQ ID NO: 1, its partial peptide, or a salt thereof" is sometimes briefly referred to as the "receptor of the present invention" or the "protein of the present invention." Also, the "ligand capable of specifically binding to the receptor of the present invention" is sometimes briefly referred to as the "ligand of the present invention."

Furthermore, the present invention provides the following features:
(i) a method of screening a compound that changes binding properties of the ligand of the present invention to the receptor of the present invention, which comprises assaying the GTPγS binding-promoting activities on a cell membrane fraction containing the receptor of the present invention, in the presence of labeled GTPγS, in the case of contacting the ligand of the present invention with the cell membrane fraction containing the receptor of the present invention, and in the case of contacting the ligand of the present invention and a test compound with the cell membrane fraction containing the receptor of the present invention; and comparing the activities;
(i') a method of screening an agonist for the receptor of the present invention, which comprises contacting a test compound with the cell membrane fraction containing the receptor of the present invention and assaying the GTPγS binding-promoting activities on a cell membrane fraction containing the receptor of the present invention;
(ii) a method of screening a compound that changes binding properties of the ligand of the present invention to the receptor of the present invention, which comprises assaying intracellular cAMP level of a cell wherein the receptor of the present invention is expressed, in the case of contacting the ligand of the present invention with said cell and in the case of contacting the ligand of the present invention and a test compound with said cell; and comparing the activities;
(ii') a method of screening an agonist for the receptor of the present invention, which comprises contacting a test compound with a cell wherein the receptor of the present invention is expressed and assaying intracellular cAMP levels of said cell (preferably, intracellular cAMP production promoting activities);
(iii) a method of screening a compound that changes binding properties of the ligand of the present invention to the receptor of the present invention, which comprises assaying enzyme activities of a reporter gene protein, in the case of contacting the ligand of the present invention with a CRE-reporter gene vector-transfected cell wherein the receptor of the present invention is expressed; and in the case of contacting the ligand of the present invention and a test compound with a CRE-reporter gene vector-transfected cell wherein the receptor of the present invention is expressed; and comparing the activities;
(iii') a method of screening an agonist for the receptor of the present invention, which comprises contacting a test compound with a CRE-reporter gene vector-transfected cell wherein the receptor of the present invention is expressed and assaying enzyme activities of a reporter gene protein;
(iv) a method of screening a compound that changes binding properties of the ligand of the present invention to the receptor of the present invention, which comprises assaying enzyme activities of a reporter gene protein, in the case of contacting the ligand of the present invention with a SRE-reporter gene vector-transfected cell wherein the receptor of the present invention is expressed; and in the case of contacting the ligand of the present invention and a test compound with a SRE-reporter gene vector-transfected cell wherein the receptor of the present invention is expressed; and comparing the activities;
(iv') a method of screening an agonist for the receptor of the present invention, which comprises contacting a test compound with a SRE-reporter gene vector-transfected cell wherein the receptor of the present invention is expressed and assaying enzyme activities of a reporter gene protein;
(v) a method of screening a compound that changes binding properties of the ligand of the present invention to the receptor of the present invention, which comprises assaying arachidonic acid metabolite-releasing activities, in the case of contacting the ligand of the present invention with a cell wherein the receptor of the present invention containing labeled arachidonic acid is expressed and in the case of contacting the ligand of the present invention and a test compound with a cell wherein the receptor of the present invention containing labeled arachidonic acid is expressed; and comparing the activities;

(v') a method of screening an agonist for the receptor of the present invention, which comprises contacting a test compound with a cell wherein the receptor of the present invention containing labeled arachidonic acid is expressed and assaying arachidonic acid metabolite-releasing activities;

(vi) a method of screening a compound that changes the binding properties of the ligand of the present invention to the receptor of the present invention, which comprises assaying intracellular calcium level increasing activities, in the case of contacting the ligand of the present invention with a cell wherein the receptor of the present invention is expressed and in the case of contacting the ligand of the present invention and a test compound with a cell wherein the receptor of the present invention is expressed; and comparing the activities;

(vi') a method of screening an agonist for the receptor of the present invention, which comprises contacting a test compound with a cell wherein the receptor of the present invention expressed and assaying intracellular calcium level increasing activities;

(vii) a method of screening a compound that changes the binding properties of the ligand of the present invention to the receptor of the present invention, which comprises assaying inositol triphosphate producing activities in the presence of labeled inositol, in the case of contacting the ligand of the present invention with a cell wherein the receptor of the present invention is expressed and in the case of contacting the ligand of the present invention and a test compound with a cell wherein the receptor of the present invention is expressed; and comparing the activities;

(vii') a method of screening an agonist for the receptor of the present invention, which comprises contacting a test compound with a cell wherein the receptor of the present invention expressed and assaying inositol triphosphate producing activities in the presence of labeled inositol;

(viii) a method of screening a compound that changes the binding properties of the ligand of the present invention to the receptor of the present invention, which comprises assaying enzyme activities of a reporter gene protein, in the case of contacting the ligand of the present invention with a TRE-reporter gene vector-transfected cell wherein the receptor of the present invention is expressed and in the case of contacting the ligand of the present invention and a test compound with a TRE-reporter gene vector-transfected cell wherein the receptor of the present invention is expressed; and comparing the activities;

(viii') a method of screening an agonist for the receptor of the present invention, which comprises contacting a test, compound with a TRE-reporter gene vector-transfected cell wherein the receptor of the present invention is expressed and assaying enzyme activities of a reporter gene protein;

(ix) a method of screening a compound that changes the binding properties of the ligand of the present invention to the receptor of the present invention, which comprises assaying cell growth, in the case of contacting the ligand of the present invention with a cell wherein the receptor of the present invention is expressed and in the case of contacting the ligand of the present invention and a test compound with a cell wherein the receptor of the present invention is expressed; and comparing the cell growth;

(ix') a method of screening an agonist for the receptor of the present invention, which comprises contacting a test compound with a cell wherein the receptor of the present invention is expressed and assaying cell growth;

(x) a method of screening a compound that changes the binding properties of the ligand of the present invention to the receptor of the present invention, which comprises assaying efflux activities of labeled rubidium in the presence of labeled rubidium, in the case of contacting the ligand of the present invention with a cell wherein the receptor of the present invention is expressed and in the case of contacting the ligand of the present invention and a test compound with a cell wherein the receptor of the present invention is expressed; and comparing the activities;

(x') a method of screening an agonist for the receptor of the present invention, which comprises contacting a test compound with a cell wherein the receptor of the present invention is expressed and assaying efflux activities of labeled rubidium in the presence of labeled rubidium;

(xi) a method of screening a compound that changes the binding properties of the ligand of the present invention to the receptor of the present invention, which comprises assaying extracellular pH changes, in the case of contacting the ligand of the present invention with a cell wherein the receptor of the present invention is expressed and in the case of contacting the ligand of the present invention and a test compound with a cell wherein the receptor of the present invention is expressed; and comparing the changes;

(xi') a method of screening an agonist for the receptor of the present invention, which comprises contacting a test compound with a cell wherein the receptor of the present invention is expressed and assaying extracellular pH changes;

(xii) a method of screening a compound that changes the binding properties of the ligand of the present invention to the receptor of the present invention, which comprises culturing in a histidine-deficient medium a histidine synthase gene-transfected yeast wherein the receptor of the present invention is expressed; assaying growth of said yeast, in the case of contacting the ligand of the present invention or the ligand of the present invention and a test compound with the yeast; and comparing growth of said yeast;

(xii') a method of screening an agonist for the receptor of the present invention, which comprises contacting a test compound with a histidine synthase gene-transfected yeast wherein the receptor of the present invention is expressed and assaying growth of said yeast;

(xiii) a method of screening a compound that changes the binding properties of the ligand of the present invention to the receptor of the present invention, which comprises assaying changes in cell membrane potentials, in the case of contacting the ligand of the present invention with *Xenopus laevis* oocytes wherein RNA of a gene for the receptor of the present invention is transfected and in the case of contacting the ligand of the present invention and a test compound with *Xenopus laevis* oocytes wherein RNA of a gene for the receptor of the present invention is transfected, and comparing the changes;

(xiii') a method of screening an agonist for the receptor of the present invention, which comprises contacting a test compound with *Xenopus laevis* oocytes wherein RNA of a gene for the receptor of the present invention is transfected and assaying changes in cell membrane potentials;

(xiv) a method of screening a compound that changes the binding properties of the ligand of the present invention to the receptor of the present invention, which comprises assaying degrees of internalization of the receptor, in the case of contacting the ligand of the present invention with a cell wherein the receptor of the present invention is expressed and in the case of contacting the ligand of the present invention and a test compound with a cell wherein the receptor of the present invention is expressed, and comparing the changes; and, (xiv') a method of screening an agonist for the receptor of the present invention, which comprises contacting a test compound with a cell wherein the receptor of the present invention is expressed and assaying degrees of internalization of the receptor.

The compound or its salt that promotes or inhibits the activities of the receptor (e.g., GPR52, etc.) of the present invention, the compound or its salt that promotes or inhibits the expression of a gene for the receptor of the present invention, the compound or its salt (e.g., GPR52 agonist, GPR52 antagonist) which is obtainable by the screening method or screening kit of the present invention, etc. are useful as agents for preventing/treating, for example, mental disorders (e.g., schizophrenia, anxiety, cognitive impairment, panic disorder, phobic disorder, drug-induced psychotic disorder, delusional psychosis, neuroleptic-induced dyskinesia, Parkinson's disease, drug-induced Parkinson's syndrome, extrapyramidal syndrome, etc.), prolactin-related disorders [e.g., hyperprolactinemia (e.g., sterility, galactorrhea, amenorrhea, atrophy of ovary and uterus, etc.), pituitary tumor, diencephalon tumor, menstrual disorder, prolactin hyposecretion (e.g., hypoovarianism, spermatic underdevelopment, menopausal symptoms, hypothyroidism, etc.), hypertension, sleeping disorders [e.g., primary insomnia, circadian rhythm disorders (e.g., change in physical conditions caused by three-shift work, time zone change syndrome (jet lag), etc.], and the like.

In addition, the compound or its salt that promotes the activities of the receptor of the present invention, the compound or its salt that promotes the expression of a gene for the receptor of the present invention, the agonist for the receptor of the present invention, the ligand to the receptor of the present invention, etc. increase the intracellular cAMP levels in neurons wherein the receptor (e.g., GPR52, etc.) of the present invention is expressed, and thus can prevent overactive mesolimbic dopamine pathway, which is considered as one of the causes for positive schizophrenia symptoms, and can improve the positive schizophrenia symptoms. Also, these compounds can improve hypofunction of the NMDA-type receptor in the cerebral cortex considered as one of the causes for negative schizophrenia symptoms or cognitive impairment thereby to improve negative schizophrenia symptoms or cognitive impairment. Accordingly, the compounds or their salts, agonists, ligands, and the like are useful as agents for the prevention/treatment of, preferably, schizophrenia, cognitive impairment, etc.

The compound or its salt that promotes the activities of the receptor of the present invention, the compound or its salt that promotes the expression of a gene for the receptor of the present invention, the agonist for the receptor of the present invention, the ligand to the receptor of the present invention, etc. can promote prolactin release and are useful as agents for preventing/treating prolactin hyposecretion (e.g., hypoovarianism, spermatic underdevelopment, menopausal symptoms, hypothyroidism, etc.), and so on.

The compound or its salt that inhibits the activities of the receptor of the present invention, the compound or its salt that inhibits the expression of a gene for the receptor of the present invention, the antagonist to the receptor of the present invention, etc. decrease the intracellular cAMP levels in neurons wherein the receptor (e.g., GPR52, etc.) of the present invention is expressed, and can improve failure in suppression of the intracellular cAMP production caused by dopamine deficiency in the nigrostriatal dopamine pathway, which is considered as one of the causes for Parkinson's disease. Preferably, these compounds are useful as agents for the prevention/treatment of Parkinson's disease, etc.

Moreover, the compound or its salt that inhibits the activities of the receptor of the present invention, the compound or its salt that inhibits the expression of a gene for the receptor of the present invention, the antagonist to the receptor of the present invention, etc. can suppress prolactin release and are useful as agents for preventing/treating prolactin hypersecretion [e.g., hyperprolactinemia (e.g., sterility, galactorrhea, amenorrhea, atrophy of ovary and uterus, etc.), pituitary tumor, diencephalon tumor, menstrual disorder, etc.], and the like.

Furthermore, the receptor (e.g., GPR52, etc.) of the present invention or/and its ligand (e.g., reserpine, methoctramine, etc.) are useful as agents for preventing/treating mental disorders, etc.

BEST MODE FOR CARRYING OUT THE INVENTION

Figure 1:
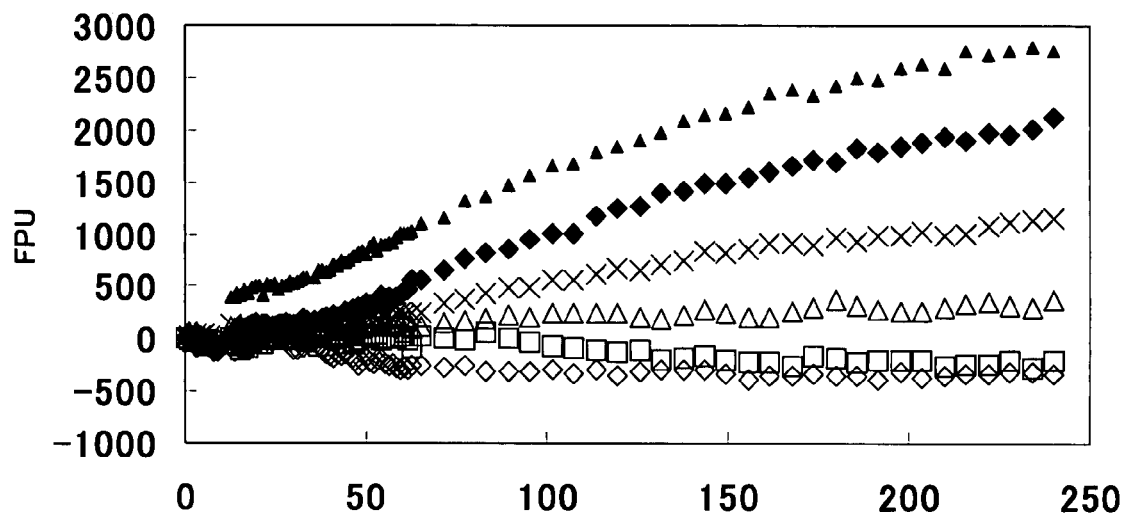
FIG. 1 shows the results obtained by monitoring changes in intracellular $Ca^{2+}$ levels where human GPR52 expression plasmid is transiently expressed in the CNGC-E583M/HEK293 cell line and reserpine is added. In the figure, the ordinate denotes fluorescence intensities showing the intracellular $Ca^{2+}$ levels and the abscissa denotes passage of time (second) after starting the measurements, in which ◇ (open diamond) represents HBSS buffer (Base), □ (open square) represents 1.0 µM reserpine, Δ (open triangle) represents 3.0 µM reserpine, x represents 10 µM reserpine, ◆ (closed diamond) represents 30 µM reserpine, and ▲ (closed triangle) represents 100 µM reserpine.

The protein having the same or substantially the same amino acid sequence as the amino acid sequence represented by SEQ ID NO: 1 may be any protein derived from any cells of human and warm-blooded animals (e.g., guinea pigs, rats, mice, fowl, rabbits, swine, sheep, bovine, monkeys, etc.) (e.g., retinal cells, hepatocytes, splenocytes, nerve cells, glial cells, β cells of pancreas, bone marrow cells, mesangial cells, Langerhans' cells, epidermic cells, epithelial cells, endothelial cells, fibroblasts, fibrocytes, myocytes, fat cells, immune cells (e.g., macrophage cells, T cells, B cells, natural killer cells, mast cells, neutrophils, basophils, eosinophils, monocytes), megakaryocytes, synovial cells, chondrocytes, bone cells, osteoblasts, osteoclasts, mammary gland cells, hepatocytes or interstitial cells; or the corresponding precursor cells, stem cells, cancer cells, etc.); or any tissues where such cells are present, such as brain or any of brain regions (e.g., retina, olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, prostate, testis, ovary, placenta, uterus, bone, joint, skeletal muscle, etc.; or proteins derived from hemocyte type cells or their cultured cells (e.g., MEL, M1, CTLL-2, HT-2, WEHI-3, HL-60, JOSK-1, K562, ML-1, MOLT-3, MOLT-4, MOLT-10, CCRF-CEM, TALL-1, Jurkat, CCRT-HSB-2, KE-37, SKW-3, HUT-78, HUT-102, H9, U937, THP-1, HEL, JK-1, CMK, KO-812, MEG-01, etc.); these proteins may also be synthetic proteins.

The amino acid sequence having substantially the same amino acid sequence as that represented by SEQ ID NO: 1 includes amino acid sequences having at least about 60% homology, preferably at least about 70% homology, preferably at least about 80% homology, more preferably at least about 90% homology, to the amino acid sequence shown by SEQ ID NO: 1; and so on.

Homology of the amino acid sequences can be measured under the following conditions (an expectation value=10; gaps are allowed; matrix=BLOSUM62; filtering =OFF) using a homology scoring algorithm NCBI BLAST (National Center for Biotechnology Information Basic Local Alignment Search Tool).

Preferred examples of the protein containing substantially the same amino acid sequence as the amino acid sequence represented by SEQ ID NO: 1 include proteins having substantially the same amino acid sequence as the amino acid sequence represented by SEQ ID NO: 1 and having an activity of substantially the same nature as that of the protein having the amino acid sequence represented by SEQ ID NO: 1, etc. The amino acid sequence which is substantially the same as the amino acid sequence represented by SEQ ID NO: 1 includes, e.g., an amino acid sequence represented by SEQ ID NO: 3, an amino acid sequence represented by SEQ ID NO: 5, etc.

Examples of the substantially equivalent activity include a ligand binding activity, a signal transduction activity, etc. The term substantially equivalent is used to mean that the activities are the same in nature. Therefore, it is preferred that activities such as the ligand binding and signal transduction activities, etc. be equivalent (e.g., about 0.01 to 100 times, preferably about 0.5 to 20 times, more preferably 0.5 to 2 times), but differences in degree such as a level of these activities, quantitative factors such as a molecular weight of the protein may be present and allowable.

The activities such as ligand binding and signal transduction activities or the like can be determined according to publicly known methods with some modifications thereof. For example, the activities can be assayed in accordance with the methods of determining ligands or screening methods which will be later described.

Examples of the proteins of the present invention containing the following amino acid sequences, which are used as the receptor of the present invention include: (i) the amino acid sequence represented by SEQ ID NO: 1, SEQ ID NO: 3 or SEQ ID NO: 5, wherein at least 1 or 2 amino acids (e.g., approximately 1 to 100 amino acids, preferably approximately 1 to 50 amino acids, preferably approximately 1 to 30 amino acids, more preferably approximately 1 to 10 amino acids, and most preferably several (1 to 5) amino acids) are deleted; (ii) the amino acid sequence represented by SEQ ID NO: 1, SEQ ID NO: 3 or SEQ ID NO: 5, to which at least 1 or 2 amino acids (e.g., approximately 1 to 100 amino acids, preferably approximately 1 to 50 amino acids, preferably approximately 1 to 30 amino acids, more preferably approximately 1 to 10 amino acids, most preferably several (1 to 5) amino acids) are added; (iii) the amino acid sequence represented by SEQ ID NO: 1, SEQ ID NO: 3 or SEQ ID NO: 5, in which at least 1 or 2 amino acids (e.g., approximately 1 to 100 amino acids, preferably approximately 1 to 50 amino acids, more preferably approximately 1 to 30 amino acids, much more preferably approximately 1 to 10 amino acids, and most preferably several (1 to 5) amino acids) are substituted by other amino acids; (iv) the amino acid sequence represented by SEQ ID NO: 1, SEQ ID NO: 3 or SEQ ID NO: 5, in which at least 1 or 2 amino acids (e.g., approximately 1 to 100 amino acids, preferably approximately 1 to 50 amino acids, more preferably approximately 1 to 30 amino acids, much more preferably approximately 1 to 10 amino acids, and most preferably several (1 to 5) amino acids) are inserted; or (v) combination of the amino acid sequences.

Specific examples of the receptor of the present invention include a protein having the amino acid sequence represented by SEQ ID NO: 1, a protein having the amino acid sequence represented by SEQ ID NO: 3, a protein having the amino acid sequence represented by SEQ ID NO: 5, etc.

The partial peptide of the receptor of the present invention (hereinafter sometimes referred to as the partial peptide of the present invention) may be any partial peptide so long as it is the partial peptide which can be used for the methods of screening medicaments later described. Among the protein molecules of the present invention, for example, those having the site exposed to the outside of a cell membrane and retaining substantially the same ligand binding activity, etc. may be employed.

The partial peptide of protein having the amino acid sequence represented by SEQ ID NO: 1, SEQ ID NO: 3 or SEQ ID NO: 5 is a peptide containing the parts analyzed to be extracellular domains (hydrophilic domains) in the hydrophobic plotting analysis. A peptide containing a hydrophobic domain in part can be used as well. In addition, the peptide may contain each domain separately or a plurality of domains together.

In the partial peptides of the present invention, preferred are peptides having at least 20, preferably at least 50, and more preferably at least 100 amino acids, in the amino acid sequence which constitutes the protein of the present invention.

Herein, the term "substantially equivalent activity" is intended to mean the same significance as defined above. The "substantially equivalent activity" can be assayed in the same way as described above.

The partial peptide of the present invention may contain amino acid sequences, (i) of which at least 1 or 2 amino acids (preferably approximately 1 to 10 amino acids, and more preferably several (1 to 5) amino acids) are deleted; (ii) to which at least 1 or 2 amino acids (preferably approximately 1 to 20 amino acids, more preferably approximately 1 to 10 amino acids, and most preferably several (1 to 5) amino acids) are added; or, (iii) in which at least 1 or 2 amino acids (preferably approximately 1 to 10 amino acids, more preferably several and most preferably approximately 1 to 5 amino acids) are substituted by other amino acids.

Specific examples are partial peptides containing the amino acid sequences of 21st to 361st in the amino acid sequence represented by SEQ ID NO: 1, and the like.

The receptor of the present invention and the partial peptide of the present invention are represented in accordance with the conventional way of describing peptides, that is, the N-terminus (amino terminus) at the left hand and the C-terminus (carboxyl terminus) at the right hand. The C-terminus may be in any form of a carboxyl group (—COOH), a carboxylate (—COO—), an amide (—CONH$_2$) and an ester (—COOR).

Herein, examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl such as a phenyl-$C_{1-2}$ alkyl group, e.g., benzyl, phenethyl, etc.; an α-naphthyl-$C_{1-2}$ alkyl group such as α-naphthylmethyl, etc.; pivaloyloxymethyl and the like.

Where the receptor and partial peptide of the present invention contain a carboxyl group (or a carboxylate) at a position other than the C-terminus, the carboxyl group may be amidated or esterified and such an amide or ester is also included within the receptor of the present invention or the partial peptide of the present invention. Examples of the ester group in this case may be the C-terminal esters described above, etc.

Furthermore, examples of the receptor of the present invention and the partial peptide of the present invention include variants wherein the amino group at the N-terminal amino acid residues (e.g., methionine residue) is protected with a protecting group (e.g., a $C_{1-6}$ acyl group such as a $C_{1-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{1-6}$ alkanoyl group, e.g., formyl group, acetyl group, etc.), or conjugated proteins such as glycoproteins having sugar chains; etc.

As salts of the receptor of the present invention or the partial peptide of the present invention, salts with physiologically acceptable acids (e.g., inorganic acids or organic acids) or bases (e.g., alkali metal salts) may be employed, preferably in the form of physiologically acceptable acid addition salts. Examples of such salts include salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

Examples of the ligand capable of binding to a receptor of the present invention (the ligand of the present invention) can be any ligand so long as the ligand binds to the receptor of the present invention. Examples of the ligand are those having a dissociation constant in binding to the receptor of the present invention of 10 μM or less, preferably not greater than 2 μM, more preferably not greater than 1 μM, much more preferably not greater than 200 nM, and most preferably not greater than 100 nM, and the like.

Examples of the ligand of the present invention used are reserpine compounds (e.g., Compound (I), etc.), indole alkaloids, methoctramine compounds (e.g., Compound (II), etc.), and the like. In addition, N-[3-(3-chlorophenoxy)phenyl]-2-methyl-8-[3-(1-piperazinyl)propyl]-5,6,7,8-tetrahydropyrido[2,3-d]pyrimidine-5-amine tetrahydrochloride (EXAMPLE 175 in Japanese Laid-Open Patent Publication (Tokkai) No. 2003-321472) and the like are employed as well.

In the "optionally substituted benzene ring" described above, examples of the "substituent" include a halogen atom (e.g., fluorine, chlorine, bromine, iodine, etc.), $C_{1-3}$ alkylenedioxy (e.g., methylenedioxy, ethylenedioxy, etc.), nitro, cyano, optionally halogenated $C_{1-6}$ alkyl, optionally halogenated $C_{2-6}$ alkenyl, carboxy-$C_{2-6}$ alkenyl (e.g., 2-carboxyethenyl, 2-carboxy-2-methylethenyl, etc.), optionally halogenated $C_{2-6}$ alkynyl, optionally halogenated or optionally condensed $C_{3-8}$ cycloalkyl, $C_{6-14}$ aryl (e.g., phenyl, 1-naphthyl, 2-naphthyl, 2-biphenylyl, 3-biphenylyl, 4-biphenylyl, 2-anthryl, etc.), optionally halogenated $C_{1-8}$ alkoxy, $C_{1-6}$ alkoxy-carbonyl-$C_{1-6}$ alkoxy (e.g., ethoxycarbonylmethyloxy, etc.), $C_{3-8}$ cycloalkyl-oxy (e.g., cyclopropyloxy, cyclopentyloxy, cyclohexyloxy, etc.), hydroxy, $C_{6-14}$ aryloxy (e.g., phenyloxy, 1-naphthyloxy, 2-naphthyloxy, etc.), $C_{7-16}$ aralkyloxy (e.g., benzyloxy, phenethyloxy, etc.), mercapto, optionally halogenated $C_{1-6}$ alkylthio, $C_{6-14}$ arylthio (e.g., phenylthio, 1-naphthylthio, 2-naphthylthio, etc.), $C_{7-16}$ aralkylthio (e.g., benzylthio, phenethylthio, etc.), amino, hydroxyamino, mono-$C_{1-6}$ alkylamino (e.g., methylamino, ethylamino, etc.), mono-$C_{6-14}$ arylamino (e.g., phenylamino, 1-naphthylamino, 2-naphthylamino, etc.), di-$C_{1-6}$ alkylamino (e.g., dimethylamino, diethylamino, ethylmethylamino, etc.), di-$C_{6-14}$ arylamino (e.g., diphenylamino, etc.), nitro, nitrile, formyl, carboxy, $C_{1-6}$ alkyl-carbonyl (e.g., acetyl, propionyl, etc.), $C_{3-8}$ cycloalkyl-carbonyl (e.g., cyclopropylcarbonyl, cyclopentylcarbonyl, cyclohexylcarbonyl, etc.), $C_{1-6}$ alkoxy-carbonyl (e.g., methoxycarbonyl, ethoxycarbonyl, propoxycarbonyl, tert-butoxycarbonyl, etc.), $C_{6-14}$ aryl-carbonyl (e.g., benzoyl, 1-naphthoyl, 2-naphthoyl, etc.), $C_{7-16}$ aralkyl-carbonyl (e.g., phenylacetyl, 3-phenylpropionyl, etc.), $C_{6-14}$ aryloxy-carbonyl (e.g., phenoxycarbonyl, etc.), $C_{7-16}$ aralkyloxy-carbonyl (e.g., benzyloxycarbonyl, phenethyloxycarbonyl, etc.), 5- or 6-membered heterocyclic carbonyl (e.g., nicotinoyl, isonicotinoyl, thenoyl, furoyl, morpholinocarbonyl, thiomorpholinocarbonyl, piperadin-1-ylcarbonyl, pyrrolidin-1-ylcarbonyl, etc.), carbamoyl, mono-$C_{1-6}$ alkyl-carbamoyl (e.g., methylcarbamoyl, ethylcarbamoyl, etc.), di-$C_{1-6}$ alkyl-carbamoyl (e.g., dimethylcarbamoyl, diethylcarbamoyl, ethylmethylcarbamoyl, etc.), $C_{6-14}$ arylcarbamoyl (e.g., phenylcarbamoyl, 1-naphthylcarbamoyl, 2-naphthylcarbamoyl, etc.), $C_{1-6}$ alkoxy-carbamoyl (e.g., methoxycarbamoyl, ethoxycarbamoyl, etc.), 5- or 6-membered heterocyclic carbamoyl (e.g., 2-pyridylcarbamoyl, 3-pyridylcarbamoyl, 4-pyridylcarbamoyl, 2-thienylcarbamoyl, 3-thienylcarbamoyl, etc.), sulfo, $C_{1-6}$ alkylsulfonyl (e.g., methylsulfonyl, ethylsulfonyl, etc.), $C_{6-14}$ arylsulfonyl (e.g., phenylsulfonyl, 1-naphthylsulfonyl, 2-naphthylsulfonyl, etc.), formylamino, $C_{1-6}$ alkyl-carbonylamino (e.g., acetylamino, etc.), $C_{6-14}$ aryl-carbonylamino (e.g., benzoylamino, naphthoylamino, etc.), $C_{1-6}$ alkoxy-carbonylamino (e.g., methoxycarbonylamino, ethoxycarbonylamino, propoxycarbonylamino, butoxycarbonylamino, etc.), $C_{1-6}$ alkylsulfonylamino (e.g., methylsulfonylamino, ethylsulfonylamino, etc.), $C_{6-14}$ arylsulfonylamino (e.g., phenylsulfonylamino, 2-naphthylsulfonylamino, 1-naphthylsulfonylamino, etc.), $C_{1-6}$ alkyl-carbonyloxy (e.g., acetoxy, propionyloxy, etc.), $C_{6-14}$ aryl-carbonyloxy (e.g., benzoyloxy, naphthylcarbonyloxy, etc.), $C_{1-6}$ alkoxy-carbonyloxy (e.g., methoxycarbonyloxy, ethoxycarbonyloxy, propoxycarbonyloxy, butoxycarbonyloxy, etc.), mono-$C_{1-6}$ alkyl-carbamoyloxy (e.g., methylcarbamoyloxy, ethylcarbamoyloxy, etc.), di-$C_{1-6}$ alkyl-carbamoyloxy (e.g., dimethylcarbamoyloxy, diethylcarbamoyloxy, etc.), $C_{6-14}$ aryl-carbamoyloxy (e.g., phenylcarbamoyloxy, naphthylcarbamoyloxy, etc.), 5- or 6-membered heterocyclic carbonyloxy (e.g., nicotinoyloxy, isonicotinoyloxy, etc.), 5-to 7-membered saturated cyclic amino (e.g., pyrrolidin-1-yl, piperidino, piperadin-1-yl, morpholino, thiomorpholino, tetrahydroazepin-1-yl, homopiperadin-1-yl, etc.), 5- to 10-membered aromatic heterocyclic group (e.g., 2-thienyl, 3-thienyl, 2-furyl, 3-furyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl, etc.), 3-to 10-membered non-aromatic heterocyclic group (e.g., 1-azetidinyl, 2-azetidinyl, 3-azetidinyl, 1-pyrrolidinyl, 2-pyrrolidinyl, 3-pyrrolidinyl, 2-imidazolinyl, 4-imidazolinyl, 2-pyrazolidinyl, 3-pyrazolidinyl, 4-pyrazolidinyl, 2-piperidyl, 3-piperidyl, 4-piperidyl, 1-piperazinyl, 2-piperazinyl, morpholino, thiomorpholino, 2-oxiranyl, 2-oxetanyl, 3-oxetanyl, 2-tetrahydrofuranyl, 4-tetrahydropyranyl, etc.), oxo, etc.

The "optionally halogenated $C_{1-6}$ alkyl" described above includes, for example, alkyl (e.g., $C_{1-6}$ alkyl such as methyl, ethyl, propyl, isopropyl, butyl, isobutyl, sec-butyl, tert-butyl, pentyl, hexyl, etc.), which may optionally contain, e.g., 1 to 5, preferably 1 to 3 halogen atoms (e.g., fluorine, chlorine, bromine, iodine, etc.), and the like. Specific examples include methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc.

The "optionally halogenated $C_{2-6}$ alkenyl" described above includes, for example, $C_{2-6}$ alkenyl (e.g., vinyl, propenyl, isopropenyl, 2-buten-1-yl, 4-penten-1-yl, 5-hexen-1-yl, etc.), which may optionally contain, e.g., 1 to 5, preferably 1 to 3 halogen atoms (e.g., fluorine, chlorine, bromine, iodine, etc.), and the like.

The "optionally halogenated $C_{2-6}$ alkynyl" described above includes, for example, $C_{2-6}$ alkynyl (e.g., propargyl, 2-butyn-1-yl, 4-pentyn-1-yl, 5-hexyn-1-yl, etc.), which may optionally contain, e.g., 1 to 5, preferably 1 to 3 halogen atoms (e.g., fluorine, chlorine, bromine, iodine, etc.), and the like.

In the "optionally halogenated or optionally condensed $C_{3-8}$ cycloalkyl" described above, the "optionally halogenated $C_{3-8}$ cycloalkyl" includes, for example, $C_{3-6}$ cycloalkyl (e.g., cyclopropyl, cyclobutyl, cyclopentyl, cyclohexyl, etc.), which may optionally contain, e.g., 1 to 5, preferably 1 to 3 halogen atoms (e.g., fluorine, chlorine, bromine, iodine, etc.), and the like. Specific examples include cyclopropyl, cyclobutyl, cyclopentyl, cyclohexyl, 4,4-dichlorocyclohexyl, 2,2,3,3-tetrafluorocyclopentyl, 4-chlorocyclohexyl, etc.

In the "optionally halogenated or optionally condensed $C_{3-8}$ cycloalkyl" described above, examples of the "condensed $C_{3-8}$ cycloalkyl" include 8- to 14-membered bicyclic or tricyclic $C_{3-8}$ cycloalkyl (e.g., 1-adamantyl, 2-adamantyl, decalin-1-yl, tetralin-1-yl, 9-fluorenyl, 1-indanyl, 1,2,3,4-tetrahydro-1-naphthyl, etc.), etc. The "condensed $C_{3-8}$ cycloalkyl" may optionally be halogenated.

The "optionally halogenated $C_{1-8}$ alkoxy" includes, for example, $C_{1-8}$ alkoxy (e.g., methoxy, ethoxy, propoxy, isopropoxy, butoxy, isobutoxy, sec-butoxy, pentyloxy, hexyloxy, etc.), which may optionally contain, e.g., 1 to 5, preferably 1 to 3 halogen atoms (e.g., fluorine, chlorine, bromine, iodine, etc.), and the like. Specific examples include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, etc.

The "optionally halogenated $C_{1-6}$ alkylthio" described above includes, for example, $C_{1-6}$ alkylthio (e.g., methylthio, ethylthio, propylthio, isopropylthio, butylthio, sec-butylthio, tert-butylthio, etc.), which may optionally contain, e.g., 1 to 5, preferably 1 to 3 halogen atoms (e.g., fluorine, chlorine, bromine, iodine, etc.), and the like. Specific examples include methylthio, difluoromethylthio, trifluoromethylthio, ethylthio, propylthio, isopropylthio, butylthio, 4,4,4-trifluorobutylthio, pentylthio, hexylthio, etc.

The "benzene ring" described above may optionally have, e.g., 1 to 5, preferably 1 to 3, of the substituents described above at substitutable positions. Where the number of substituents is 2 or more, the respective substituents may be the same or different.

In the "optionally substituted 6-membered ring" shown by Ring C, the "substituents" include, for example, the "substituents" in the "optionally substituted benzene ring" shown by Ring A described above, etc.

The "6-membered ring" described above may optionally have, e.g., 1 or 2 of the substituents described above at substitutable positions. Where the number of substituents is 2, the respective substituents may be the same or different.

In the "optionally substituted 5- to 7-membered nitrogen-containing hetero ring" shown by Ring D, examples of the "5- to 7-membered nitrogen-containing hetero ring" include 5- to 7-membered hetero ring containing, e.g., 1 or 2 members and 1 to 4 hetero atoms selected from nitrogen atom, sulfur atom and oxygen atom, in addition to carbon atoms and nitrogen atoms, preferably (i) 5- to 7-membered nitrogen-containing aromatic hetero ring, (ii) 5- to 7-membered nitrogen-containing non-aromatic hetero ring; etc.

Examples of the "5- to 7-membered nitrogen-containing aromatic hetero ring" described above include aromatic hetero rings such as pyrrole, imidazole, pyridine, pyrazine, pyrimidine, pyridazine, etc.

Examples of the "5- to 7-membered nitrogen-containing non-aromatic hetero ring" described above include pyrrolidine, imidazoline, pyrazolidine, pyrazoline, piperidine, piperazine, morpholine, thiomorpholine, etc.

In the "optionally substituted 5- to 7-membered nitrogen-containing hetero ring" shown by Ring D, the "substituent" includes, for example, the "substituent" in the "optionally substituted benzene ring" shown by Ring A above, and the like.

In the "5- to 7-membered nitrogen-containing hetero ring" described above, the substituent described above may optionally have, e.g., 1 to 3, preferably 1 or 2, of the substituents described above at substitutable positions. Where the number of substituents is 2 or more, the respective substituents may be the same or different.

In the "optionally substituted 5- to 7-membered ring" shown by Ring E, the "5- to 7-membered ring" includes, for example, a 5- to 7-membered homocyclic ring, a 5- to 7-membered heterocyclic ring, etc.

Examples of the "5- to 7-membered homocyclic ring" are $C_{5-7}$ cycloalkane (e.g., cyclopentane, cyclohexane, cycloheptane, etc.), $C_{5-7}$ cycloalkene (e.g., cyclopentene, cyclopentadiene, cyclohexene, 1,3-cyclohexadiene, 1,4-cyclohexadiene, cycloheptene, 1,3-cycloheptadiene, etc.), benzene, etc.

The "5- to 7-membered hetero ring" includes, for example, 5- to 7-membered hetero ring containing, e.g., 1 or 2 members and 1 to 4 hetero atoms selected from nitrogen atom, sulfur atom and oxygen atom, in addition to carbon atoms, preferably (i) a 5- to 7-membered aromatic hetero ring, (ii) a 5- to 7-membered non-aromatic hetero ring; etc.

Examples of the "5- to 7-membered aromatic hetero ring" described above are aromatic hetero rings such as thiophene, furan, pyrrole, imidazole, pyrazole, pyridine, pyrazine, pyrimidine, pyridazine, etc.

Examples of the "5- to 7-membered non-aromatic hetero ring" described above are tetrahydrofuran, dihydrofuran, pyran, dioxolane, dioxane, azetidine, pyrrolidine, imidazoline, pyrazolidine, pyrazoline, piperidine, piperazine, morpholine, thiomorpholine, thiazolidine, oxazolidine, oxadiazoline, thiadiazoline, triazoline, 1,4-diazepane, 1,4-oxazepane, 1,4-thiazepane, etc.

Examples of the "5- to 7-membered hetero ring" described above are preferably 5- or 6-membered hetero rings (e.g., thiophene, furan, pyrrole, imidazole, pyrazole, pyridine, pyrazine, pyrimidine, pyridazine, etc.), etc.

In the "optionally substituted 5- or 7-membered ring" shown by Ring E, the "5- or 7-membered ring" may optionally have additional substituents in addition to the group shown by formula below:

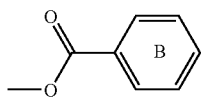

wherein Ring B has the same significance as described above. Examples of such "substituents" include the "substituent" in the optionally substituted benzene ring" shown by Ring A described above.

The "5- to 7-membered ring" described above may optionally have, e.g., 1 to 3, preferably 1 or 2, of the substituents described above at substitutable positions. Where the number of substituents is 2 or more, the respective substituents may be the same or different.

Ring A is preferably a benzene ring which may optionally have $C_{1-8}$ alkoxy.

Ring B is preferably a benzene ring which may optionally have 1 to 3 $C_{1-8}$ alkoxy groups.

Ring C is preferably unsubstituted.

Ring D is preferably piperidine.

Ring E is preferably $C_{5-7}$ cycloalkane which may optionally have 1 or 2 substituents selected from $C_{1-8}$ alkoxy and $C_{1-8}$ alkoxy-carbonyl, in addition to a group represented by formula below:

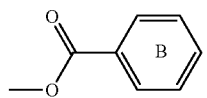

wherein Ring B has the same significance as described above.

Compound (I) is preferably a compound represented by formula below:

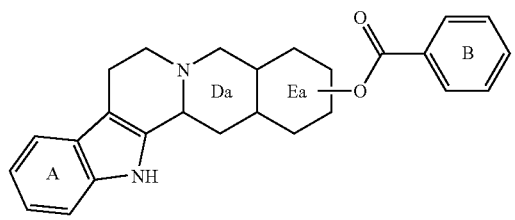

wherein Ring Da is an optionally substituted 6-membered nitrogen-containing hetero ring;
Ring Ea is an optionally substituted 6-membered ring; and,
Ring A and Ring B have the same significance as described above; etc.

More preferably, Compound (I) is reserpine.

The indole alkaloid includes, for example, a *rauwolfia* alkaloid, etc. Specific examples are reserpine, alseroxylon, syrosingopine, rescinnamine, etc. Preferably reserpine is used.

In the "optionally substituted hydrocarbon group" shown by $R^1$ or $R^2$ in Compound (II), examples of the "hydrocarbon group" include a chain or cyclic hydrocarbon group (e.g., alkyl, alkenyl, alkynyl, cycloalkyl, cycloalkenyl, aryl, aralkyl, polycyclic hydrocarbon group, etc.), and the like. Among them, groups having 1 to 19 carbon atoms, etc. are preferred as the chain or cyclic hydrocarbon group.

Examples of the "alkyl" described above include $C_{1-6}$ alkyl (e.g., methyl, ethyl, propyl, isopropyl, butyl, isobutyl, sec-butyl, tert-butyl, pentyl, neopentyl, hexyl, etc.) and the like.

Examples of the "alkenyl" described above include $C_{2-6}$ alkenyl (e.g., vinyl, allyl, isopropenyl, 1-butenyl, 2-butenyl, 3-butenyl, 2-methyl-2-propenyl, 1-methyl-2-propenyl, 2-methyl-1-propenyl, etc.) and the like.

Examples of the "alkynyl" described above include $C_{2-6}$ alkynyl (e.g., ethynyl, propargyl, 1-butynyl, 2-butynyl, 3-butynyl, 1-hexynyl, etc.) and the like.

Examples of the "cycloalkyl" described above include $C_{3-6}$ cycloalkyl (e.g., cyclopropyl, cyclobutyl, cyclopentyl, cyclohexyl, etc.) and the like.

Examples of the "cycloalkenyl" described above include $C_{5-6}$ cycloalkenyl (e.g., cyclopentenyl, 3-cyclopentenyl, 4-cyclopentenyl, 1-cyclohexenyl, 3-cyclohexenyl, 4-cyclohexenyl, etc.) and the like.

Examples of the "aryl" described above include $C_{6-14}$ aryl (e.g., phenyl, 1-naphthyl, 2-naphthyl, 2-biphenylyl, 3-biphenylyl, 4-biphenylyl, 2-anthryl, 3-indenyl, etc.) and the like.

Examples of the "aralkyl" described above include $C_{7-19}$ aralkyl (e.g., benzyl, phenethyl, diphenylmethyl, trityl, 1-naphthylmethyl, 2-diphenylethyl, 2-diphenylethyl, 3-phenylpropyl, 4-phenylbutyl, 5-phenylpentyl, 9-fluorenyl, etc.) and the like.

Examples of the "polycyclic hydrocarbon group" described above include a bi- to tetracyclic non-aromatic hydrocarbon group (e.g., 1-adamantyl, 2-adamantyl, decalin-1-yl, tetralin-1-yl, indan-1-yl, androstan-3-yl, 5-androsten-3-yl, etc.) and the like.

In the "optionally substituted hydrocarbon group" described above, examples of the "substituent" include a halogen atom (e.g., fluorine, chlorine, bromine, iodine, etc.), $C_{1-3}$ alkylenedioxy (e.g., methylenedioxy, ethylenedioxy, etc.), nitro, cyano, optionally halogenated $C_{1-6}$ alkyl, optionally halogenated $C_{2-6}$ alkenyl, carboxy-$C_{2-6}$ alkenyl (e.g., 2-carboxyethenyl, 2-carboxy-2-methylethenyl, etc.), optionally halogenated $C_{2-6}$ alkynyl, optionally halogenated or optionally condensed $C_{3-8}$ cycloalkyl, $C_{6-14}$ aryl (e.g., phenyl, 1-naphthyl, 2-naphthyl, 2-biphenylyl, 3-biphenylyl, 4-biphenylyl, 2-anthryl, etc.), optionally halogenated $C_{1-8}$ alkoxy, $C_{1-6}$ alkoxy-carbonyl-$C_{1-6}$ alkoxy (e.g., ethoxycarbonylmethyloxy, etc.), $C_{3-8}$ cycloalkyl-oxy (e.g., cyclopropyloxy, cyclopentyloxy, cyclohexyloxy, etc.), hydroxy, $C_{6-14}$ aryloxy (e.g., phenyloxy, 1-naphthyloxy, 2-naphthyloxy, etc.), $C_{7-16}$ aralkyloxy (e.g., benzyloxy, phenethyloxy, etc.), mercapto, optionally halogenated $C_{1-6}$ alkylthio, $C_{6-14}$ arylthio (e.g., phenylthio, 1-naphthylthio, 2-naphthylthio, etc.), $C_{7-16}$ aralkylthio (e.g., benzylthio, phenethylthio, etc.), amino, hydroxyamino, mono-$C_{1-6}$ alkylamino (e.g., methylamino, ethylamino, etc.), mono-$C_{6-14}$ arylamino (e.g., phenylamino, 1-naphthylamino, 2-naphthylamino, etc.), di-$C_{1-6}$ alkylamino (e.g., dimethylamino, diethylamino, ethylmethylamino, etc.), di-$C_{6-14}$ arylamino (e.g., diphenylamino, etc.), nitro, nitrile, formyl, carboxy, $C_{1-6}$ alkyl-carbonyl (e.g., acetyl, propionyl, etc.), $C_{3-8}$ cycloalkyl-carbonyl (e.g., cyclopropylcarbonyl, cyclopentylcarbonyl, cyclohexylcarbonyl, etc.), $C_{1-6}$ alkoxy-carbonyl (e.g., methoxycarbonyl, ethoxycarbonyl, propoxycarbonyl, tert-butoxycarbonyl, etc.), $C_{6-14}$ aryl-carbonyl (e.g., benzoyl, 1-naphthoyl, 2-naphthoyl, etc.), $C_{7-16}$ aralkyl-carbonyl (e.g., phenylacetyl, 3-phenylpropionyl, etc.), $C_{6-14}$ aryloxy-carbonyl (e.g., phenoxycarbonyl, etc.), $C_{7-16}$ aralkyloxy-carbonyl (e.g., benzyloxycarbonyl, phenethyloxycarbonyl, etc.), 5- or 6-membered heterocyclic carbonyl (e.g., nicotinoyl, isonicotinoyl, thenoyl, furoyl, morpholinocarbonyl, thiomorpholinocarbonyl, piperadin-1-ylcarbonyl, pyrrolidin-1-ylcarbonyl, etc.), carbamoyl, mono-$C_{1-6}$ alkyl-carbamoyl (e.g., methylcarbamoyl, ethylcarbamoyl, etc.), di-$C_{1-6}$ alkyl-carbamoyl (e.g., dimethylcarbamoyl, diethylcarbamoyl, ethylmethylcarbamoyl, etc.), $C_{6-14}$ aryl-carbamoyl (e.g., phenylcarbamoyl, 1-naphthylcarbamoyl, 2-naphthylcarbamoyl, etc.), $C_{1-6}$ alkoxy-carbamoyl (e.g., methoxycarbamoyl, ethoxycarbamoyl, etc.), 5- or 6-membered heterocyclic carbamoyl (e.g., 2-pyridylcarbamoyl, 3-pyridylcarbamoyl, 4-pyridylcarbamoyl, 2-thienylcarbamoyl, 3-thienylcarbamoyl, etc.), sulfo, $C_{1-6}$ alkylsulfonyl (e.g., methylsulfonyl, ethylsulfonyl, etc.), $C_{6-14}$ arylsulfonyl (e.g., phenylsulfonyl, 1-naphthylsulfonyl, 2-naphthylsulfonyl, etc.), formylamino, $C_{1-6}$ alkyl-carbonylamino (e.g., acetylamino, etc.), $C_{6-14}$ aryl-carbonylamino (e.g., benzoylamino, naphthoylamino, etc.), $C_{1-6}$ alkoxy-carbonylamino (e.g., methoxycarbonylamino, ethoxycarbonylamino, propoxycarbonylamino, butoxycarbonylamino, etc.), $C_{1-6}$ alkylsulfonylamino (e.g., methylsulfonylamino, ethylsulfonylamino, etc.), $C_{6-14}$ arylsulfonylamino (e.g., phenylsulfonylamino, 2-naphthylsulfonylamino, 1-naphthylsulfonylamino, etc.), $C_{1-6}$ alkyl-carbonyloxy (e.g., acetoxy, propionyloxy, etc.), $C_{6-14}$ aryl-carbonyloxy (e.g., benzoyloxy, naphthylcarbonyloxy, etc.), $C_{1-6}$ alkoxy-carbonyloxy (e.g., methoxycarbonyloxy, ethoxycarbonyloxy, propoxycarbonyloxy, butoxycarbonyloxy, etc.), mono-$C_{1-6}$ alkyl-carbamoyloxy (e.g., methylcarbamoyloxy, ethylcarbamoyloxy, etc.), di-$C_{1-6}$ alkyl-carbamoyloxy (e.g., dimethylcarbamoyloxy, diethylcarbamoyloxy, etc.), $C_{6-14}$ aryl-carbamoyloxy (e.g., phenylcarbamoyloxy, naphthylcarbamoyloxy, etc.), 5- or 6-membered heterocyclic carbonyloxy (e.g., nicotinoyloxy, isonicotinoyloxy, etc.), 5-to 7-membered saturated cyclic amino (e.g., pyrrolidin-1-yl, piperidino, piperadin-1-yl, morpholino, thiomorpholino, tetrahydroazepin-1-yl, homopiperadin-1-yl, etc.), a 5- to 10-membered aromatic heterocyclic group (e.g., 2-thienyl, 3-thienyl, 2-furyl, 3-furyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl, etc.), a 3- to 10-membered non-aromatic heterocyclic group (e.g., 1-azetidinyl, 2-azetidinyl, 3-azetidinyl, 1-pyrrolidinyl, 2-pyrrolidinyl, 3-pyrrolidinyl, 2-imidazolinyl, 4-imidazolinyl, 2-pyrazolidinyl, 3-pyrazolidinyl, 4-pyrazolidinyl, 2-piperidyl, 3-piperidyl, 4-piperidyl, 1-piperazinyl, 2-piperazinyl, morpholino, thiomorpholino, 2-oxiranyl, 2-oxetanyl, 3-oxetanyl, 2-tetrahydrofuranyl, 4-tetrahydropyranyl, etc.), oxo, etc.

The "optionally halogenated $C_{1-6}$ alkyl" described above includes, for example, alkyl (e.g., $C_{1-6}$ alkyl such as methyl, ethyl, propyl, isopropyl, butyl, isobutyl, sec-butyl, tert-butyl, pentyl, hexyl, etc.), which may optionally contain, e.g., 1 to 5, preferably 1 to 3 halogen atoms (e.g., fluorine, chlorine, bromine, iodine, etc.), and the like. Specific examples include methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc.

Examples of the "optionally halogenated $C_{2-6}$ alkenyl" described above include $C_{2-6}$ alkenyl (e.g., vinyl, propenyl, isopropenyl, 2-buten-1-yl, 4-penten-1-yl, 5-hexen-1-yl, etc.), which may optionally contain, e.g., 1 to 5, preferably 1 to 3 halogen atoms (e.g., fluorine, chlorine, bromine, iodine, etc.), and the like.

Examples of the "optionally halogenated $C_{2-6}$ alkynyl" described above include $C_{2-6}$ alkynyl (e.g., propargyl, 2-butyn-1-yl, 4-pentyn-1-yl, 5-hexyn-1-yl, etc.), which may optionally contain, e.g., 1 to 5, preferably 1 to 3 halogen atoms (e.g., fluorine, chlorine, bromine, iodine, etc.), and the like.

In the "optionally halogenated or optionally condensed $C_{3-8}$ cycloalkyl" described above, the "optionally halogenated $C_{3-8}$ cycloalkyl" includes, for example, $C_{3-6}$ cycloalkyl (e.g., cyclopropyl, cyclobutyl, cyclopentyl, cyclohexyl, etc.), which may optionally contain, e.g., 1 to 5, preferably 1 to 3 halogen atoms (e.g., fluorine, chlorine, bromine, iodine, etc.), and the like. Specific examples include cyclopropyl, cyclobutyl, cyclopentyl, cyclohexyl, 4,4-dichlorocyclohexyl, 2,2,3,3-tetrafluorocyclopentyl, 4-chlorocyclohexyl, etc.

In the "optionally halogenated or optionally condensed $C_{3-8}$ cycloalkyl" described above, examples of the "condensed $C_{3-8}$ cycloalkyl" include 8- to 14-membered bicyclic or tricyclic $C_{3-8}$ cycloalkyl (e.g., 1-adamantyl, 2-adamantyl, decalin-1-yl, tetralin-1-yl, 9-fluorenyl, 1-indanyl, 1,2,3,4-tetrahydro-1-naphthyl, etc.), etc. The "condensed $C_{3-8}$ cycloalkyl" may optionally be halogenated.

The "optionally halogenated $C_{1-8}$ alkoxy" includes, for example, $C_{1-8}$ alkoxy (e.g., methoxy, ethoxy, propoxy, isopropoxy, butoxy, isobutoxy, sec-butoxy, pentyloxy, hexyloxy, etc.), which may optionally contain, e.g., 1 to 5, preferably 1 to 3 halogen atoms (e.g., fluorine, chlorine, bromine, iodine, etc.), and the like. Specific examples include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, etc.

The "optionally halogenated $C_{1-6}$ alkylthio" described above includes, for example, $C_{1-6}$ alkylthio (e.g., methylthio, ethylthio, propylthio, isopropylthio, butylthio, sec-butylthio, tert-butylthio, etc.), which may optionally contain, e.g., 1 to 5, preferably 1 to 3 halogen atoms (e.g., fluorine, chlorine, bromine, iodine, etc.), and the like. Specific examples include methylthio, difluoromethylthio, trifluoromethylthio, ethylthio, propylthio, isopropylthio, butylthio, 4,4,4-trifluorobutylthio, pentylthio, hexylthio, etc.

The "hydrocarbon group" described above may optionally have, e.g., 1 to 5, preferably 1 to 3, of the substituents described above at substitutable positions. Where the number of substituents is 2 or more, the respective substituents may be the same or different.

The spacer shown by X is a spacer having 1 to 24 atoms in the main chain. Examples of the spacer include a bivalent chain hydrocarbon group optionally intervened by 1 to 4 groups selected from —NH—, —O—, —S—, —SO— and —$SO_2$— [e.g., a bivalent $C_{1-24}$ chain hydrocarbon group (e.g., alkylene, alkenylene, alkylene, etc.) or a bivalent 3- to 8-membered cyclic group [e.g., a bivalent 6-membered cyclic group (e.g., 1,2-phenylene, 1,3-phenylene, 1,4-phenylene, cyclohexane-1,4-diyl, pyridine-2,5-diyl, pyridine-2,4-diyl, piperidine-1,4-diyl, etc.) and the like], etc.

$R^1$ and $R^2$ are preferably alkyl, more preferably $C_{1-6}$ alkyl.

X is preferably a bivalent $C_{1-24}$ chain hydrocarbon group optionally intervened by 1 to 4 groups selected from —NH— and —S—, more preferably —$(CH_2)_6$—NH—$(CH_2)_8$—NH—$(CH_2)_6$—, —$(CH_2)_6$—NH—$(CH_2)_2$—S—S—$(CH_2)_2$—NH—$(CH_2)_6$—, etc.

Specific examples of Compound (II) include methoctramine [wherein $R^1$: methyl, $R^2$: methyl, X: —$(CH_2)_6$—NH—$(CH_2)_8$—NH—$(CH_2)_6$—], benextramine [wherein $R^1$: methyl, $R^2$: methyl, X: —$(CH_2)_6$—NH—$(CH_2)_2$—S—S—$(CH_2)_2$—NH—$(CH_2)_6$—], etc.

The salts of compounds represented by formula (I) or (II) include, for example, metal salts, ammonium salts, salts with organic bases, salts with inorganic acids, salts with organic acids, salts with basic or acidic amino acids, etc. Preferred examples of the metal salts are alkali metal salts such as sodium salts, potassium salts, etc.; alkaline earth metal salts such as calcium salts, magnesium salts, barium salts, etc.; aluminum salts, etc. Preferred examples of the salts with organic bases are trimethylamine, triethylamine, pyridine, picoline, 2,6-lutidine, ethanolamine, diethanolamine, triethanolamine, cyclohexylamine, dicyclohexylamine, N, N'-dibenzylethylenediamine, etc. Preferred examples of the salts with inorganic acids are salts with hydrochloric acid, hydrobromic acid, nitric acid, sulfuric acid, phosphoric acid, etc. Preferred examples of the salts with organic acids are salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, etc. Preferred examples of the salts with basic amino acids are salts with arginine, lysine, ornithine, etc. and preferred examples of the salts with acidic amino acids are salts with aspartic acid, glutamic acid, etc.

Among them, pharmaceutically acceptable salts are preferable. For example, when the compound has an acidic functional group, inorganic salts such as alkali metal salts (e.g., sodium salt, potassium salt, etc.), alkaline earth metal salts (e.g., calcium salt, magnesium salt, barium salt, etc.), ammonium salts, etc. are preferable. When the compound has a basic functional group, salts with inorganic acids with hydrochloric acid, hydrobromic acid, nitric acid, sulfuric acid, phosphoric acid, etc., and salts with organic acids such as acetic acid, phthalic acid, fumaric acid, oxalic acid, tartaric acid, maleic acid, citric acid, succinic acid, methanesulfonic acid, p-toluenesulfonic acid, etc. are preferable.

Labeled ligand is also included in the ligand of the present invention.

Examples of the labeling agent available for the assay method using the labeling substance are radioisotopes (e.g., [$^{125}$I], [$^{131}$I], [$^{3}$H], [$^{14}$C], [$^{32}$P], [$^{33}$P], [$^{35}$S], etc.), fluorescent substances (e.g., cyanine fluorescent substances [e.g., Cy2, Cy3, Cy5, Cy5.5, Cy7 (Amersham Biosciences)), fluorescamine, fluorescein isothiocyanate, NBD (7-nitrobenz-2-oxa-1,3-diazol), etc.], enzymes (e.g., β-galactosidase, β-glucosidase, alkaline phosphatase, peroxidase, malate dehydrogenase), luminescent substances (e.g., luminol, luminal derivatives, luciferin, lucigenin), biotin, lanthanide elements, etc. Among them, radioisotopes [$^{3}$H] is preferred.

The receptor of the present invention and the partial peptide of the present invention can be manufactured from the aforesaid human or warm-blooded animal cells or tissues by publicly known methods for purification of polypeptides, or can also be manufactured by culturing transformants transformed by DNAs encoding the polypeptides. In addition, they can also be manufactured by modifications of peptide synthesis. For example, the receptor and partial peptide can also be manufactured by the methods described in, e.g., Genomics, 56, 12-21, 1999, Biochim. Biophys. Acta, 1446, 57-70, 1999, etc., or by modifications of these methods.

Where the receptor and partial peptide of the present invention are manufactured from human or mammalian tissues or cells, human or mammalian tissues or cells are homogenized, then extracted with an acid or the like, and the extract is isolated and purified by a combination of chromatography techniques such as reverse phase chromatography, ion exchange chromatography, and the like.

To synthesize the receptor of the present invention or partial peptides or salts thereof, commercially available resins that are used for polypeptide synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl acetamidomethyl resin, polyacrylamide resin, 4-(2',4'-dimethoxyphenylhydroxymethyl)phenoxy resin, 4-(2',4'-dimethoxyphenyl-Fmoc-aminoethyl)phenoxy resin, etc. Using these resins, amino acids in which α-amino groups and functional groups on the side chains are appropriately protected are condensed on the resin in the order of the sequence of the objective polypeptide according to various condensation methods publicly known in the art. At the end of the reaction, the polypeptide is cut out from the resin and at the same time, the protecting groups are removed. Then, intramolecular disulfide bond-forming reaction is performed in a highly diluted solution to obtain the objective polypeptide, receptor, partial peptide or its amides.

For condensation of the protected amino acids described above, a variety of activation reagents for polypeptide synthesis may be used, and carbodiimides are particularly preferable. Examples of such carbodiimides include DCC, N,N'-diisopropylcarbodiimide, N-ethyl-N'-(3-dimethylaminoprolyl)carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use to activate the protected amino acids or condense with the resin may be chosen from solvents known to be usable for polypeptide condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxane, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to polypeptide binding reactions and is usually selected in the range of approximately −20° C. to 50° C. The activated amino acid derivatives are used generally in an excess of 1.5 to 4 times. The condensation is examined by a test using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole.

Examples of the protecting groups used to protect the amino groups of the starting compounds include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (in the form of linear, branched or cyclic alkyl esters of the alkyl moiety such as methyl, ethyl, propyl, butyl, t-butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower ($C_{1-6}$) alkanoyl group, such as acetyl group, an aroyl group such as benzoyl group, and a group derived from carbonic acid such as benzyloxycarbonyl group, ethoxycarbonyl group, etc. Examples of a group appropriately used for the etherification include benzyl group, tetrahydropyranyl group, t-butyl group, etc.

Examples of groups for protecting the phenolic hydroxyl group of tyrosine include Bzl, $Cl_2$-Bzl, 2-nitrobenzyl, Br-Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups used in the starting compounds include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)], etc. As the activated amino acids, in which the amino groups are activated in the starting material, for example, the corresponding phosphoric amides are employed.

To eliminate (split off) the protecting groups, there are used catalytic reduction under hydrogen gas flow in the presence of a catalyst such as Pd-black, Pd-carbon, etc.; an acid treatment with anhydrous hydrogen fluoride, methanesulfonic acid, trifluoromethane-sulfonic acid or trifluoroacetic acid, or a mixture solution of these acids; a treatment with a base such as diisopropylethylamine, triethylamine, piperidine, piperazine, etc.; and reduction with sodium in liquid ammonia. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol, 1,2-ethanedithiol, etc. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol, 1,4-butanedithiol, etc. as well as by a treatment with an alkali such as a dilute sodium hydroxide solution, dilute ammonia, etc.

Protection of the functional groups that should not be involved in the reaction of the starting materials, protecting groups, elimination of the protecting groups, activation of functional groups involved in the reaction, or the like may be appropriately chosen from publicly known groups and publicly known means.

In another method for obtaining the receptor or partial peptide of the present invention, for example, the α-carboxyl group of the carboxy terminal amino acid is first protected by amidation; the peptide (polypeptide) chain is then extended from the amino group side to a desired length. Thereafter, a polypeptide in which only the protecting group of the N-terminal α-amino group in the peptide chain has been eliminated from the polypeptide and a polypeptide in which only the protecting group of the C-terminal carboxyl group has been eliminated are prepared. The two polypeptides are condensed in a mixture of the solvents described above. The details of the condensation reaction are the same as described above. After the protected polypeptide obtained by the condensation is purified, all the protecting groups are eliminated by the method described above to give the desired crude polypeptide. This crude polypeptide is purified by various known purification means. Lyophilization of the major fraction gives the amide of the desired receptor or its partial peptide.

To prepare the esterified receptor of the present invention or partial peptides or salts thereof, for example, the α-carboxyl group of the carboxy terminal amino acid is condensed with a desired alcohol to prepare the amino acid ester, which is followed by procedures similar to the preparation of the amidated receptor or partial peptide above to give the desired esterified receptor or partial peptide.

The receptor or partial peptide of the present invention can be manufactured by publicly known methods for peptide synthesis, or by cleaving the receptor with an appropriate peptidase. For the methods for peptide synthesis, for example, either solid phase synthesis or liquid phase synthesis may be used. That is, the partial peptide or amino acids that can constitute the receptor or partial peptide of the present invention are condensed with the remaining part. Where the product contains protecting groups, these protecting groups are removed to give the desired peptide. Publicly known methods for condensation and elimination of the protecting groups are described in (i)-(v) below.

(i) M. Bodanszky & M. A. Ondetti: Peptide Synthesis, Interscience Publishers, New York (1966)
(ii) Schroeder & Luebke: The Peptide, Academic Press, New York (1965)
(iii) Nobuo Izumiya, et al.: Peptide Gosei-no-Kiso to Jikken (Basics and experiments of peptide synthesis), published by Maruzen Co. (1975)
(iv) Haruaki Yajima & Shunpei Sakakibara: Seikagaku Jikken Koza (Biochemical Experiment) 1, Tanpakushitsu no Kagaku (Chemistry of Proteins) IV, 205 (1977)

(v) Haruaki Yajima, ed.: Zoku Iyakuhin no Kaihatsu (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography and recrystallization to give the receptor or partial peptide of the present invention. When the receptor or partial peptide obtained by the above methods is in a free form, the receptor or partial peptide can be converted into an appropriate salt by a publicly known method or its modification; conversely when the receptor or partial peptide is obtained in a salt form, it can be converted into a free form or other different salt form by a publicly known method or its modifications.

The polynucleotide encoding the receptor or partial peptide of the present invention may be any polynucleotide so long as it contains the base sequence encoding the receptor or partial peptide of the present invention described above. Preferably, the polynucleotide is a DNA. The DNA may also be any one of genomic DNA, genomic DNA library, cDNA derived from the cells or tissues described above, cDNA library derived from the cells or tissues described above and synthetic DNA.

The vector used for the library may be any of bacteriophage, plasmid, cosmid, phagemid and the like. In addition, the DNA can be amplified by reverse transcriptase polymerase chain reaction (hereinafter abbreviated as RT-PCR) with total RNA or mRNA fraction prepared from the above-described cells or tissues.

The DNA encoding the receptor of the present invention may be any one of, for example, a DNA containing the base sequence represented by SEQ ID NO: 2, SEQ ID NO:4 or SEQ ID NO: 6, or any DNA containing a base sequence hybridizable to the base sequence represented by SEQ ID NO: 2, SEQ ID NO:4 or SEQ ID NO: 6 under high stringent conditions and encoding the receptor which has the properties of substantially equivalent to those of the protein containing the amino acid sequence represented by SEQ ID NO: 1, SEQ ID NO: 3 or SEQ ID NO: 5.

Examples of the DNA that is hybridizable to the base sequence represented by SEQ ID NO: 2, SEQ ID NO:4 or SEQ ID NO: 6 under high stringent conditions include DNAs having at least about 60% homology, preferably at least about 70% homology, more preferably at least about 80% homology, more preferably at least about 90% homology, much more preferably at least about 95% homology, to the base sequence represented by SEQ ID NO: 2, SEQ ID NO:4 or SEQ ID NO: 6; and the like.

The hybridization can be carried out by publicly known methods or by a modification thereof, for example, according to the method described in Molecular Cloning, 2nd. (J. Sambrook et al., Cold Spring Harbor Lab. Press, 1989). A commercially available library can also be used according to the instructions of the attached manufacturer's protocol. The hybridization can be carried out preferably under high stringent conditions.

The high stringent conditions used herein are, for example, those in a sodium concentration at about 19 to 40 mM, preferably about 19 to 20 mM at a temperature of about 50 to 70° C., preferably about 60 to 65° C. In particular, hybridization conditions in a sodium concentration at about 19 mM at a temperature of about 65° C. are most preferred.

More specifically, as the DNA encoding the receptor containing the amino acid sequence represented by SEQ ID NO: 1, there may be employed a DNA containing the base sequence represented by SEQ ID NO: 2, etc., as the DNA encoding the receptor containing the amino acid sequence represented by SEQ ID NO: 3, there may be employed a DNA containing the base sequence represented by SEQ ID NO: 4, etc., as the DNA encoding the receptor containing the amino acid sequence represented by SEQ ID NO: 5, there may be employed a DNA containing the base sequence represented by SEQ ID NO: 6, etc.

As the DNA encoding the partial peptide of the present invention may be any DNA so long as it contains the base sequence encoding the partial peptide of the receptor of the present invention. The DNA may also be any one of genomic DNA, genomic DNA library, cDNA derived from the cells or tissues described above, cDNA library derived from the cells or tissues described above and synthetic DNA. Specifically as the DNA encoding the partial peptide of the present invention, there are employed, for example, a DNA having a part of the base sequence of a DNA having the base sequence represented by SEQ ID NO: 2, SEQ ID NO: 4 or SEQ ID NO:6, or a DNA having a base sequence hybridizable to the base sequence represented by SEQ ID NO: 2, SEQ ID NO: 4 or SEQ ID NO:6 under high stringent conditions and containing a part of DNA encoding the receptor having the activities substantially equivalent to those of the protein containing the amino acid sequence represented by SEQ ID NO: 1, SEQ ID NO: 3 or SEQ ID NO: 5, and so on.

The DNA hybridizable to the base sequence represented by SEQ ID NO: 2, SEQ ID NO: 4 or SEQ ID NO:6 has the same significance as described above.

Methods for the hybridization and the high stringent conditions that can be used are the same as those described above.

The polynucleotide (e.g., DNA) encoding the receptor or partial peptide of the present invention may be labeled by methods public known. The labeled agents include radioisotopes, fluorescent substances (e.g., fluorescein, etc.), luminescent substances, enzymes, biotin, lanthanides, or the like.

For cloning of DNAs that completely encode the receptor or partial peptide of the present invention, the DNA can be either amplified by PCR using synthetic DNA primers containing a part of the base sequence of the receptor or partial peptide of the present invention, or the DNA inserted into an appropriate vector can be selected by hybridization with a labeled DNA fragment or synthetic DNA that encodes a part or entire region of the receptor or partial peptide of the present invention. The hybridization can be carried out, for example, according to the method described in Molecular Cloning, 2nd (J. Sambrook et al., Cold Spring Harbor Lab. Press, 1989). Where the hybridization is carried out using commercially available library, the procedures may be conducted in accordance with the protocol described in the attached instructions.

Conversion of the base sequence of DNA can be effected by publicly known methods such as the ODA-LA PCR method, the Gapped duplex method, the Kunkel method, etc., or its modification, using a publicly known kit available as Mutan™-super Express Km (manufactured by Takara Shuzo Co., Ltd.) or Mutan™-K (manufactured by Takara Shuzo Co., Ltd.), etc.

The cloned DNA encoding the receptor can be used as it is, depending upon purpose or, if desired, after digestion with a restriction enzyme or after addition of a linker thereto. The DNA may contain ATG as a translation initiation codon at the 5' end thereof and TAA, TGA or TAG as a translation termination codon at the 3' end thereof. These translation initiation and termination codons may also be added by using an appropriate synthetic DNA adapter.

The expression vector for the receptor or partial peptide of the present invention can be manufactured, for example, by (a) excising the desired DNA fragment from the DNA encoding the receptor or partial peptide of the present invention, and then (b) ligating the DNA fragment with an appropriate expression vector downstream a promoter in the vector.

Examples of the vector include plasmids derived form *E. coli* (e.g., pBR322, pBR325, pUC12, pUC13), plasmids derived from *Bacillus subtilis* (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1-11, pXT1, pRc/CMV, pRc/RSV, pcDNA I/Neo, etc.

The promoter used in the present invention may be any promoter if it matches well with a host to be used for gene expression. In the case of using animal cells as the host, examples of the promoter include SRα promoter, SV40 promoter, LTR promoter, CMV promoter, HSV-TK promoter, etc.

Among them, it is preferred to use CMV (cytomegalovirus) promoter, SRα promoter, etc. Where the host is bacteria of the genus *Escherichia*, preferred examples of the promoter include trp promoter, lac promoter, recA promoter, $\lambda P_L$ promoter, lpp promoter, T7 promoter, etc. In the case of using bacteria of the genus *Bacillus* as the host, preferred example of the promoter are SPO1 promoter, SPO2 promoter, penP promoter, etc. When yeast is used as the host, preferred examples of the promoter are PHO5 promoter, PGK promoter, GAP promoter, ADH promoter, etc. When insect cells are used as the host, preferred examples of the promoter include polyhedrin prompter, P10 promoter, etc.

In addition to the foregoing examples, the expression vector may further optionally contain an enhancer, a splicing signal, a poly A addition signal, a selection marker, SV40 replication origin (hereinafter sometimes abbreviated as SV40ori), etc. Examples of the selection marker include dihydrofolate reductase (hereinafter sometimes abbreviated as dhfr) gene [methotrexate (MTX) resistance], ampicillin resistant gene (hereinafter sometimes abbreviated as $Amp^r$), neomycin resistant gene (hereinafter sometimes abbreviated as $Neo^r$, G418 resistance), etc. In particular, when dhfr gene is used as the selection marker using dhfr gene-deficient Chinese hamster cells, selection can also be made on a thymidine free medium.

If necessary, a signal sequence that matches with a host is added to the N-terminus of the receptor of the present invention. Examples of the signal sequence that can be used are PhoA signal sequence, OmpA signal sequence, etc. when bacteria of the genus *Escherichia* is used as the host; α-amylase signal sequence, subtilisin signal sequence, etc. when bacteria of the genus *Bacillus* is used as the host; MFα signal sequence, SUC2 signal sequence, etc. when yeast is used as the host; and insulin signal sequence, α-interferon signal sequence, antibody molecule signal sequence, etc. when animal cells are used as the host, respectively.

Using the vector containing the DNA encoding the receptor or partial peptide of the present invention thus constructed, transformants can be manufactured.

Examples of the host, which may be employed, are bacteria belonging to the genus *Escherichia*, bacteria belonging to the genus *Bacillus*, yeast, insect cells, insects, animal cells, etc.

Specific examples of the bacteria belonging to the genus *Escherichia* include *Escherichia coli* K12 DH1 [Proc. Natl. Acad. Sci. U.S.A., 60, 160 (1968)], JM103 [Nucleic Acids Research, 9, 309 (1981)], JA221 [Journal of Molecular Biology, 120, 517 (1978)], HB101 [Journal of Molecular Biology, 41, 459 (1969)], C600 [Genetics, 39, 440 (1954)], etc.

Examples of the bacteria belonging to the genus *Bacillus* include *Bacillus subtilis* MI114 [Gene, 24, 255 (1983)], 207-21 [Journal of Biochemistry, 95, 87 (1984)], etc.

Examples of yeast include *Saccharomyces cereviseae* AH22, AH22R⁻, NA87-11A, DKD-5D, 20B-12, *Schizosaccharomyces pombe* NCYC1913, NCYC2036, *Pichia pastoris* KM71, etc.

Examples of insect cells include, for the virus AcNPV, *Spodoptera frugiperda* cell (Sf cell), MG1 cell derived from mid-intestine of *Trichoplusia ni*, High Five™ cell derived from egg of *Trichoplusia ni*, cells derived from *Mamestra brassicae*, cells derived from Estigmena acrea, etc.; and for the virus BmNPV, *Bombyx mori* N cell (BnN cell), etc. is used. Examples of the Sf cell which can be used are Sf9 cell (ATCC CRL 1711), Sf21 cell (both cells are described in Vaughn, J. L. et al., In Vivo, 13, 213-217 (1977)), etc.

As the insect, for example, a larva of *Bombyx mori* can be used [Maeda et al., Nature, 315, 592 (1985)].

Examples of animal cells include monkey cell COS-7, Vero, Chinese hamster cell CHO (hereinafter referred to as CHO cell), dhfr gene-deficient Chinese hamster cell CHO (hereinafter simply referred to as CHO (dhfr⁻) cell), mouse L cell, mouse AtT-20, mouse myeloma cell, mouse ATDC5 cell, rat GH3, human FL cell, etc.

Bacteria belonging to the genus *Escherichia* can be transformed, for example, by the method described in Proc. Natl. Acad. Sci. U.S.A., 69, 2110 (1972), Gene, 17, 107 (1982), etc.

Bacteria belonging to the genus *Bacillus* can be transformed, for example, by the method described in Molecular & General Genetics, 168, 111 (1979), etc.

Yeast can be transformed, for example, by the method described in Methods in Enzymology, 194, 182-187 (1991), Proc. Natl. Acad. Sci. U.S.A., 75, 1929 (1978), etc.

Insect cells or insects can be transformed, for example, according to the method described in Bio/Technology, 6, 47-55 (1988), etc.

Animal cells can be transformed, for example, according to the method described in Saibo Kogaku (Cell Engineering), extra issue 8, Shin Saibo Kogaku Jikken Protocol (New Cell Engineering Experimental Protocol), 263-267 (1995) (published by Shujunsha), or Virology, 52, 456 (1973).

Thus, the transformants transformed with the expression vectors containing the DNAs encoding the receptor or partial peptide can be obtained.

Where the host is bacteria belonging to the genus *Escherichia* or the genus *Bacillus*, the transformant can be appropriately cultured in a liquid medium, which contains materials required for growth of the transformant such as carbon sources, nitrogen sources, inorganic materials, and the like. Examples of the carbon sources include glucose, dextrin, soluble starch, sucrose, etc.; examples of the nitrogen sources include inorganic or organic materials such as ammonium salts, nitrate salts, corn steep liquor, peptone, casein, meat extract, soybean cake, potato extract, etc.; and, examples of the inorganic materials are calcium chloride, sodium dihydrogenphosphate, magnesium chloride, etc. In addition, yeast extracts, vitamins, growth promoting factors etc. may also be added to the medium. Preferably, pH of the medium is adjusted to about 5 to about 8.

A preferred example of the medium for culturing the bacteria belonging to the genus *Escherichia* is M9 medium supplemented with glucose and Casamino acids [Miller, Journal of Experiments in Molecular Genetics, 431-433, Cold Spring Harbor Laboratory, New York, 1972]. If necessary, a chemical such as 3β-indolylacrylic acid can be added to the medium thereby to activate the promoter efficiently.

Where the bacteria belonging to the genus *Escherichia* are used as the host, the transformant is usually cultivated at about 15 to 43° C. for about 3 to 24 hours. If necessary, the culture may be aerated or agitated.

Where the bacteria belonging to the genus *Bacillus* are used as the host, the transformant is cultured generally at about 30 to 40° C. for about 6 to 24 hours. If necessary, the culture can be aerated or agitated.

Where yeast is used as the host, the transformant is cultivated, for example, in Burkholder's minimal medium [Bostian, K. L. et al., Proc. Natl. Acad. Sci. U.S.A., 77, 4505 (1980)] or in SD medium supplemented with 0.5% Casamino acids [Bitter, G. A. et al., Proc. Natl. Acad. Sci. U.S.A., 81, 5330 (1984)]. Preferably, pH of the medium is adjusted to about 5 to 8. In general, the transformant is cultivated at about 20 to 35° C. for about 24 to 72 hours. If necessary, the culture can be aerated or agitated.

Where insect cells or insects are used as the host, the transformant is cultivated in, for example, Grace's Insect Medium (Grace, T. C. C., Nature, 195, 788 (1962)) to which an appropriate additive such as immobilized 10% bovine serum is added. Preferably, pH of the medium is adjusted to about 6.2 to about 6.4. Normally, the transformant is cultivated at about 27° C. for about 3 days to about 5 days and, if necessary, the culture can be aerated or agitated.

Where animal cells are employed the host, the transformant is cultured in, for example, MEM medium containing about 5 to 20% fetal bovine serum [Science, 122, 501 (1952)], DMEM medium [Virology, 8, 396 (1959)], RPMI 1640 medium [The Journal of the American Medical Association, 199, 519 (1967)], 199 medium [Proceeding of the Society for the Biological Medicine, 73, 1 (1950)], etc. Preferably, pH of the medium is adjusted to about 6 to about 8. The transformant is usually cultivated at about 30° C. to about 40° C. for about 15 to 60 hours and, if necessary, the culture can be aerated or agitated.

As described above, the receptor or partial peptide of the present invention can be produced in the transformant, in the cell membrane of the transformant, or outside of the transformant.

The receptor or partial peptide of the present invention can be separated and purified from the culture described above by the following procedures.

When the receptor or partial peptide of the present invention is extracted from the bacteria or cells, the bacteria or cell is collected after culturing by a publicly known method and suspended in an appropriate buffer. The bacteria or cell is then disrupted by publicly known methods such as ultrasonication, a treatment with lysozyme and/or freeze-thaw cycling, followed by centrifugation, filtration, etc to produce crude extract of the polypeptide. Thus, the crude extract of the protein can be obtained. The buffer may contain a protein modifier such as urea or guanidine hydrochloride, or a surfactant such as Triton X-100™, etc. When the polypeptide is secreted in the culture broth, the supernatant can be separated, after completion of the cultivation, from the bacteria or cell to collect the supernatant by a publicly known method.

The receptor or partial peptide contained in the supernatant or the extract thus obtained can be purified by appropriately combining the publicly known methods for separation and purification. Such publicly known methods for separation and purification include a method utilizing difference in solubility such as salting out, solvent precipitation, etc.; a method mainly utilizing difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis; and the like.

When the receptor or partial peptide thus obtained is in a free form, the receptor or partial peptide can be converted into the salt by publicly known methods or modifications thereof. On the other hand, when the receptor or partial peptide is obtained in the form of a salt, it can be converted into the free form or in the form of a different salt by publicly known methods or modifications thereof.

The receptor or partial peptide produced by the recombinant can be treated, prior to or after the purification, with an appropriate protein-modifying enzyme so that the receptor or partial peptide can be appropriately modified to partially remove the polypeptide. Examples of the protein-modifying enzyme include trypsin, chymotrypsin, arginyl endopeptidase, protein kinase, glycosidase and the like.

The ligand capable of specifically binding to the receptor of the present invention can be used as it is when commercially available, or can be extracted or manufactured by publicly known methods or its modifications.

The antibodies to the protein comprising the same or substantially the same amino acid sequence as the amino acid sequence represented by SEQ ID NO: 1, its partial peptide or a salt thereof (hereinafter sometimes collectively referred to as the antibody of the present invention) may be any of polyclonal and monoclonal antibodies, as long as they are capable of recognizing the receptor of the present invention. The antibodies to the receptor of the present invention include the antibodies that inactivate the signal transduction of the receptor, antibodies that activate the signal transduction of the receptor, etc.

The antibodies to the receptor of the present invention can be produced by a publicly known method of producing an antibody or antiserum, using the receptor of the present invention as an antigen.

[Preparation of Monoclonal Antibody]

(a) Preparation of Monoclonal Antibody-producing Cells

The receptor of the present invention is administered to warm-blooded animals either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once every about 2 to about 6 weeks and about 2 to about 10 times in total. Examples of the applicable warm-blooded animals are monkeys, rabbits, dogs, guinea pigs, mice, rats, sheep, goats and fowl, with the use of mice and rats being preferred.

In the preparation of monoclonal antibody-producing cells, a warm-blooded animal, e.g., mouse, immunized with an antigen wherein the antibody titer is noted is selected, then spleen or lymph node is collected after 2 to 5 days from the final immunization and antibody-producing cells contained therein are fused with myeloma cells from homozoic or heterozoic animal to give monoclonal antibody-producing hybridomas. Measurement of the antibody titer in antisera may be carried out, for example, by reacting a labeled polypeptide, which will be described later, with the antiserum followed by assaying the binding activity of the labeling agent bound to the antibody. The fusion may be carried out, for example, by the known method by Koehler and Milstein [Nature, 256, 495, (1975)]. Examples of the fusion accelerator are polyethylene glycol (PEG), Sendai virus, etc., of which PEG is preferably employed.

Examples of the myeloma cells are those collected from warm-blooded animals such as NS-1, P3U1, SP2/0, AP-1, etc. In particular, P3U1 is preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by incubation at 20 to 40° C., preferably at 30 to 37° C. for 1 to 10 minutes, an efficient cell fusion can be carried out.

Various methods can be used for screening of monoclonal antibody-producing hybridomas. Examples of such methods include a method which comprises adding the supernatant of a hybridoma to a solid phase (e.g., a microplate) adsorbed with the polypeptide (protein) as an antigen directly or together with a carrier, adding an anti-immunoglobulin antibody (where mouse cells are used for the cell fusion, anti-mouse immunoglobulin antibody is used) labeled with a radioactive substance or an enzyme or Protein A and detecting the monoclonal antibody bound to the solid phase, and a method which comprises adding the supernatant of hybridoma to a solid phase adsorbed with an anti-immunoglobulin antibody or Protein A, adding the polypeptide labeled with a radioactive substance or an enzyme and detecting the monoclonal antibody bound to the solid phase, or the like.

The monoclonal antibody can be screened according to publicly known methods or their modifications. In general, the screening can be performed in a medium for animal cells supplemented with HAT (hypoxanthine, aminopterin and thymidine). Any screening and growth medium can be employed as far as the hybridoma can grow there. For example, RPMI 1640 medium containing 1 to 20%, preferably 10 to 20% fetal bovine serum, GIT medium (Wako Pure Chemical Industries, Ltd.) containing 1 to 10% fetal bovine serum, a serum free medium for cultivation of a hybridoma (SFM-101, Nissui Seiyaku Co., Ltd.) and the like, can be used for the screening and growth medium. The culture is carried out generally at 20 to 40° C., preferably at 37° C., for about 5 days to about 3 weeks, preferably 1 to 2 weeks, normally in 5% $CO_2$. The antibody titer of the culture supernatant of a hybridoma can be determined as in the assay for the antibody titer in antisera described above.

(b) Purification of Monoclonal Antibody

Separation and purification of a monoclonal antibody can be carried out by publicly known methods, such as separation and purification of immunoglobulins [for example, salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A or Protein G and dissociating the binding to obtain the antibody.]

[Preparation of Polyclonal Antibody]

The polyclonal antibody of the present invention can be manufactured by publicly known methods or modifications thereof. For example, a warm-blooded animal is immunized with an immunogen (polypeptide antigen) per se, or a complex of immunogen and a carrier protein is formed and the animal is immunized with the complex in a manner similar to the method described above for the manufacture of monoclonal antibodies. The product containing the antibody to the receptor of the present invention is collected from the immunized animal followed by separation and purification of the antibody.

In the complex of immunogen and carrier protein used to immunize a warm-blooded animal, the type of carrier protein and the mixing ratio of carrier to hapten may be any type and in any ratio, as long as the antibody is efficiently produced to the hapten immunized by crosslinking to the carrier. For example, bovine serum albumin, bovine thyroglobulin or hemocyanin is coupled to hapten in a carrier-to-hapten weight ratio of approximately 0.1 to 20, preferably about 1 to 5.

A variety of condensation agents can be used for the coupling of carrier to hapten. Glutaraldehyde, carbodiimide, maleimide activated ester and activated ester reagents containing thiol group or dithiopyridyl group are used for the coupling.

The condensation product is administered to warm-blooded animals either solely or together with carriers or diluents to the site that can produce the antibody by the administration. In order to potentiate the antibody productivity upon the administration, complete Freund's adjuvant or incomplete Freund's adjuvant may be administered. The administration is usually made once every about 2 to 6 weeks and about 3 to 10 times in total.

The polyclonal antibody can be collected from the blood, ascites, etc., preferably from the blood of warm-blooded animal immunized by the method described above.

The polyclonal antibody titer in antiserum can be assayed by the same procedure as that for the determination of serum antibody titer described above. The separation and purification of the polyclonal antibody can be carried out, following the method for the separation and purification of immunoglobulins performed as in the separation and purification of monoclonal antibodies described hereinabove.

The polynucleotide (e.g., DNA) containing a complementary or substantially complementary base sequence to the polynucleotide (e.g., DNA) or a part thereof encoding the protein containing the same or substantially the same amino acid sequences as the amino acid sequence represented by SEQ ID NO: 1, as its partial peptide or as its salt can be any polynucleotide (antisense polynucleotide), so long as it contains a base sequence complementary or substantially complementary to the polynucleotide, or a part of the base sequence and capable of suppressing expression of the polynucleotide.

Specific examples of the polynucleotide include antisense DNAs (hereinafter these DNAs are sometimes simply referred to as the antisense DNA of the present invention) having a base sequence complementary or substantially complementary to polynucleotides (e.g., DNAs) encoding the receptor of the present invention (hereinafter these DNAs are sometimes briefly referred to as the DNA of the present invention) or a part of the base sequence, and can be any antisense DNA, so long as it contains the complementary or substantially complementary base sequence to the DNA of the present invention, or a part of the base sequence and capable of suppressing expression of the DNA.

The base sequence substantially complementary to the DNA of the present invention may include, for example, a base sequence having at least about 70% homology, preferably at least about 80% homology, more preferably at least about 90% homology and most preferably at least about 95% homology, to the entire base sequence or its partial base sequence of the base sequence complementary to the DNA of the present invention (i.e., complementary strand to the DNA of the present invention), and the like. Especially in the entire base sequence of the complementary strand to the DNA of the present invention, preferred are an antisense DNA having at least about 70% homology, preferably at least about 80% homology, more preferably at least about 90% homology and most preferably at least about 95% homology, to the complementary strand of the base sequence which encodes the N-terminal region of the receptor of the present invention (e.g., the base sequence around the initiation codon). These antisense DNAs can be prepared using publicly known DNA synthesizer.

Specific examples include an antisense polynucleotide containing the entire or part of a base sequence complementary or substantially complementary to a base sequence of DNA containing the base sequence represented by SEQ ID NO: 2, SEQ ID NO: 4 or SEQ ID NO: 6, antisense polynucleotide containing the entire or part of a base sequence complementary or substantially complementary to a base sequence of DNA containing the base sequence represented by SEQ ID NO: 2, SEQ ID NO: 4 or SEQ ID NO: 6, etc., preferably an antisense polynucleotide containing the entire or part of a base sequence complementary to a base sequence of DNA containing the base sequence represented by SEQ ID NO: 2, SEQ ID NO: 4 or SEQ ID NO: 6, an antisense polynucleotide containing the entire or part of a base sequence complementary to a base sequence of DNA containing the base sequence represented by SEQ ID NO: 2, SEQ ID NO: 4 or SEQ ID NO: 6, etc.

The antisense polynucleotide is generally constituted by bases of about 10 to about 40, preferably about 15 to about 30.

To prevent digestion with a hydrolase such as nuclease, etc., the phosphoric acid residue (phosphate) of each nucleotide that constitutes the antisense DNA may be substituted with chemically modified phosphoric acid residues, e.g., phosphorothioate, methyl phosphonate, phosphorodithionate, etc. These antisense polynucleotides may be synthesized using a publicly known DNA synthesizer, etc.

According to the present invention, the antisense polynucleotide capable of inhibiting the replication or expression of a gene for the receptor of the present invention (nucleic acid) can be designed and synthesized based on the base sequence information of cloned or identified protein-encoding DNA. Such a polynucleotide (nucleic acid) is hybridizable to RNA of a gene for the receptor of the present invention to inhibit the synthesis or function of said RNA or is capable of modulating and/or controlling the expression of a gene for the receptor of the present invention via interaction with RNA associated with the receptor of the present invention. Polynucleotides complementary to the selected sequences of RNA associated with the receptor of the present invention and polynucleotides specifically hybridizable to RNA associated with the receptor of the present invention are useful in modulating and/or controlling the in vivo and in vitro expression of the receptor gene of the present invention, and are useful for the treatment or diagnosis of diseases, etc. The term "corresponding" is used to mean homologous to or complementary to a particular sequence of the nucleotide including the gene, base sequence or nucleic acid. The term "corresponding" between nucleotides, base sequences or nucleic acids and peptides (proteins) usually refer to amino acids of a peptide (protein) under the order derived from the sequence of nucleotides (nucleic acids) or their complements. In the protein genes, the 5' end hairpin loop, 5' end 6-base-pair repeats, 5' end untranslated region, protein translation initiation codon, protein coding region, ORF translation termination codon, 3' end untranslated region, 3' end palindrome region, and 3' end hairpin loop, may be selected as preferred target regions, though any other region may be selected as a target in the protein genes.

The relationship between the targeted nucleic acids and the polynucleotides complementary to at least a part of the target region, specifically the relationship between the target nucleic acids and the polynucleotides hybridizable to the target region, can be denoted to be "antisense." Examples of the antisense polynucleotides include polynucleotides containing 2-deoxy-D-ribose, polynucleotides containing D-ribose, any other type of polynucleotides which are N-glycosides of a purine or pyrimidine base, or other polymers containing non-nucleotide backbones (e.g., commercially available protein nucleic acids and synthetic sequence-specific nucleic acid polymers) or other polymers containing nonstandard linkages (provided that the polymers contain nucleotides having such a configuration that allows base pairing or base stacking, as is found in DNA or RNA), etc. The antisense polynucleotides may be double-stranded DNA, single-stranded DNA, double-stranded RNA, single-stranded RNA or a DNA:RNA hybrid, and may further include unmodified polynucleotides (or unmodified oligonucleotides), those with publicly known types of modifications, for example, those with labels known in the art, those with caps, methylated polynucleotides, those with substitution of one or more naturally occurring nucleotides by their analogue, those with intramolecular modifications of nucleotides such as those with uncharged linkages (e.g., methyl phosphonates, phosphotriesters, phosphoramidates, carbamates, etc.) and those with charged linkages or sulfur-containing linkages (e.g., phosphorothioates, phosphorodithioates, etc.), those having side chain groups such as proteins (nucleases, nuclease inhibitors, toxins, antibodies, signal peptides, poly-L-lysine, etc.), saccharides (e.g., monosaccharides, etc.), those with intercalators (e.g., acridine, psoralen, etc.), those containing chelators (e.g., metals, radioactive metals, boron, oxidative metals, etc.), those containing alkylating agents, those with modified linkages (e.g., a anomeric nucleic acids, etc.), and the like. Herein the terms "nucleoside", "nucleotide" and "nucleic acid" are used to refer to moieties that contain not only the purine and pyrimidine bases, but also other heterocyclic bases, which have been modified. Such modifications may include methylated purines and pyrimidines, acylated purines and pyrimidines and other hetero rings. Modified nucleotides and modified nucleotides also include modifications on the sugar moiety, wherein, for example, one or more hydroxyl groups may optionally be substituted with a halogen atom(s), an aliphatic group(s), etc., or may be converted into the corresponding functional groups such as ethers, amines, or the like.

The antisense polynucleotide (nucleic acid) of the present invention is RNA, DNA or a modified nucleic acid (RNA, DNA). Specific examples of the modified nucleic acid are, but not limited to, sulfur and thiophosphate derivatives of nucleic acids and those resistant to degradation of polynucleoside amides or oligonucleoside amides. The antisense nucleotide of the present invention can be modified preferably based on the following design, that is, by increasing the intracellular stability of the antisense nucleotide, enhancing the cell permeability of the antisense nucleotide, increasing the affinity of the nucleic acid to the targeted sense strand to a higher level, or minimizing the toxicity, if any, of the antisense nucleotide.

Many of such modifications are known in the art, as disclosed in J. Kawakami, et al., Pharm. Tech. Japan, Vol. 8, pp. 247, 1992; Vol. 8, pp. 395, 1992; S. T. Crooke, et al. ed., Antisense Research and Applications, CRC Press, 1993; etc.

The antisense polynucleotide of the present invention may contain altered or modified sugars, bases or linkages. The antisense polynucleotide may also be provided in a specialized form such as liposomes, microspheres, or may be applied to gene therapy, or may be provided in combination with attached moieties. Such attached moieties include polycations such as polylysine that act as charge neutralizers of the phosphate backbone, or hydrophobic moieties such as lipids (e.g., phospholipids, cholesterols, etc.) that enhance the interaction with cell membranes or increase uptake of the nucleic acid. Preferred examples of the lipids to be attached are cholesterols or derivatives thereof (e.g., cholesteryl chloroformate, cholic acid, etc.). These moieties may be attached to the nucleic acid at the 3' or 5' ends thereof and may also be attached thereto through a base, sugar, or intramolecular nucleoside linkage. Other moieties may be capping groups specifically placed at the 3' or 5' ends of the nucleic acid to prevent degradation by nucleases such as exonuclease, RNase, etc. Such capping groups include, but are not limited to, hydroxyl protecting groups known in the art, including glycols such as polyethylene glycol, tetraethylene glycol and the like.

The inhibitory action of the antisense nucleotide can be examined using the transformant of the present invention, the gene expression system of the present invention in vivo and in vitro, or the translation system for the receptor of the present invention in vivo and in vitro. The nucleic acid can be applied to cells by a variety of publicly known methods.

Hereinafter, (i) the receptor of the present invention, (ii) the polynucleotide encoding the receptor of the present invention (the polynucleotide of the present invention), (iii) the antibody to the receptor of the present invention (the antibody of the present invention) (iv) the antisense polynucleotide of the receptor of the present invention (e.g., the antisense DNA of the present invention), (v) the ligand capable of specifically binding to the receptor of the present invention (the ligand of the present invention), etc. are described in terms of their applications.

[1] Screening of Drug Candidate Compounds for Disease

By using the receptor of the present invention or the ligand-receptor assay system using the expression system of the receptor of the present invention in its recombinant form, compounds (e.g., peptides, proteins, antibodies, non-peptide compounds, synthetic compounds, fermentation products, cell extracts, plant extracts, animal tissue extracts, blood plasma, etc.) or salts thereof that change the binding properties of the receptor of the present invention to the ligand of the present invention can be efficiently screened.

The compounds or salts thereof include (i) compounds having the cell stimulating activities (for example, the activities that promote arachidonic acid release, acetylcholine release, intracellular $Ca^{2+}$ release, intracellular cAMP production, intracellular cAMP production suppression, intracellular cGMP production, inositol phosphate production, change in cell membrane potential, phosphorylation of intracellular proteins, activation of c-fos, pH reduction, GTPγS binding activity, activation of cAMP-dependent protein kinase, activation of cGMP-dependent protein kinase, activation of phospholipid-dependent protein kinase, activation of mitogen-activated protein phosphorylase (MAP kinase), increased expression of serum responsive factor gene, etc., receptor internalization activity, etc.) mediated by the receptor of the present invention (agonists), (ii) compounds that do not have the cell-stimulating activities (antagonists), (iii) compounds that promote the binding properties of the receptor of the present invention to the ligand of the present invention, (iv) compounds that inhibit the binding properties of the receptor of the present invention to the ligand of the present invention, and the like.

Specifically, comparison is made between (i) the case where the ligand of the present invention is brought in contact with the receptor of the present invention and (ii) the case where the ligand of the present invention and a test compound are brought in contact with the receptor of the present invention. The comparison is made by assaying, for example, the binding amounts of the ligand of the present invention to the receptor of the present invention, the cell stimulating activities, or the like.

Specific examples of the screening method of the present invention include:

(a) a method of screening a compound or its salt that changes the binding properties of the ligand of the present invention to the receptor of the present invention, which comprises measuring the binding amounts of the ligand of the present invention to the receptor of the present invention in the case of contacting the ligand of the present invention with the receptor of the present invention and in the case of contacting the ligand of the present invention and a test compound with the receptor of the present invention; and comparing the binding amounts;

(b) a method of screening a compound or its salt that changes the binding amounts of the ligand of the present invention to the receptor of the present invention, which comprises assaying the binding amounts of the ligand of the present invention to a cell containing the receptor of the present invention or a membrane fraction of the cell, in the case of contacting the ligand of the present invention with the cell containing the receptor of the present invention or the membrane fraction of the cell and in the case of contacting the ligand of the present invention and a test compound with the cell or its cell membrane fraction, and comparing the binding amounts; and, (c) the screening method according to (b) described above, where the receptor of the present invention is the receptor of the present invention expressed on a cell membrane by culturing a transformant containing a DNA encoding the receptor of the present invention;

(d) the receptor-binding assay system such as the screening method described in (a) to (c) above, wherein the ligand of the present invention is a labeled ligand;

(e) a method of screening a compound or its salt that changes the binding properties of the ligand of the present invention to the receptor of the present invention, which comprises assaying the cell stimulating activities mediated by the receptor of the present invention, in the case of contacting the ligand of the present invention with the receptor of the present invention and in the case of contacting the ligand of the present invention and a test compound with the receptor of the present invention; and comparing the activities;

(f) a method of screening a compound or its salt that changes the binding properties of the ligand of the present invention to the receptor of the present invention, which comprises assaying the cell stimulating activities mediated by the receptor of the present invention, in the case of contacting the ligand of the present invention with a cell containing the receptor of the present invention or a membrane fraction of the cell, and in the case of contacting the ligand of the present invention and a test compound with the cell containing the receptor of the present invention or its cell membrane fraction; and comparing the activities; and, (g) the screening method according to (f) described above, where the receptor of the present invention is the receptor of the present invention expressed on a cell membrane by culturing a transformant containing a DNA encoding the receptor of the present invention; etc.

The screening method of the present invention will be specifically described below.

As the receptor of the present invention, membrane fractions from human or warm-blooded animal organs are preferably employed. However, it is very difficult to obtain human-derived organs among others, and the receptor of the present invention, etc. expressed abundantly by use of recombinants are suitable for use in the screening.

To produce the receptor of the present invention, the aforesaid methods, etc. are applied.

When cells containing the receptor of the present invention or membrane fractions of these cells are employed in the screening methods of the present invention, these cells or membrane fractions may be prepared following the procedures later described.

Where cells containing the receptor of the present invention are employed, the cells may be fixed using glutaraldehyde, formalin, etc. The fixation can be made by publicly known methods.

The cells containing the receptor of the present invention refer to host cells where the receptor of the present invention is expressed, and such host cells include *Escherichia coli*, *Bacillus subtilis*, yeast, insect cells, animal cells, etc. described above. The host cells can be prepared in a manner similar to the method described above.

The cell membrane fraction is used to mean a fraction abundant in cell membrane obtained by cell disruption and subsequent fractionation by publicly known methods. The cell disruption methods include cell squashing using a Potter-Elvehjem homogenizer, disruption using a Waring blender or Polytron (manufactured by Kinematica Inc.), disruption by ultrasonication, disruption by cell spraying through thin nozzles under an increased pressure using a French press, and the like. Cell membrane fractionation is effected mainly by fractionation using a centrifugal force, such as fractional centrifugation, density gradient centrifugation, etc. For example, cell disruption fluid is centrifuged at a low speed (500 rpm to 3,000 rpm) for a short period of time (normally about 1 to about 10 minutes), the resulting supernatant is then centrifuged at a higher speed (15,000 rpm to 30,000 rpm) normally for 30 minutes to 2 hours. The precipitate thus obtained is used as the membrane fraction. The membrane fraction is rich in the receptor of the present invention expressed and membrane components such as cell-derived phospholipids, membrane proteins, etc.

The amount of the receptor of the present invention in the cells or cell membrane fractions containing the receptor of the present invention is preferably $10^3$ to $10^8$ molecules, more preferably $10^5$ to $10^7$ molecules, per cell. As the amount of expression increases, the ligand binding activity per unit of the membrane fraction (specific activity) increases so that not only the highly sensitive screening system can be constructed but also large quantities of samples can be assayed on the same lot.

To perform the screening methods such as the receptor-binding assay system, the cell stimulating assay system and the like, for example, a fraction of the receptor of the present invention and a labeled form of the ligand of the present invention (e.g., a labeled form of the ligand of the present invention), etc. are employed. For the fraction of the receptor of the present invention, a fraction from naturally occurring type of the receptor of the present invention or a fraction from recombinant type of the receptor of the present invention having an activity equivalent thereto, or the like, are desirable. Herein, the equivalent activity is used to mean an equivalent ligand binding activity, etc. As the labeled ligands, there may be used ligands labeled with, e.g., radioisotope (e.g., [$^3$H], [$^{125}$I], [$^{14}$C], [$^{32}$P], [$^{33}$P], [$^{35}$S], etc.), fluorescent substances (e.g., cyanine fluorescent substances [e.g., Cy2, Cy3, Cy5, Cy5.5, Cy7 (Amersham Biosciences)), fluorescamine, fluorescein isothiocyanate, NBD (7-nitrobenz-2-oxa-1,3-diazol), etc.], enzymes (e.g., β-galactosidase, β-glucosidase, alkaline phosphatase, peroxidase, malate dehydrogenase), luminescent substances (e.g., luminol, luminal derivatives, luciferin, lucigenin), biotin, lanthanide elements, or the like.

Specifically, screening of the compound that changes the binding properties of the ligand of the present invention to the receptor of the present invention can be performed by the following procedures. First, a receptor preparation is prepared by suspending cells containing the receptor of the present invention or their membrane fractions in a buffer appropriate for screening. Any buffer can be used so long as it does not interfere with ligand-receptor binding, such buffer including a phosphate buffer, a Tris-HCl buffer, etc. having pH of 4 to 10 (desirably pH of 6 to 8). For the purpose of minimizing non-specific binding, a surfactant such as CHAPS, Tween-80™ (manufactured by Kao-Atlas Inc.), digitonin, deoxycholate, etc. may be added to the buffer. Further for the purpose of suppressing degradation of the receptor of the present invention by a protease, a protease inhibitor such as PMSF, leupeptin, E-64 (manufactured by Peptide Institute, Inc.), pepstatin, etc. may also be added. A given quantity (5,000 cpm to 500,000 cpm) of a labeled form of the ligand of the present invention is added to 0.01 ml to 10 ml of the receptor solution, and at the same time, $10^{-10}$ to $10^{-7}$ M of a test compound is allowed to be co-present. To determine the amount of non-specific binding (NSB), a reaction tube containing a large excess of the ligand of the present invention in an unlabeled form is also provided. The reaction is carried out at 0° C. to 50° C., preferably about 4° C. to 37° C. for 20 minutes to 24 hours, preferably 30 minutes to 3 hours. After completion of the reaction, the reaction mixture is filtrated through glass fiber filter paper, etc. and washed with an appropriate volume of the same buffer. The residual radioactivity in the glass fiber filter paper is then measured by means of a liquid scintillation counter or a γ-counter. When the nonspecific binding (NSB) is subtracted from the count ($B_0$) when any antagonizing compound is absent and the thus obtained count ($B_0$–NSB) is made 100%, a test compound having the specific binding (B–NSB) of, e.g., 50% or less, can be selected as a compound that decreases the binding properties of the ligand of the present invention to the receptor of the present invention. In addition, the compounds which bind to the receptor of the present invention can also be screened by utilizing the surface plasmon sensor technique.

Specifically, the receptor of the present invention is immobilized on the sensor chip surface of Biacore 3000 (Biacore, Inc.), and then the solution of a test compound in phosphate-buffered saline (PBS), etc. is applied onto the chip surface. By monitoring the changes on the surface plasmon, the test compound bound to the receptor of the present invention is screened. For example, the test compound, which gives the measurement data of 5 resonance units or more in the changes at the surface plasmon, is screened as a substance having the binding properties to the receptor of the present invention.

To perform the screening methods of the cell stimulating assay system described above, the cell-stimulating activities mediated by the receptor of the present invention (e.g., the activity that promotes or suppresses arachidonic acid release, acetylcholine release, intracellular $Ca^{2+}$ release, intracellular cAMP production, intracellular cAMP production suppression intracellular cGMP production, inositol phosphate production, change in cell membrane potential, phosphorylation of intracellular proteins, activation of c-fos, pH reduction, GTPγS binding activity, activation of cAMP-dependent protein kinase, activation of cGMP-dependent protein kinase, activation of phospholipid-dependent protein kinase, activation of mitogen-activated protein kinase (MAP kinase), activities that promote increased expression of serum responsive factor gene, etc., receptor internalization activity, etc.)

may be assayed by publicly known methods, or using assay kits commercially available. Specifically, the cells containing the receptor of the present invention are first cultured on a multi-well plate, etc. Prior to screening, the medium is replaced with a fresh medium or with an appropriate non-cytotoxic buffer, and a test compound or the like is added thereto, followed by culturing for a given period of time. Subsequently, the cells are extracted or the supernatant is recovered and the resulting product is quantified by the respective methods. Where it is difficult to detect the production of an indicator substance for the cell stimulating activities (e.g., arachidonic acid, etc.) due to a degrading enzyme contained in the cells, an inhibitor against such a degrading enzyme may be added prior to the assay. For detecting activities such as the cAMP production suppressing activity, the baseline production in the cells is increased by forskolin or the like and the suppressing effect on the increased baseline production can be detected.

To perform the screening by assaying the cell stimulating activities, cells in which an appropriate form of the receptor of the present invention is expressed are required. As the cells where the receptor of the present invention is expressed, an aforesaid cell line where the receptor of the present invention is expressed, etc. are desirable.

Examples of the test compound include peptides, proteins, antibodies, non-peptide compounds, synthetic compounds, fermentation products, cell extracts, plant extracts, animal tissue extracts, blood plasma, and the like.

In more detail, the screening methods of the cell stimulating assay system described above are described in (1) to (14) below.

(1) When the receptor-expressed cells are stimulated by the receptor agonist, G protein in the cells is activated and GTP binds thereto. This phenomenon is observed as well in a membrane fraction of the receptor-expression cells. Usually, GTP is hydrolyzed and changes to GDP; when GTPγS is previously added to the reaction solution, GTPγS binds to G protein as GTP does, but does not undergo hydrolysis so that the state bound to the G protein-containing cell membrane is maintained. When labeled GTPγS is used, the cell stimulating activities of the receptor agonist-expressed cell can be assayed by determining the labeled GTPγS remained on the cell membrane.

Utilizing this reaction, the compound that changes the binding properties of the ligand of the present invention to the receptor of the present invention can be screened by assaying the stimulating activities of the ligand of the present invention on the cells where the receptor of the present invention is expressed.

This method is carried out using the membrane fraction containing the receptor of the present invention. In this assay method, the substance showing the activity of promoting the binding of GTPγS to the membrane fraction containing the receptor of the present invention is an agonist.

Specifically, the compound that changes the binding properties of the ligand of the present invention to the receptor of the present invention can be screened by assaying the GTPγS binding promoting activities on the membrane fraction containing the receptor of the present invention in the presence of labeled GTPγS, in the case of contacting the ligand of the present invention with the membrane fraction containing the receptor of the present invention and in the case of contacting the ligand of the present invention and a test compound with the membrane fraction containing the receptor of the present invention; and comparing the activities.

In this method, the test compound showing the activity of suppressing the GTPγS binding promoting activity by the ligand of the present invention to the membrane fraction containing the receptor of the present invention can be selected as an antagonist candidate compound.

On the other hand, when a test compound alone is brought into contact with the cell membrane fraction of the receptor of the present invention, the agonist can be screened as well by assaying the GTPγS binding-promoting activities in the cell membrane fraction containing the receptor of the present invention.

A specific example of the screening method is described below.

The membrane fraction containing the receptor of the present invention, which is prepared by a modification of publicly known methods, is diluted with a buffer for membrane dilution (50 mM Tris, 5 mM $MgCl_2$, 150 mM NaCl, 1 μM GDP, 0.1% BSA, pH 7.4). A degree of dilution varies depending upon the amount of a receptor expressed. The dilution is dispensed by 0.2 ml each in Falcon 2053, to which the ligand of the present invention or the ligand of the present invention and a test compound is/are added, and [$^{35}$S]GTPγS is further added to the mixture in a final concentration of 200 μM. After maintaining at 25° C. for an hour, 1.5 ml of ice-cooled wash buffer (50 mM Tris, 5 mM $MgCl_2$, 150 mM NaCl, 0.1% BSA, 0.05% CHAPS, pH 7.4) is added to the mixture followed by filtration through a glass fiber filter paper GF/F. After keeping at 65° C. for 30 minutes, the mixture is dried and the radioactivity of [$^{35}$S] GTPγS bound to the membrane fraction remained on the filter paper is measured with a liquid scintillation counter. When the radioactivity in the experimental zone added with the ligand of the present invention alone is defined as 100% and the radioactivity in the experimental zone not added with the ligand of the present invention is defined as 0%, an effect of the test compound on the GTPγS binding promoting activity by the ligand of the present invention is worked out. The test compound showing the GTPγS binding promoting activity of, for example, 50% or less can be selected as an antagonist candidate compound.

(2) In the cells where the receptor of the present invention is expressed, the intracellular cAMP production is promoted by stimulation of the ligand of the present invention. Utilizing this reaction, the compound that changes the binding properties of the ligand of the present invention to the receptor of the present invention can be screened by assaying the stimulating activities of the ligand of the present invention on the cells where the receptor of the present invention is expressed.

Specifically, the compound that changes the binding properties of the ligand of the present invention to the receptor of the present invention can be screened by assaying intracellular cAMP production promoting activities on the cells, in the case of contacting the ligand of the present invention with the cells where the receptor of the present invention is expressed and in the case of contacting the ligand of the present invention and a test compound with the cells where the receptor of the present invention is expressed; and comparing the activities.

The amount of cAMP produced in the cells where the receptor of the present invention is expressed can be assayed by the RIA system using an anti-cAMP antibody, whose antibody is obtained from immunized mouse, rat, rabbit, goat, bovine, etc., and [$^{125}$I]-labeled cAMP (both commercially available) or by the EIA system using an anti-cAMP antibody and labeled cAMP in combination. Quantification by the SPA (Scintillation Proximity Assay) method is also available, using beads, which contain scintillants bearing anti-cAMP antibodies immobilized using protein A or antibodies to IgG, etc. of animal used to produce the anti-cAMP antibodies, and [$^{125}$I]-labeled cAMP. Quantification can also be conducted by a competitive method cAMP detection kit (Perkin Elmer). The kit utilizes AlphaScreen (Perkin Elmer), which is the chemically amplified luminescent proximity homogeneous assay system.

In this method, the test compound showing the activity of inhibiting the cAMP production promoting activity by the ligand of the present invention against the cells wherein the protein of the present invention is expressed can be selected as an antagonist candidate compound.

On the other hand, when a test compound alone is brought into contact with the cells where the receptor of the present invention is expressed, a compound showing an agonist activity can be screened by inspecting the cAMP production promoting activity.

A specific example of the screening method is described below.

The cells where the receptor of the present invention is expressed (e.g., animal cells such as CHO cells, etc.) are plated on a 24-well plate in $5\times10^4$ cells/well followed by cultivation for 48 hours. The cells are washed with Hanks' buffer (pH 7.4) containing 0.2 mM 3-isobutyl-methylxanthine, 0.05% BSA and 20 mM HEPES (hereinafter simply referred to as a reaction buffer). Thereafter, 0.5 ml of the reaction buffer is added to the cells and the mixture is kept warm in the medium for 30 minutes. The reaction buffer is removed and 0.25 ml of a fresh reaction buffer is added to the cells. Then, 0.25 ml of the reaction buffer containing 10 µM of the ligand of the present invention or 10 µM of the ligand of the present invention and a test compound is added to the cells, followed by reacting at 37° C. for 24 minutes. The reaction is terminated by adding 100 µl of 20% perchloric acid. The reaction mixture is then put on ice for an hour to extract intracellular cAMP. The amount of cAMP in the extract is measured using a cAMP EIA kit (Amersham Pharmacia Biotech). Taking the amount of cAMP promoted by addition of 10 µM of the ligand of the present invention as 100%, an effect of the test compound on the cAMP production promoting activity by the ligand of the present invention is calculated comparing with the amount of cAMP of adding the reaction buffer alone. The test compound that inhibits the activity of the ligand of the present invention to increase the cAMP production promoting activity, e.g., to 50% or less, can be selected as an antagonist candidate compound.

On the other hand, when the ligand of the present invention and a test compound are brought in contact with the cell where the receptor of the present invention is expressed or when a test compound alone is brought in contact with the cell where the receptor of the present invention is expressed, a compound showing an inverse agonist activity can be screened by monitoring the cAMP production suppressing activity. In addition, when the intracellular cAMP production suppressing activity is assayed, a substance (e.g., forskolin, the ligand of the present invention, etc.) that increases the cAMP level is added in the screening method to increase the intracellular cAMP level as a base level, and the detection of the activity becomes easy.

(3) The compound that changes the binding properties of the ligand of the present invention to the receptor of the present invention can be screened by assaying the stimulating activities of the ligand of the present invention on the cell where the receptor of the present invention is expressed, using a CRE-reporter gene vector.

A DNA containing CRE (cAMP response element) is inserted into a vector upstream the reporter gene to acquire CRE-reporter gene vector. In the CRE-reporter gene vector-transfected cells where the receptor of the present invention is expressed, stimulation accompanied by increased cAMP induces expression of the reporter gene mediated by CRE and subsequent production of the gene product (protein) of the reporter gene. That is, changes in the amount of cAMP in the CRE-reporter gene vector-transfected cells can be detected by assaying the enzyme activity of the reporter gene protein.

Specifically, the compound that changes the binding properties of the ligand of the present invention to the receptor of the present invention can be screened by assaying the enzyme activities of the reporter gene protein on the cells in the presence of a substance capable of increasing the intracellular cAMP level, in the case of contacting the ligand of the present invention with the CRE-reporter gene vector-transfected cells where the receptor of the present invention is expressed and in the case of contacting the ligand of the present invention and a test compound with the CRE-reporter gene vector-transfected cells where the receptor of the present invention is expressed; and comparing the activities.

As the vector, there may be employed, e.g., PicaGene Basic Vector, PicaGene Enhancer Vector (Toyo Ink Mfg. Co., Ltd.), and the like. A CRE-containing DNA is inserted into the vector described above at the multicloning site upstream the reporter gene, e.g., luciferase gene, which is made a CRE-reporter gene vector.

In this method, the test compound which suppresses the enzyme activity promotion of the reporter gene protein by the ligand of the present invention can be selected as an antagonist candidate compound.

On the other hand, the agonist can be screened as well by contacting a test compound alone with the cell where the receptor of the present invention is expressed and assaying the promoting activities similar to the ligand of the present invention.

Taking as an example in which luciferase is used as a reporter gene, a specific example of this screening method is described below.

The CRE-reporter gene (luciferase)-transfected cells where the receptor of the present invention is expressed are plated on a 24-well plate in $5\times10^3$ cells/well followed by cultivation for 48 hours. The cells are washed with Hanks' balanced salt solution (pH 7.4) containing 0.2 mM 3 isobutyl-methylxanthine, 0.05% BSA and 20 mM HEPES (hereinafter merely referred to as a reaction buffer). Thereafter, 0.5 ml of the reaction buffer is added to the cells and the mixture is kept warm in the medium for 30 minutes. The reaction buffer is removed and 0.25 ml of a fresh reaction buffer is added to the cells. Then, 0.25 ml of the reaction buffer supplemented with 10 µM of the ligand of the present invention or 10 µM of the ligand of the present invention and a test compound is added to the cells. The reaction is then carried out at 37° C. for 24 minutes. The cells are dissolved in a cell lysis agent for PicaGene (Toyo Ink Mfg. Co., Ltd.) and a luminescent substrate (Toyo Ink Mfg. Co., Ltd.) is added to the lysate. Luminescence by luciferase is measured with a luminometer, a liquid scintillation counter or a top counter. The levels of luminescence by luciferase are measured when only the ligand of the present invention is added and when 10 µM of the ligand of the present invention and a test compound are added, and compared therebetween.

The ligand of the present invention promotes the increase of luminescence level by luciferase. The compound that suppresses the promotion can be selected as an antagonist candidate compound.

As the reporter gene, there may be employed genes, e.g., alkaline phosphatase, chloramphenicol acetyltransferase, β-galactosidase, etc. The enzyme activities of these reporter gene proteins are assayed in accordance with methods publicly know, or using commercially available assay kits. The alkaline phosphatase activity can be assayed by using, e.g., Lumi-Phos 530 manufactured by Wako Pure Chemical Industries, Ltd.; the chloramphenicol acetyltransferase activity by using, e.g., FAST CAT chloramphenicol Acetyltransferase Assay Kit manufactured by Wako Pure Chemical Industries, Ltd.; and the β-galactosidase activity by using, e.g., Aurora Gal-XE manufactured by Wako Pure Chemical Industries, Ltd.

(4) The compound that changes the binding properties of the ligand of the present invention to the receptor of the present invention can be screened by assaying the stimulating activities of the ligand of the present invention on the cell where the receptor of the present invention is expressed, using a SRE-reporter gene vector.

A DNA containing SRE (serum response element) is inserted into a vector upstream its reporter gene to acquire the SRE-reporter gene vector. In the SRE-reporter gene vector-transfected cells where the receptor of the present invention is expressed, activation of proliferative signals such as MAP kinase activity in response to serum stimulation, etc. induces expression of the reporter gene mediated by SRE and subsequent production of the gene product (protein) of the reporter gene. That is, activation of proliferative signals in the SRE-reporter gene vector-transfected cells can be detected by assaying the enzyme activity of the reporter gene protein.

Specifically, the compound that changes the binding properties of the ligand of the present invention to the receptor of the present invention can be screened by assaying the enzyme activities of the reporter gene protein on the cells in the presence of a substance capable of increasing the intracellular cAMP level, in the case of contacting the ligand of the present invention with the SRE-reporter gene vector-transfected cells where the receptor of the present invention is expressed and in the case of contacting the ligand of the present invention and a test compound with the SRE-reporter gene vector-transfected cells where the receptor of the present invention is expressed; and comparing the activities.

As the vector, there may be employed, e.g., PicaGene Basic Vector, PicaGene Enhancer Vector (Toyo Ink Mfg. Co., Ltd.), and the like. A SRE-containing DNA is inserted into the vector described above at the multicloning site upstream the reporter gene, e.g., luciferase gene, which is made a SRE-reporter gene vector.

According to this method, the test compound which suppresses the enzyme activity of the reporter gene protein by the ligand of the present invention can be selected as an antagonist candidate compound.

On the other hand, the agonist can be screened as well by contacting a test compound alone with the cell where the receptor of the present invention is expressed and measuring an increase of luminescence level as in the ligand of the present invention.

Taking as an example in which luciferase is used as a reporter gene, a specific example of this screening method is described below.

The SRE-reporter gene (luciferase)-transfected cells where the receptor of the present invention is expressed are plated on a 24-well plate in $5 \times 10^3$ cells/well followed by cultivation for 48 hours. The cells are washed with Hanks' buffer (pH 7.4) containing 0.05% BSA and 20 mM HEPES (hereinafter merely referred to as a reaction buffer). Thereafter, 0.5 ml of the reaction buffer is added to the cells and the mixture is kept warm in the medium for 30 minutes. The reaction buffer is removed and 0.25 ml of a fresh reaction buffer is added to the cells. Thereafter, 0.25 ml of the reaction buffer supplemented with 10 μM of the ligand of the present invention or 10 μM of the ligand of the present invention and a test compound is added to the cells. The reaction is then carried out at 37° C. for 24 minutes. The cells are dissolved in a cell lysis agent for PicaGene (Toyo Ink Mfg. Co., Ltd.) and a luminescent substrate (Toyo Ink Mfg. Co., Ltd.) is added to the lysate. Luminescence by luciferase is measured with a luminometer, a liquid scintillation counter or a top counter. The levels of luminescence by luciferase are measured when only the ligand of the present invention is added and when 10 μM of the ligand of the present invention and a test compound are added, and compared therebetween.

The ligand of the present invention increases the luminescence level by luciferase. The compound that suppresses the increase can be selected as an antagonist candidate compound.

As the reporter gene, there may be employed genes, e.g., alkaline phosphatase, chloramphenicol acetyltransferase, β-galactosidase, etc. The enzyme activities of these reporter gene proteins are assayed in accordance with methods publicly know, or using commercially available assay kits. The alkaline phosphatase activity can be assayed by using, e.g., Lumi-Phos 530 manufactured by Wako Pure Chemical Industries, Ltd.; the chloramphenicol acetyltransferase activity by using, e.g., FAST CAT chloramphenicol Acetyltransferase Assay Kit manufactured by Wako Pure Chemical Industries, Ltd.; and the β-galactosidase activity by using, e.g., Aurora Gal-XE manufactured by Wako Pure Chemical Industries, Ltd.

(5) The cells where the receptor of the present invention is expressed extracellularly release arachidonic acid metabolites by stimulation of the ligand of the present invention. Utilizing this reaction, the stimulating activities of the ligand of the present invention on the cell where the receptor of the present invention is expressed are assayed, whereby the compound that changes the binding properties of the ligand of the present invention to the receptor of the present invention can be screened.

Labeled arachidonic acid is previously taken up into the cell where the receptor of the present invention is expressed. Thus, the arachidonic acid metabolite releasing activity can be assayed by measuring the labeled arachidonic acid metabolite released at the outside of the cell.

Specifically, the compound that changes the binding properties of the ligand of the present invention to the receptor of the present invention can be screened by assaying arachidonic acid metabolite-releasing activities, in the case of contacting the ligand of the present invention with the labeled arachidonic acid-containing cells where the receptor of the present invention is expressed and in the case of contacting the ligand of the present invention and a test compound with the labeled arachidonic acid-containing cells where the receptor of the present invention is expressed; and comparing the activities.

In this method, the test compound that inhibits the arachidonic acid metabolite-releasing activity by the ligand of the present invention can be selected as an antagonist candidate compound.

Also, a test compound alone is brought into contact with the cell where the receptor of the present invention is expressed and the arachidonic acid metabolite-releasing activity in the cell where the receptor of the present invention is expressed is examined by publicly known methods. Thus, the compound showing the agonist activity can be screened as well.

A specific example of this screening method is described below.

The cells where the receptor of the present invention is expressed are plated on a 24-well plate in $5 \times 10^4$ cells/well. After cultivation for 24 hours, [$^3$H] arachidonic acid is added to the cells in 0.25 µCi/well. Sixteen hours later, the cells are washed with Hanks' balanced salt solution (pH 7.4) containing 0.05% BSA and 20 mM HEPES (hereinafter simply referred to as a reaction buffer). To each well is added 500 µl of the reaction buffer containing the ligand of the present invention in the final concentration of 10 µM, or the ligand of the present invention in the final concentration of 10 µM and a test compound. After incubation at 37° C. for 60 minutes, 400 µl of the reaction solution is charged in a scintillator and the amount of [$^3$H] arachidonic acid metabolites released in the reaction solution is measured using a scintillation counter.

When the amount of [$^3$H] arachidonic acid metabolites when 500 µl of the reaction buffer alone is added (neither the ligand of the present invention nor the test compound is added) is taken as 0% and the amount of [$^3$H] arachidonic acid metabolites when the reaction buffer containing 10 µM of the ligand of the present invention is added (no test compound is added) is taken as 100%, the amount of [$^3$H] arachidonic acid metabolites released where the test compound is added is calculated.

The compound showing the arachidonic acid metabolite-releasing activity of, e.g., 50% or less, can be selected as an antagonist candidate compound.

(6) In the cells where the receptor of the present invention is expressed, the intracellular Ca level increases by stimulation of the ligand of the present invention. Utilizing this reaction, the stimulating activities of the ligand of the present invention on the cells where the receptor of the present invention is expressed are assayed, whereby the compound that changes the binding properties of the ligand of the present invention to the receptor of the present invention can be screened.

Specifically, the compound that changes the binding properties of the ligand of the present invention to the receptor of the present invention is screened by assaying the intracellular Ca level increasing activities, in the case of contacting the ligand of the present invention with the cells where the receptor of the present invention is expressed and in the case of contacting the ligand of the present invention and a test compound with the cells where the receptor of the present invention is expressed; and comparing the activities. The assay is carried out in accordance with methods publicly known.

In this method, the test compound that suppresses the intracellular calcium level increasing activity by the ligand of the present invention can be selected as an antagonist candidate compound.

On the other hand, the agonist can be screened as well by assaying an increase of fluorescence intensity by the addition of a test compound alone.

A specific example of the screening method is described below.

The cells where the receptor of the present invention is expressed are plated on a sterilized cover glass for microscopy. Two days after, the culture medium is replaced by HBSS in which 4 mM Fura-2 AM (Dojin Kagaku Kenkyusho) is suspended, followed by allowing to stand at room temperature for 2 hours and 30 minutes. After washing with HBSS, the cover glass is set on a cuvette, and an increased ratio of fluorescence intensity at 505 nm is measured with a fluorescence spectrophotometer at excited wavelengths of 340 nm and 380 nm, when the ligand of the present invention or the ligand of the present invention and a test compound is/are added, and comparison is made.

Also, FLIPR (manufactured by Molecular Device Co.) may be used. Fluo-3 AM (manufactured by Dojin Kagaku Kenkyusho) is added to a suspension of the cells where the receptor of the present invention is expressed, thereby to take Fluo-3 AM into the cells. After the supernatant is washed several times through centrifugation and the cells are plated on a 96-well plate. After setting in the FLIPR device, the ligand of the present invention or the ligand of the present invention and a test compound is/are added thereto. Using a fluorescence spectrophotometer, an increase in the ratio of fluorescence intensity is measured and comparison is made, as in Fura-2.

Furthermore, the compound that changes the binding properties of the ligand of the present invention to the receptor of the present invention can also be screened by co-expressing a gene (e.g., aequorin, etc.) for the protein that emits light in response to increased Ca ions in the cells where the receptor of the present invention is expressed, and utilizing the luminescence emitted by conformational switch of the gene protein (e.g., aequorin, etc.) to the Ca-bound protein.

The cells where the receptor of the present invention is expressed and the gene of protein capable of emitting light by increasing the intracellular Ca ions is co-expressed, are plated on a 96-well plate. The ligand of the present invention or the ligand of the present invention and a test compound is/are added thereto and using a fluorescence spectrophotometer, an increase in the ratio of fluorescence intensities is measured and comparison is made as described above.

The test compound that suppresses the increase in fluorescence intensity by the ligand of the present invention can be selected as an antagonist candidate compound.

(7) When the receptor agonist is added to receptor-expressing cells, the level of intracellular inositol triphosphate increases. By utilizing the intracellular inositol triphosphate producing activity of the ligand of the present invention in the cells where the receptor of the present invention is expressed, the compound that changes the binding properties of the ligand of the present invention to the receptor of the present invention can be screened.

Specifically, the compound that changes the binding properties of the ligand of the present invention to the receptor of the present invention is screened by assaying the inositol triphosphate producing activities in the presence of labeled inositol, in the case of contacting the ligand of the present invention with the cells where the receptor of the present invention is expressed and in the case of contacting the ligand of the present invention and a test compound with the cells where the receptor of the present invention is expressed; and comparing the activities. The assay is carried out in accordance with methods publicly known.

In this method, the test compound that suppresses the inositol triphosphate producing activities can be selected as an antagonist candidate compound.

On the other hand, an agonist can also be screened by contacting a test compound alone with the cells where the receptor of the present invention is expressed and measuring an increase in the inositol triphosphate production.

A specific example of the screening method is described below.

The cells wherein the receptor of the present invention is expressed are plated on a 24-well plate and cultured for a day. Then, the cells are cultured for a day in medium supplemented with myo-[2-$^3$H] inositol (2.5 µCi/well). The cells are thoroughly washed with radioactive inositol-free medium. After the ligand of the present invention or the ligand of the present invention and a test compound is/are added to the cells, 10% perchloric acid is added to terminate the reaction. The reaction mixture is neutralized with 1.5 M KOH and 60 mM HEPES solution and then passed through a column packed with 0.5 ml of AG1×8 resin (Bio-Rad). After washing with 5 mM sodium tetraborate ($Na_2B_4O_7$) and 60 mM ammonium formate, the radioactivity eluted with 1M ammonium formate and 0.1M formic acid is assayed with a liquid scintillation counter. When the radioactivity without adding the ligand of the present invention is made 0% and the radioactivity when the ligand of the present invention is added is made 100%, an effect of the test compound on the binding of the ligand of the present invention to the receptor of the present invention is calculated.

A test compound which reduces the inositol triphosphate production activity to, e.g., 50% or less, can be selected as an antagonist candidate compound.

(8) The compound that changes the binding properties of the ligand of the present invention to the receptor of the present invention can be screened by assaying the stimulating activities of the ligand of the present invention on the cells where the receptor of the present invention is expressed, using a TRE-reporter gene vector.

A DNA containing TRE (TPA response element) is inserted into a vector upstream the reporter gene to acquire a TRE-reporter gene vector. In the TRE-reporter gene vector-transfected cells where the receptor of the present invention is expressed, stimulation accompanied by an increase of the intracellular Ca level induces expression of TRE-mediated reporter gene and production of the reporter gene product (protein) subsequent thereto. That is, changes in the calcium level in the TRE-reporter gene vector-transfected cells can be detected by assaying the enzyme activity of the reporter gene protein.

Specifically, the compound that changes the binding properties of the ligand of the present invention to the receptor of the present invention is screened by assaying the enzyme activities of the reporter gene protein, in the case of contacting the ligand of the present invention with the TRE-reporter gene vector-transfected cells where the receptor of the present invention is expressed and in the case of contacting the ligand of the present invention and a test compound with the TRE-reporter gene vector-transfected cells where the receptor of the present invention is expressed; and comparing the activities.

As the vector, there may be employed, e.g., PicaGene Basic Vector, PicaGene Enhancer Vector (Toyo Ink Mfg. Co., Ltd.), and the like. A DNA containing TRE is inserted into the vector described above at the multicloning site upstream the reporter gene, e.g., luciferase gene, which is made a TRE-reporter gene vector.

In this method, the test compound that suppresses the enzyme activity of the reporter gene protein by the ligand of the present invention can be selected as an antagonist candidate compound.

On the other hand, the agonist can be screened as well by contacting a test compound alone with the TRE-reporter gene vector-transfected cells where the receptor of the present invention is expressed and measuring the increased luminescence level as in the ligand of the present invention.

Taking as an example the embodiment wherein luciferase is used as the reporter gene, a specific example of this screening method is described below.

The TRE-reporter gene (luciferase)-transfected cells where the receptor of the present invention is expressed are plated on a 24-well plate in $5 \times 10^3$ cells/well followed by cultivation for 48 hours. After the cells are washed with Hanks' buffer (pH 7.4) containing 0.05% BSA and 20 mM HEPES, 10 μM of the ligand of the present invention or 10 μM of the ligand of the present invention and a test compound is/are added to the cells, followed by reacting at 37° C. for 60 minutes. The cells are dissolved in a cell lysis agent for PicaGene (Toyo Ink Mfg. Co., Ltd.) and a luminescence substrate (Toyo Ink Mfg. Co., Ltd.) is added to the lysate. The luminescence by luciferase is measured by a luminometer, a liquid scintillation counter or a top counter. The amounts of luminescence by luciferase are measured when the ligand of the present invention is added and when 10 μM of the ligand of the present invention and a test compound are added, and compared therebetween.

In response to the increased intracellular calcium by the ligand of the present invention, the amount of luminescence by luciferase increases. The compound that suppresses the increase can be selected as an antagonist candidate compound.

As the reporter gene, there may be employed genes, e.g., alkaline phosphatase, chloramphenicol acetyltransferase, β-galactosidase, etc. The enzyme activities of these reporter gene proteins are assayed in accordance with methods publicly known, or by using assay kits commercially available. The alkaline phosphatase activity can be assayed by using, e.g., Lumi-Phos 530 manufactured by Wako Pure Chemical Industries, Ltd.; the chloramphenicol acetyltransferase activity using, e.g., FAST CAT chloramphenicol Acetyltransferase Assay Kit manufactured by Wako Pure Chemical Industries, Ltd.; and the β-galactosidase activity using, e.g., Aurora Gal-XE manufactured by Wako Pure Chemical Industries, Ltd.

(9) In the cell where the receptor of the present invention is expressed, MAP kinase is activated by stimulation of the ligand of the present invention. Utilizing the reaction, the compound that changes the binding properties of the ligand of the present invention to the receptor of the present invention can be screened by assaying the stimulation activities of the ligand of the present invention on the cell where the receptor of the present invention is expressed.

Specifically, the compound that changes the binding properties of the ligand of the present invention to the receptor of the present invention is screened by assaying the cell growth, in the case of contacting the ligand of the present invention with the cells where the receptor of the present invention is expressed and in the case of contacting the ligand of the present invention and a test compound with the cells where the receptor of the present invention is expressed; and comparing the cell growth.

The growth of the cells where the receptor of the present invention is expressed may be determined by assaying, e.g., the MAP kinase activity, the thymidine uptake activity, the cell count, etc.

In a specific example, the MAP kinase activity is assayed as follows. The ligand of the present invention or the ligand of the present invention and a test compound is/are added to the cell where the receptor of the present invention is expressed; immunoprecipitation is carried out using an anti-MAP kinase antibody to obtain a MAP kinase fraction from a cell lysate; then using, e.g., MAP Kinase Assay Kit manufactured by Wako Pure Chemical Industries, Ltd. and $\gamma$-[$^{32}$P]-ATP, the MAP kinase activity is assayed; and comparison is made.

The thymidine uptake activity can be assayed by plating on a 24-well plate the cell where the receptor of the present invention is expressed, followed by incubation. After the ligand of the present invention or the ligand of the present invention and a test compound is/are added to the cells, and radioactively labeled thymidine (e.g., [methyl-$^3$H]-thymidine, etc.) is added thereto. Then the cells are lysed and by counting the radioactivity of the labeled thymidine taken up into the cells with a liquid scintillation counter, the thymidine uptake activity is assayed and comparison is made.

In assaying the ATP levels, cells wherein the receptor of the present invention is expressed are plated on a 96-well plate and incubated. The ligand of the present invention or the ligand of the present invention and a test compound is/are added thereto, and intracellular ATP levels are assayed using, e.g., CellTiter-Glo (Promega) and compared.

To determine the cell counting, the cells where the ligand of the present invention is expressed are plated on a 24-well plate, followed by incubation. The ligand of the present invention or the ligand of the present invention and a test compound is/are added to the cells, and MTT (3-(4,5-dimethyl-2-thiazolyl)-2,5-diphenyl-2H-tetrazolium bromide) is further added thereto. MTT taken up into the cells changes to MTT formazan, which absorption is measured at 570 nm, after cell lysis with isopropanol rendered acidic with hydrochloric acid. Then, comparison is made.

According to this method, the test compound that suppresses the growth of the cells where the receptor of the present invention is expressed can be selected as an antagonist candidate compound.

On the other hand, the agonist may be screened as well by contacting a test compound alone with the cells where the receptor of the present invention is expressed and assaying the cell growth activity as in the ligand of the present invention.

A specific example of the screening method utilizing the thymidine uptake activity is described below.

The cells where the receptor of the present invention is expressed are plated on a 24-well plate in 5000 cells/well followed by incubation for one day. Next, the cells are incubated in a serum-free medium for 2 days to bring the cells under starvation. The ligand of the present invention or the ligand of the present invention and a test compound is/are added to the cells. After incubation for 24 hours, [methyl-$^3$H] thymidine is added in 0.015 MBq/well, followed by incubation for 6 hours. After the cells are washed with PBS, methanol is added to the cells. The mixture is allowed to stand for 10 minutes. Next, 5% trichloroacetic acid is added and the mixture is allowed to stand for 15 minutes. The immobilized cells are washed 4 times with distilled water. After cell lysis with 0.3 N sodium hydroxide solution, the radioactivity in the lysate is assayed with a liquid scintillation counter.

The compound that suppresses the increase in the radioactivity by the addition of the ligand of the present invention can be selected as an antagonist candidate compound.

(10) In the cell where the receptor of the present invention is expressed, the potassium channel is activated by stimulation of the ligand of the present invention so that K ions present within the cells are effluxed outside the cells. Utilizing this reaction, the compound that changes the binding properties of the ligand of the present invention to the receptor of the present invention can be screened by assaying the stimulating activities of the ligand of the present invention on the cells where the receptor of the present invention is expressed.

Rb ions (rubidium ions) in the related elements to K ions flow out of the cells through the potassium channel without being discriminated from K ions. Thus, radioactive isotope Rb ($[^{86}Rb]$) is previously incorporated into the cells where the receptor of the present invention is expressed, and the efflux of $^{86}$Rb that flows out in response to stimulation by the ligand of the present invention (efflux activity) is determined thereby to assay the stimulating activities of the ligand of the present invention on the cells where the receptor of the present invention is expressed.

Specifically, the compound that changes the binding properties of the ligand of the present invention is screened by assaying $^{86}$Rb efflux activities in the presence of $^{86}$Rb, in the case of contacting the ligand of the present invention with the cells where the receptor of the present invention is expressed and in the case of contacting the ligand of the present invention and a test compound are brought with the cells where the receptor of the present invention is expressed; and comparing the activities.

In this method, the test compound that suppresses the increase of the $^{86}$Rb efflux activities associated with stimulation by the ligand of the present invention can be selected as an antagonist candidate compound.

On the other hand, the agonist can be screened as well by contacting a test compound alone with the cell where the receptor of the present invention is expressed and measuring the increase in the efflux activity of $^{86}$Rb as in the ligand of the present invention.

A specific example of the screening method is described below.

The cells where the receptor of the present invention is expressed are plated on a 24-well plate and cultured for 2 days. Thereafter, the cells are kept warm for 2 hours in a medium containing 1 mCi/ml of $^{86}$RbCl. The medium is thoroughly washed to completely remove $^{86}$RbCl in the outer liquid. The ligand of the present invention or the ligand of the present invention and a test compound is/are added to the cells. After the outer liquid is recovered 30 minutes later, the radioactivity is measured with a γ counter, and comparison is made.

The test compound which suppresses the increase in the efflux activity of $^{86}$Rb by stimulation of the ligand of the present invention can be selected as an antagonist candidate compound.

(11) The cell where the receptor of the present invention is expressed reacts with the ligand of the present invention so that the extracellular pH changes. Utilizing this reaction, the compound that changes the binding properties of the ligand of the present invention to the receptor of the present invention can be screened by assaying the stimulating activities of the ligand of the present invention on the cell where the receptor of the present invention is expressed.

Specifically, the compound that changes the binding properties of the ligand of the present invention to the receptor of the present invention is screened by measuring changes in extracellular pH, in the case of contacting the ligand of the present invention with the cells where the receptor of the present invention is expressed and in the case of contacting the ligand of the present invention and a test compound with the cells where the receptor of the present invention is expressed; and comparing the changes.

The extracellular pH change is determined using, e.g., Cytosensor Device (Molecular Device, Inc.).

In this method, the test compound that suppresses the extracellular pH change by the ligand of the present invention can be selected as an antagonist candidate compound.

On the other hand, the agonist can be screened as well by contacting a test compound alone with the cell where the receptor of the present invention is expressed and measuring the extracellular pH changes, as in the ligand of the present invention.

A specific example of the screening method is described below.

The cells where the receptor of the present invention is expressed are cultured overnight in a capsule for Cytosensor Device, which is set in a chamber of the device to reflux 0.1% BSA-containing RPMI 1640 medium (manufactured by Molecular Device, Inc.) until the extracellular pH becomes stable. After the pH becomes stable, a medium containing the ligand of the present invention or the ligand of the present invention and a test compound is refluxed onto the cells. The pH changes in the medium caused by reflux are measured and compared.

The compound that suppresses the extracellular pH change by the ligand of the present invention can be selected as an antagonist candidate compound.

(12) In yeast (*Saccharomyces Cerevisiae*), the sex pheromone receptor STe2 of haploid α-mating type (MATα) is coupled to G protein Gpal and activates MAP kinase in response to the sex pheromone α-mating factor, whereby Far1 (cell-cycle arrest) and the transcription activator Ste12 are activated. Ste12 induces expression of various proteins (e.g., FUS1 which takes part in mating). On the other hand, regulator Sst2 functions to inhibit the foregoing process. In this system, an attempt has been made to construct the assay system for the reaction of a receptor agonist with a receptor, which involves preparing a receptor gene-transfected yeast, activating the intracellular signal transduction system in yeast by stimulation with the receptor agonist and using the resulting growth, etc. as an indicator (Trends in Biotechnology, 15, 487-494, 1997). Utilizing this receptor gene-transfected yeast system, the compound that changes the binding properties of the ligand of the present invention to the receptor of the present invention can be screened.

A specific example is described below.

Ste2 in MATα yeast and the gene encoding Gpal are removed and instead, a gene for the receptor of the present invention and a gene encoding the Gpal-Gai2 fused protein are introduced. The gene encoding Far1 is removed to cause no cell-cycle arrest and the gene encoding Sst2 is removed to increase the sensitivity in response to the ligand of the present invention. Furthermore, FUS1-HIS3 gene, which is FUS1 ligated with histidine biosynthesis gene HIS3, is introduced. The foregoing genetic recombinant engineering can be carried out by the method described in, e.g., Molecular and Cellular Biology, 15, 6188-6195, 1995, using the receptor of the present invention in place of somatostatin receptor type 2 (SSTR2) gene.

The thus constructed transformant yeast is responsive to the ligand of the present invention with a high sensitivity so that MAP kinase is activated to cause synthesis of histidine biosynthesis enzyme. Thus, the transformant becomes capable of growing in a histidine-deficient medium.

Accordingly, the compound that changes the binding properties of the ligand of the present invention to the receptor of the present invention can be screened by incubating the yeast described above where the receptor of the present invention is expressed (MATα yeast wherein Ste2 gene and Gpa1 gene are removed, the receptor gene of the present invention and the Gpa1-Gai2 fused protein-encoding gene, Far gene and Sst2 gene are removed, and FUS1-HIS3 gene is transfected) in a histidine-deficient medium, contacting the ligand of the present invention or the ligand of the present invention and a test compound with the yeast, assaying growth of the yeast, and comparing the growth.

In this method, the test compound that suppresses growth of the yeast can be selected as an antagonist candidate compound.

On the other hand, the agonist can be screened as well by contacting a test compound alone with the yeast where the receptor of the present invention is expressed and assaying growth of yeast as in the ligand of the present invention.

A specific example of the screening method is described below.

The yeast described above where the receptor of the present invention is expressed thus produced is incubated overnight in a complete synthesis liquid medium and then added to a histidine-free, dissolved agar medium in a concentration of $2 \times 10^4$ cells/ml. Then, the yeast is plated on a square Petri dish of 9×9 cm. After the agar is solidified, a sterilized filter paper impregnated with the ligand of the present invention or the ligand of the present invention and a test compound is put on the agar surface, which is incubated at 30° C. for 3 days. To determine the effect of the test compound, growth of yeast around the filter paper is compared to the case wherein the sterilized filter paper impregnated only with the ligand of the present invention. Alternatively, the assay can be made by previously adding the ligand of the present invention to a histidine-free agar medium, impregnating the sterilized, filter paper with a test compound alone to incubate the yeast and monitoring that growth of the yeast over the entire surface of the Petri dish is affected at the periphery of the filter paper.

The compound that suppresses growth of the yeast can be selected as an antagonist candidate compound.

(13) When the receptor gene RNA of the present invention is injected into *Xenopus laevis* oocytes and stimulated by the ligand of the present invention, the intracellular Ca ion level increases to cause a calcium-activated chloride current, which can be taken as fluctuation in membrane potential (the same applies also to the case where fluctuation occurs in K ion level gradient). Utilizing the above reaction caused by the ligand of the present invention in *Xenopus laevis* oocytes where the receptor of the present invention is transfected, the compound that changes the binding properties of the ligand of the present invention to the receptor of the present invention can be screened by assaying the stimulating activities of the ligand of the present invention on the cells where the receptor of the present invention is expressed.

Specifically, the compound that changes the binding properties of the ligand of the present invention to the receptor of the present invention can be screened by assaying changes in cell membrane potential, in the case of contacting hen the ligand of the present invention with *Xenopus laevis* oocytes where the receptor gene RNA of the present invention is transfected and in the case of contacting the ligand of the present invention and a test compound with *Xenopus laevis* oocytes where the receptor gene RNA of the present invention is transfected; and comparing the changes.

In this method, the test compound that suppresses the changes in cell membrane potential can be selected as an antagonist candidate compound.

On the other hand, the agonist can be screened as well by contacting a test compound alone with *Xenopus laevis* oocytes where the receptor gene RNA of the present invention is transfected and assaying the changes in cell membrane potential as in the ligand of the present invention.

A specific example of the screening method is described below.

A female individual of *Xenopus laevis* anesthetized by immersing in ice water is anatomized to withdraw oocytes. The oocyte clusters are treated with collagenase (0.5 mg/ml) dissolved in an MBS solution (88 mM NaCl, 1 mM KCl, 0.41 mM $CaCl_2$, 0.33 mM $Ca(NO_3)_2$, 0.82 mM $MgSO_4$, 2.4 mM $NaHCO_3$, 10 mM HEPES; pH 7.4) at 19° C. for 1 to 6 hours at 150 rpm, until the oocytes are loosen. Washing is performed 3 times by replacing the outer liquid by the MBS solution followed by microinjection of the receptor gene of the present invention or poly A-added cRNA (50 ng/50 nl) with a micromanipulator.

The receptor gene mRNA of the present invention may be prepared from tissues or cells, or may be transcribed from plasmids in vitro. The receptor gene mRNA of the present invention is incubated in the MBS solution at 20° C. for 3 days. The oocytes are placed in a hole of a voltage clamp device, which is continuously perfused with Ringer's solution, and impaled into the cells with glass microelectrodes for voltage clamp and glass microelectrodes for potential recording, in which (−) electrode is placed outside the oocytes. When the holding potential stabilizes, Ringer's solution containing the ligand of the present invention or the ligand of the present invention and a test compound is perfused to record a change in potential. An effect of the compound can be determined by comparing a change in cell membrane potential of the *Xenopus laevis* oocytes where the receptor gene RNA of the present invention is transfected with the case when the Ringer's solution containing the ligand of the present invention alone is perfused.

The compound that suppresses the changes in cell membrane potential can be selected as an antagonist candidate compound.

In the system described above, the changes in potential can be monitored more easily when the variations in potential increase. Therefore, polyA-added RNA of various G protein genes may be introduced. Also, the amount of luminescence, not the changes in membrane potential, can be measured by co-injecting polyA-added RNA of a gene for the protein (e.g., aequorin, etc.) that emits light in the presence of calcium.

(14) A cell wherein the receptor of the present invention is expressed reacts with the ligand of the present invention so that the receptor is taken up into the cell from the cell surface (internalization). Utilizing this reaction, the compound that changes the binding properties of the ligand of the present invention to the receptor of the present invention can be screened by assaying the stimulating activities of the ligand of the present invention on the cells where the receptor of the present invention is expressed.

Specifically, the compound that changes the binding properties of the ligand of the present invention to the receptor of the present invention can be screened by assaying the degree of internalization of the receptor, in the case of contacting the ligand of the present invention with a cell wherein the receptor of the present invention is expressed and in the case of contacting the ligand of the present invention and a test compound with a cell wherein the receptor of the present invention is expressed, and comparing the changes.

The internalization of the receptor can be detected by observing the receptor of the present invention-GFP fusion protein, which is expressed on the cell, using an image analyzer [e.g., fluorescence microscope, AQUACOSMOS (Hamamatsu Photonics), etc.] and analyzing where the receptor of the present invention is present.

According to this method, the test compound that suppresses the internalization of the receptor by the ligand of the present invention can be selected as an antagonist candidate compound.

On the other hand, when a test compound alone is brought in contact with the cell where the receptor of the present invention is expressed and its internalization is detected as in the ligand of the present invention, the agonist can be screened as well.

A specific example of the screening methods is described below.

An expression plasmid is constructed to express a fused protein of Green Fluorescent Protein (GFP) cDNA isolated from jellyfish *Auquorea Victoria*, fused to the receptor of the present invention at the C-terminus to fit the translation frame. In this case, a fragment excised from the GFP expression vector pQBI25 (Takara Shuzo Co., Ltd.) is used as GFP cDNA. The constructed receptor-GFP fusion protein expression plasmid is transfected into CHO cells in a conventional manner to obtain the receptor-GFP fusion protein expression CHO cell line. This cell line is plated on a Lab-TekII cover glass chamber (Nalgen Nunc, Inc.). After incubation overnight at 37° C. in 5% $CO_2$, a test compound is added thereto.

The fluorescent images of GFP are then observed with a confocal microscope (Leica, Inc.) at an excited wavelength of 488 nm.

The compound that suppresses the internalization by the ligand of the present invention can be selected as an antagonist candidate compound.

The kit for screening the compound or its salt that changes the binding properties of the ligand of the present invention to the receptor of the present invention comprises the receptor of the present invention or the cell or cell membrane fraction containing the receptor of the present invention, and the ligand of the present invention.

Examples of the screening kits of the present invention are as follow.

1. Reagents for Screening
(i) Assay Buffer and Wash Buffer

Hanks' balanced salt solution (manufactured by Gibco Co.) supplemented with 0.05% bovine serum albumin (manufactured by Sigma Co.).

The solution is sterilized by filtration through a 0.45 µm filter, and stored at 4° C. or may be prepared at use.
(ii) Preparation of the Receptor of the Present Invention CHO cells where the receptor of the present invention is expressed are subcultured on a 12-well plate at a density of $5\times10^5$ cells/well and cultured at 37° C. under 5% $CO_2$ and 95% air for 2 days.
(iii) Labeled Ligand The ligand of the present invention labeled with radioisotope such as [$^3$H], [$^{125}$I], [$^{14}$C], [$^{32}$P], [$^{33}$P], [$^{35}$S], etc. A solution of the ligand dissolved in an appropriate solvent or buffer is stored at 4° C. or −20° C. and upon use, diluted to 1 µM with the assay buffer.
(iv) Standard Ligand Solution The ligand of the present invention is dissolved in PBS containing 0.1% bovine serum albumin (manufactured by Sigma Co.) in a volume of 1 mM, and the solution is stored at −20° C.

2. Assay Method
(i) The cells where the receptor of the present invention is expressed are cultured on a 12-well culture plate. After washing twice with 1 ml of the assay buffer, 490 µl of the assay buffer is added to each well.

(ii) After 5 µl of a solution of test compound in $10^{-3}$ to $10^{-10}$ M is added, 5 µl of a labeled form of the ligand of the present invention is added thereto. The reaction is carried out at room temperature for an hour. To examine the non-specific binding, 5 µl of the ligand of the present invention of $10^{-3}$ M is previously added in place of the test compound.

(iii) The reaction solution is removed and the wells are washed 3 times with 1 ml of the wash buffer. The labeled ligand of the present invention bound to the cells is dissolved in 0.2N NaOH-1% SDS, and mixed with 4 ml of liquid scintillator A (manufactured by Wako Pure Chemical Industries, Ltd.).

(iv) The radioactivity is measured using a liquid scintillation counter (manufactured by Beckman Co.), and the percent maximum binding (PMB) is calculated in accordance with the following equation.

$$PMB = [(B - NSB)/(B_0 - NSB)] \times 100$$

PMB: Percent maximum binding
B: Value obtained in the presence of a test compound
NSB: Non-specific binding
$B_0$: Maximum binding The compound or its salt, which is obtained using the screening methods or the screening kits of the present invention, is the compound that changes the binding of the ligand of the present invention to the receptor of the present invention, or the compound that promotes or inhibits the activity of the receptor of the present invention and specifically, is (i) the compound or its salt that has the cell stimulating activities mediated by the receptor of the present invention (an agonist to the receptor of the present invention); (ii) the compound that does not have the stimulating activities (an antagonist to the receptor of the present invention); (iii) the compound that promotes the binding affinity of the receptor of the present invention and the ligand of the present invention; (iv) the compound that inhibits the binding affinity of the receptor of the present invention and the ligand of the present invention; or the like. Examples of these compounds include those selected from peptides, proteins, antibodies, non-peptide compounds, synthetic compounds, fermentation products, cell extracts, plant extracts, animal tissue extracts, blood plasma, etc. These compounds may be novel or publicly known compounds.

The same salts given for the receptor of the present invention above apply to the salts of these compounds.

Evaluation of whether the compound is the receptor agonist or antagonist of the present invention described above is determined by, e.g., (i) or (ii) below.

(i) The binding assay according to the screening methods (a) to (c) is performed to obtain the compound that changes the binding properties of the ligand of the present invention to the receptor of the present invention (especially inhibits the binding). It is then determined if the compound has the cell stimulating activities mediated by the receptor of the present invention as described above. The compound or its salt that has the cell-stimulating activities is the receptor agonist of the present invention (agonist), whereas the compound or its salt having no such activities is the receptor antagonist of the present invention (antagonist).

(ii) (a) A test compound is brought in contact with cells containing the receptor of the present invention to assay the cell stimulating activities mediated by the receptor of the present invention. The compound or its salts that has the cell stimulating activities is the receptor agonist of the present invention.

(b) The cell stimulating activities mediated by the receptor of the present invention are assayed in the case of contacting the ligand of the present invention with the cell containing the receptor of the present invention and in the case of contacting the ligand of the present invention and a test compound with the cell containing the receptor of the present invention, and comparison is made on the cell stimulating activities. The compound or its salt capable of reducing the cell stimulating activities by the compound that activates the receptor of the present invention is the receptor antagonist of the present invention.

The ligand of the present invention has the activity of regulating neural activities, motor function modulating activity, etc. and increases the intracellular cAMP level in nerve cells in the striatum, nucleus accumbens, hippocampus, frontal lobe, etc. Thus, the ligand can inhibit overactive mesolimbic dopamine pathway, which is considered as one of the causes for positive symptoms of schizophrenia, to improve the positive symptoms of schizophrenia. Also, the ligand of the present invention can improve hypofunction of the NMDA-type receptor in the cerebral cortex, which is considered as one of the causes for negative symptoms of schizophrenia or cognitive impairment, and improve the negative symptoms of schizophrenia or cognitive impairment. Accordingly, the agonist of the receptor of the present invention has activities similar to the physiological activities (e.g., the activity of regulating neural activities, the motor function modulating activity, etc.) the ligand of the present invention has, and is useful as a safe and low toxic medicament, for example, as an agent for the prevention/treatment of, e.g., mental disorders (e.g., schizophrenia, anxiety, cognitive impairment, panic disorder, phobic disorder, drug-induced psychotic disorder, delusional psychosis, etc.), prolactin hyposecretion (e.g., hypoovarianism, spermatic underdevelopment, menopausal symptoms, hypothyroidism, etc.), hypertension, sleeping disorders [e.g., primary insomnia, circadian rhythm disorders (e.g., change in physical conditions caused by three-shift work, time zone change syndrome (jet lag), etc.] and the like; preferably useful as an agent for the prevention/treatment of schizophrenia, cognitive impairment, prolactin hyposecretion, etc.

The antagonist for the ligand of the present invention can inhibit physiological activities (e.g., the activity of regulating neural activities, the motor function modulating activity, etc.) possessed by the ligand of the present invention, etc. to decrease the intracellular cAMP level in nerve cells in the striatum, nucleus accumbens, hippocampus, frontal lobe, etc., thereby to improve failure in suppression of the intracellular cAMP production induced by dopamine deficiency in the nigrostriatal dopamine pathway, which is considered as a cause of Parkinson's disease. Accordingly, the antagonist for the ligand of the present invention is useful as a safe and low toxic medicament, for example, as an agent for the prevention/treatment of, e.g., mental disorders (e.g., neuroleptic-induced dyskinesia, Parkinson's disease, drug-induced Parkinson's syndrome, extrapyramidal syndrome, etc.), prolactin hypersecretion [e.g., hyperprolactinemia (e.g., sterility, galactorrhea, amenorrhea, atrophy of ovary and uterus, etc.), pituitary tumor, diencephalon tumor, menstrual disorder, etc.] and the like; preferably useful as an agent for the prevention/treatment of Parkinson's disease, hyperprolactinemia (e.g., sterility, galactorrhea, amenorrhea, atrophy of ovary and uterus, etc.), and the like.

The compound that promotes the binding affinity of the receptor of the present invention to the ligand of the present invention is useful as a safe and low toxic medicament, e.g., as an agent for the prevention/treatment of, for example, mental disorders (e.g., schizophrenia, anxiety, cognitive impairment, panic disorder, phobic disorder, drug-induced psychotic disorder, delusional psychosis, etc.), prolactin hyposecretion (e.g., hypoovarianism, spermatic underdevelopment, menopausal symptoms, hypothyroidism, etc.), hypertension, sleeping disorders [e.g., primary insomnia, circadian rhythm disorders (e.g., change in physical conditions caused by three-shift work, time zone change syndrome (jet lag), etc.] and the like; preferably useful as an agent for the prevention/treatment of schizophrenia, cognitive impairment, prolactin hyposecretion, etc.

The compound that inhibits the binding affinity of the receptor of the present invention to the ligand of the present invention is useful as a safe and low toxic medicament, for instance, as an agent for the prevention/treatment of, e.g., mental disorders (e.g., neuroleptic-induced dyskinesia, Parkinson's disease, drug-induced Parkinson's syndrome, extrapyramidal syndrome, etc.), prolactin hypersecretion [e.g., hyperprolactinemia (e.g., sterility, galactorrhea, amenorrhea, atrophy of ovary and uterus, etc.), pituitary tumor, diencephalon tumor, menstrual disorder, etc.] and the like; preferably useful as an agent for the prevention/treatment of Parkinson's disease, hyperprolactinemia (e.g., sterility, galactorrhea, amenorrhea, atrophy of ovary and uterus, etc.), and the like.

Moreover, the present invention also provides the method of screening the compound or its salt that promotes or inhibits the expression of a gene for the receptor of the present invention, which comprises using a polynucleotide of the present invention encoding the receptor of the present invention, and the like.

Specifically, the compound or its salts that promote or inhibit the expression of a gene for the receptor of the present invention is screened by comparing the case (i) where a cell capable of producing the receptor of the present invention is cultured, and the case (ii) where a mixture of the cell capable of producing the receptor of the present invention and a test compound is cultured.

In the screening method described above, the gene expression level of the receptor of the present invention (specifically, the level of the receptor of the present invention or the level of mRNA encoding the receptor of the present invention, etc.) is assayed in the cases (i) and (ii), and comparison is made.

Examples of the test compound include peptides, proteins, antibodies, non-peptide compounds, synthetic compounds, fermentation products, cell extracts, plant extracts, animal tissue extracts, blood plasma, etc. These compounds may be novel or known compounds.

To perform the screening method described above, the cells capable of producing the polypeptide of the present invention or the receptor of the present invention are suspended in a buffer suitable for the screening to prepare the suspension. Any buffer can be used so long as it does not interfere the activities of the receptor of the present invention, including a phosphate buffer or a borate buffer, having pH of about 4 to about 10 (preferably pH of about 6 to about 8), etc.

As the cells capable of producing the receptor of the present invention, there are used, for example, a host (transformant) transformed with a vector containing the DNA encoding the receptor of the present invention. Preferably, animal cells such as CHO cells, etc. are used as the host. For the screening, the transformant, in which the receptor of the present invention has been secreted extracellularly by culturing through the procedures described above, is preferably employed.

The protein level in the receptor of the present invention can be determined by publicly known methods, e.g., by assaying the above-described polypeptide or receptor present in the cell extract, etc., using the antibody of the present invention, in accordance with methods like western blot analysis, ELISA, etc., or modifications thereof.

The gene expression level of the receptor of the present invention can be determined by publicly known methods, e.g., in accordance with methods including northern blotting, reverse transcription-polymerase chain reaction (RT-PCR), real time PCR monitoring system (manufactured by ABI Inc., TaqMan polymerase chain reaction), etc., or modifications thereof.

For example, when a test compound promotes expression of the gene for the receptor of the present invention in the case (ii) described above by at least about 20%, preferably at least 30% and more preferably at least about 50%, as compared to the case (i) above, the test compound can be selected as the compound or its salt that promotes expression of the gene for the receptor of the present invention.

For example, when a test compound inhibits expression of the gene for the receptor of the present invention in the case (ii) described above by at least about 20%, preferably at least 30% and more preferably at least about 50%, as compared to the case (i) above, the test compound can be selected to be the compound or its salt that inhibits expression of the gene for the receptor of the present invention.

The compound or its salt that promotes expression of the gene for the receptor of the present invention (increases the expression level) is used as an agent for the prevention/treatment of, for example, mental disorders (e.g., schizophrenia, anxiety, cognitive impairment, panic disorder, phobic disorder, drug-induced psychotic disorder, delusional psychosis, etc.), prolactin hyposecretion (e.g., hypoovarianism, spermatic underdevelopment, menopausal symptoms, hypothyroidism, etc.), hypertension, sleeping disorders [e.g., primary insomnia, circadian rhythm disorders (e.g., change in physical conditions caused by three-shift work, time zone change syndrome (jet lag), etc.] and the like; preferably useful as an agent for the prevention/treatment of schizophrenia, cognitive impairment, prolactin hyposecretion, etc., as in the ligand of the present invention.

The compound or its salt that inhibits expression of the gene for the receptor of the present invention can suppress the physiological activities of the ligand of the present invention for the receptor of the present invention and is thus useful as an agent for the prevention/treatment of, for example, mental disorders (e.g., neuroleptic-induced dyskinesia, Parkinson's disease, drug-induced Parkinson's syndrome, extrapyramidal syndrome, etc.), prolactin hypersecretion [e.g., hyperprolactinemia (e.g., sterility, galactorrhea, amenorrhea, atrophy of ovary and uterus, etc.), pituitary tumor, diencephalon tumor, menstrual disorder, etc.] and the like; preferably useful as an agent for the prevention/treatment of Parkinson's disease, hyperprolactinemia (e.g., sterility, galactorrhea, amenorrhea, atrophy of ovary and uterus, etc.), and the like.

The compound or its salt, which is obtained using the screening methods or screening kits of the present invention, is the compound selected from, for example, peptides, proteins, antibodies, non-peptide compounds, synthetic compounds, fermentation products, cell extracts, plant extracts, animal tissue extracts, blood plasma, etc. The compound that alters the binding properties of the receptor of the present invention to the ligand of the present invention, the compound that promotes or inhibits the activities or functions of the receptor of the present invention, the compound that promotes or inhibits the expression (increases or decreases the expression level) of the gene for the receptor of the present invention, etc.

The salts of these compounds used are the same given as the salts of the receptor of the present invention described above.

When the compound or its salt, which is obtained by the screening methods or screening kits of the present invention, is used as the aforesaid medicament (the agent for the prevention/treatment, etc.), such can be carried out in a conventional manner.

The compound or its salt can be administered orally, for example, in the form of tablets which may be sugar coated, if necessary, capsules, elixirs, microcapsules etc., or parenterally in the form of injections such as sterile solutions or suspensions in water or in pharmaceutically acceptable solutions other than water. For example, the compound or its salt can be mixed with carriers, flavoring agents, excipients, vehicles, preservatives, stabilizers, binders, etc. in a unit dosage form generally accepted. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin and alginic acid, a lubricant such as magnesium stearate, a sweetening agent such as sucrose, lactose and saccharin, a flavoring agent such as peppermint, akamono oil and cherry, etc. When the unit dosage is in the form of a capsule, liquid carriers such as oils and fats may further be used together with the additives described above. A sterile composition for injection may be formulated in a conventional manner used to make pharmaceutical preparations, e.g., by dissolving or suspending the active ingredients in a vehicle such as water for injection with a naturally occurring vegetable oil such as sesame oil and coconut oil, etc. to prepare the pharmaceutical preparations.

Examples of an aqueous medium for injection include physiological saline and an isotonic solution containing glucose and other auxiliary agents (e.g., D-sorbitol, D-mannitol, sodium chloride, etc.), or the like and may be used in combination with an appropriate dissolution aid such as an alcohol (e.g., ethanol, etc.), a polyalcohol (e.g., propylene glycol and polyethylene glycol, etc.), a nonionic surfactant (e.g., polysorbate 80™, HCO-50, etc.), or the like. Examples of the oily medium include sesame oil, soybean oil, etc., which may also be used in combination with a dissolution aid such as benzyl benzoate, benzyl alcohol, etc. The compound or its salt may further be formulated together with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

Since the pharmaceutical preparation thus obtained is safe and low toxic, it can be administered to human or other warm-blooded mammal (e.g., mouse, rat, rabbit, sheep, swine, bovine, horse, fowl, cat, dog, monkey, chimpanzee, etc.).

The dose of the compounds or salts thereof may vary depending upon the action, target disease, subject to be administered, route of administration, etc.

For example, in oral administration, the compound (agonist) is administered to the patient (as 60 kg body weight) with schizophrenia normally in a dose of about 0.1 to about 100 mg, preferably about 1.0 to about 50 mg, more preferably about 1.0 to about 20 mg per day. When the compound is administered to the patient (as 60 kg body weight) with, e.g., schizophrenia in the form of an injection, it is advantageous to administer the compound intravenously at a daily dose of about 0.01 to about 30 mg, preferably about 0.1 to about 20 mg, more preferably about 0.1 to about 10 mg. For other animal species, the corresponding dose as converted per 60 kg weight can be administered.

For example, in oral administration, the compound (antagonist) is administered to the patient (as 60 kg body weight) with Parkinson's disease normally in a dose of about 0.1 to about 100 mg, preferably about 1.0 to about 50 mg, more preferably about 1.0 to about 20 mg per day. When the compound is administered to the patient (as 60 kg body weight) with, e.g., Parkinson's disease in the form of an injection, it is advantageous to administer the compound intravenously at a daily dose of about 0.01 to about 30 mg, preferably about 0.1 to about 20 mg, more preferably about 0.1 to about 10 mg. For other animal species, the corresponding dose as converted per 60 kg weight can be administered.

[2] Agent for Preventing/Treating Various Diseases Associated with Receptor of the Present Invention.

The receptor of the present invention has the binding activities to the ligand of the present invention, which possesses the activities described above. Accordingly, where the receptor of the present invention (e.g., DNA) involves abnormalities or deficiencies, it is highly likely for one to suffer from, for example, mental disorders (e.g., schizophrenia, anxiety, cognitive impairment, panic disorder, phobic disorder, drug-induced psychotic disorder, delusional psychosis, neuroleptic-induced dyskinesia, Parkinson's disease, drug-induced Parkinson's syndrome, extrapyramidal syndrome, etc.), prolactin-related disorders [e.g., hyperprolactinemia (e.g., sterility, galactorrhea, amenorrhea, atrophy of ovary and uterus, etc.), pituitary tumor, diencephalon tumor, menstrual disorder, prolactin hyposecretion (e.g., hypoovarianism, spermatic underdevelopment, menopausal symptoms, hypothyroidism, etc.), etc.], hypertension, sleeping disorders [e.g., primary insomnia, circadian rhythm disorders (e.g., change in physical conditions caused by three-shift work, time zone change syndrome (jet lag), etc.], and the like. Thus, the receptor of the present invention (e.g., DNA) can be used as a low toxic and safe medicament such as an agent for the prevention/treatment of, for example, mental disorders (e.g., schizophrenia, anxiety, cognitive impairment, panic disorder, phobic disorder, drug-induced psychotic disorder, delusional psychosis, neuroleptic-induced dyskinesia, Parkinson's disease, drug-induced Parkinson's syndrome, extrapyramidal syndrome, etc.), prolactin-related disorders [e.g., hyperprolactinemia (e.g., sterility, galactorrhea, amenorrhea, atrophy of ovary and uterus, etc.), pituitary tumor, diencephalon tumor, menstrual disorder, prolactin hyposecretion (e.g., hypoovarianism, spermatic underdevelopment, menopausal symptoms, hypothyroidism, etc.), etc.], hypertension, sleeping disorders [e.g., primary insomnia, circadian rhythm disorders (e.g., change in physical conditions caused by three-shift work, time zone change syndrome (jet lag), etc.], and the like; preferably as an agent for the prevention/treatment of schizophrenia, cognitive impairment, and the like.

When a patient has a reduced level of, or deficient in the receptor of the present invention in his or her body, the receptor of the present invention can provide the role of the receptor of the present invention sufficiently or properly for the patient, (i) by administering the polynucleotide of the present invention to the patient to express the receptor of the present invention in the body, (ii) by inserting the polynucleotide of the present invention into a cell, expressing the receptor of the present invention and then transplanting the cell to the patient, or (iii) by administering the receptor of the present invention to the patient, or the like.

When the polynucleotide of the present invention is used as the agent for the prevention/treatment described above, the polynucleotide may be administered alone to human or other warm-blooded animal; or the polynucleotide is inserted into an appropriate vector such as retrovirus vector, adenovirus vector, adenovirus-associated virus vector, etc. and then administered to human or other warm-blooded animal in a conventional manner. The polynucleotide of the present invention may also be administered in its intact form; or the polynucleotide may be prepared into a pharmaceutical composition together with physiologically acceptable carriers such as adjuvants, etc. to assist its uptake and the pharmaceutical preparation may be administered by gene gun or through a catheter such as a catheter with a hydrogel.

When the receptor of the present invention is used as the agent for the prevention/treatment described above, it is advantageous to use the receptor in a purity of at least 90%, preferably at least 95%, more preferably at least 98% and most preferably at least 99%.

The receptor of the present invention can be used orally, for example, in the form of tablets which, if necessary, may be sugar coated, capsules, elixirs, microcapsules etc., or parenterally in the form of injectable preparations such as a sterile solution or a suspension, etc. in water or in other pharmaceutically acceptable liquid. These preparations can be manufactured, for example, by mixing the receptor of the present invention with a physiologically acceptable known carrier, a flavoring agent, an excipient, a vehicle, an antiseptic agent, a stabilizer, a binder, etc. in a unit dosage form required in a generally accepted fashion that is applied to making pharmaceutical preparations. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin, alginic acid, etc., a lubricant such as magnesium stearate, a sweetening agent such as sucrose, lactose and saccharin, and a flavoring agent such as peppermint, akamono oil or cherry, etc. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition.

Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol, etc.), a polyalcohol (e.g., propylene glycol, polyethylene glycol, etc.), a nonionic surfactant (e.g., polysorbate 80™, HCO-50, etc.), or the like. Examples of the oily medium include sesame oil, soybean oil, etc., which may also be used in combination with a dissolution aid such as benzyl benzoate, benzyl alcohol, etc. The oily medium may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

The vector in which the polynucleotide (e.g., DNA) of the present invention is inserted may also be prepared into pharmaceutical preparations in a manner similar to the procedures above. Such preparations are generally used parenterally.

Since the thus obtained pharmaceutical preparation is safe and low toxic, the preparation can be administered to human or other warm-blooded mammal (e.g., rat, mouse, guinea pig, rabbit, fowl, sheep, swine, bovine, horse, cat, dog, monkey, etc.).

The dose of the receptor of the present invention varies depending on subject to be administered, target disease, route for administration, etc.; in oral administration of the receptor for the treatment of, e.g., Parkinson's disease, the receptor is administered to an adult (as 60 kg body weight) normally at a daily dose of about 0.1 mg to about 100 mg, preferably about 1.0 to about 50 mg, and more preferably about 1.0 to about 20 mg. In parenteral administration, the dose of the receptor varies depending on subject to be administered, target disease, conditions, route for administration, etc. but when the receptor is administered in the form of an injectable preparation for the treatment of, e.g., Parkinson's disease, it is advantageous to intravenously administer the receptor to an adult (as 60 kg body weight) normally at a daily dose of about 0.01 to about 30 mg, preferably about 0.1 to about 20 mg, and more preferably about 0.1 to about 10 mg. For other animal species, the corresponding dose as converted per 60 kg body weight can be administered.

[3] Quantification of Receptor of the Present Invention

The antibody of the present invention is capable of specifically recognizing the receptor of the present invention. Therefore, the antibody can be used to quantify the receptor of the present invention in a test fluid, especially for quantification by the sandwich immunoassay, etc.

That is, the present invention provides, for example, the following methods of quantification:

(i) a method of quantifying the receptor of the present invention in a test fluid, which comprises competitively reacting the antibody of the present invention with the test fluid and a labeled form of the receptor of the present invention, and measuring the ratio of the labeled receptor of the present invention bound to the antibody; and, (ii) a method of quantifying the receptor of the present invention in a test fluid, which comprises reacting the test fluid with the antibody of the present invention immobilized on a carrier and a labeled form of another antibody of the present invention simultaneously or sequentially, and assaying the activity of the label on the immobilized carrier.

In the quantification method (ii) described above, it is preferred that one antibody recognizes the N-terminal domain of the receptor of the present invention, and another antibody reacts with the C-terminal domain of the receptor of the present invention.

Using a monoclonal antibody to the receptor of the present invention, the receptor of the present invention can be assayed and the detection by tissue staining. etc. is also available. For these purposes, the antibody molecule itself may be used, or F(ab')$_2$, Fab' or Fab fractions of the antibody molecule may be used as well.

The method of quantifying the receptor of the present invention using the antibody of the present invention is not particularly limited, and any method may be used, so long as the amount of antibody, antigen, or antibody-antigen complex in response to the amount of antigen (e.g., the polypeptide level) in a test fluid can be detected by chemical or physical means and can be calculated from a standard curve prepared from standard solutions containing known amounts of the antigen. Advantageously used are, for example, nephrometry, competitive method, immunometric method and sandwich method; in terms of sensitivity and specificity, the sandwich method, which will be described later, is particularly preferred.

Examples of labeling agents, which are employed for the assay method using the same are radioisotopes, enzymes, fluorescent substances, luminescent substances, etc. Examples of the radioisotopes employed are [$^{125}$I], [$^{131}$I], [$^{3}$H], [$^{14}$C], etc. As the enzymes described above, stable enzymes with a high specific activity are preferred; for example, β-galactosidase, β-glucosidase, alkaline phosphatase, peroxidase, malate dehydrogenase and the like are used. Examples of the fluorescent substance used are fluorescamine, fluorescein isothiocyanate and the like. As the luminescent substances, there are employed, for example, luminol, luminol derivatives, luciferin, lucigenin and the like. Furthermore, the biotin-avidin system may also be used for binding an antibody or antigen to the label.

In the immobilization of antigens or antibodies, physical adsorption may be used. Alternatively, chemical binding that is conventionally used for immobilization of polypeptides, enzymes, etc. may be used as well. Examples of the carrier include insoluble polysaccharides such as agarose, dextran, cellulose, etc.; synthetic resins such as polystyrene, polyacrylamide, silicone, etc.; or glass; and the like.

In the sandwich method, the immobilized monoclonal antibody of the present invention is reacted with a test fluid (primary reaction), then with a labeled form of another monoclonal antibody of the present invention (secondary reaction), and the activity of the labeling agent on the immobilizing carrier is assayed, whereby the amount of the receptor in the test fluid can be quantified. The order of the primary and secondary reactions may be reversed, and the reactions may be performed simultaneously or with some time intervals. The methods of labeling and immobilization can be performed by modifications of those methods described above. In the immunoassay by the sandwich method, the antibody used for immobilized or labeled antibody is not necessarily from one species, but a mixture of two or more species of antibodies may be used to increase the measurement sensitivity.

In the methods of the present invention for assaying the receptor of the present invention by the sandwich method, antibodies that bind to different sites of the receptor of the present invention are preferably used as the monoclonal antibodies of the present invention for the primary and secondary reactions. That is, in the antibodies used for the primary and secondary reactions, for example, when the antibody used in the secondary reaction recognizes the C-terminal domain of the receptor of the present invention, it is preferable to use the antibody capable of recognizing the region other than the C-terminal domain for the primary reaction, e.g., the antibody capable of recognizing the N-terminal domain.

The monoclonal antibody of the present invention can be used for the assay systems other than the sandwich method, for example, the competitive method, immunometric method, nephrometry, etc.

In the competitive method, an antigen in a test fluid and a labeled antigen are competitively reacted with an antibody, and the unreacted labeled antigen (F) and the labeled antigen bound to the antibody (B) are separated (B/F separation). The amount of the labeling agent in B or F is measured, and the amount of the antigen in the test fluid is quantified. This reaction method includes a liquid phase method using a soluble antibody as an antibody, polyethylene glycol for B/F separation and a secondary antibody, etc. to the soluble antibody, and an immobilized method either using an immobilized antibody as the primary antibody, or using a soluble antibody as the primary antibody and an immobilized antibody as the secondary antibody.

In the immunometric method, an antigen in a test fluid and an immobilized antigen are competitively reacted with a definite amount of labeled antibody, the immobilized phase is separated from the liquid phase, or an antigen in a test fluid is reacted with an excess amount of labeled antibody, the immobilized antigen is then added to bind the unreacted labeled antibody to the immobilized phase, and the immobilized phase is separated from the liquid phase. Then, the amount of the labeling agent in either phase is measured to quantify the antigen in the test fluid.

In the nephrometry, insoluble precipitates produced after the antigen-antibody reaction in gel or solution are quantified. Even when the amount of an antigen in a test fluid is small and only a small amount of precipitates is obtained, laser nephrometry using scattering of laser, or the like can be advantageously employed.

For applying these immunological assay methods to the quantification methods of the present invention, any particular conditions, procedures, etc. are not required. The assay systems for the receptor of the present invention may be constructed by adding ordinary technical consideration in the art to conventional conditions and procedures in the respective methods. For the details of these general technical means, reference can be made to the following reviews, texts, etc.

For example, reference can be made on Hiroshi Irie, ed. "Radioimmunoassay" (Kodansha, published in 1974), Hiroshi Irie, ed. "Sequel to the Radioimmunoassay" (Kodansha, published in 1979), Eiji Ishikawa, et al. ed. "Enzyme immunoassay" (Igakushoin, published in 1978), Eiji Ishikawa, et al. ed. "Immunoenzyme assay" (2nd ed.) (Igakushoin, published in 1982), Eiji Ishikawa, et al. ed. "Immunoenzyme assay" (3rd ed.) (Igakushoin, published in 1987), Methods in ENZYMOLOGY, Vol. 70 (Immunochemical Techniques (Part A)), ibid., Vol. 73 (Immunochemical Techniques (Part B)), ibid., Vol. 74 (Immunochemical Techniques (Part C)), ibid., Vol. 84 (Immunochemical Techniques (Part D: Selected Immunoassays)), ibid., Vol. 92 (Immunochemical Techniques (Part E: Monoclonal Antibodies and General Immunoassay Methods)), ibid., Vol. 121 (Immunochemical Techniques (Part I: Hybridoma Technology and Monoclonal Antibodies))(all published by Academic Press Publishing), etc.

As described above, the receptor of the present invention can be quantified with high sensitivity, by using the antibody of the present invention.

Furthermore, when an increased level of the receptor of the present invention is detected by quantifying the level of the receptor of the present invention using the antibody of the present invention, it can be diagnosed that one suffers from diseases, for example, mental disorders (e.g., schizophrenia, anxiety, cognitive impairment, panic disorder, phobic disorder, drug-induced psychotic disorder, delusional psychosis, neuroleptic-induced dyskinesia, Parkinson's disease, drug-induced Parkinson's syndrome, extrapyramidal syndrome, etc.), prolactin-related disorders [e.g., hyperprolactinemia (e.g., sterility, galactorrhea, amenorrhea, atrophy of ovary and uterus, etc.), pituitary tumor, diencephalon tumor, menstrual disorder, prolactin hyposecretion (e.g., hypoovarianism, spermatic underdevelopment, menopausal symptoms, hypothyroidism, etc.), etc.], hypertension, sleeping disorders [e.g., primary insomnia, circadian rhythm disorders (e.g., change in physical conditions caused by three-shift work, time zone change syndrome (jet lag), etc.], and the like (especially schizophrenia, cognitive impairment, prolactin hyposecretion, etc.), or it is highly likely that one would suffer from these diseases in the future. Also, when a decreased level of the receptor of the present invention is detected, it can be diagnosed that one suffers from diseases, for example, mental disorders (e.g., schizophrenia, anxiety, cognitive impairment, panic disorder, phobic disorder, drug-induced psychotic disorder, delusional psychosis, neuroleptic-induced dyskinesia, Parkinson's disease, drug-induced Parkinson's syndrome, extrapyramidal syndrome, etc.), prolactin-related disorders [e.g., hyperprolactinemia (e.g., sterility, galactorrhea, amenorrhea, atrophy of ovary and uterus, etc.), pituitary tumor, diencephalon tumor, menstrual disorder, prolactin hyposecretion (e.g., hypoovarianism, spermatic underdevelopment, menopausal symptoms, hypothyroidism, etc.), etc.], hypertension, sleeping disorders [e.g., primary insomnia, circadian rhythm disorders (e.g., change in physical conditions caused by three-shift work, time zone change syndrome (jet lag), etc.], and the like (especially Parkinson's disease, hyperprolactinemia, etc.); or it is highly likely that one would suffer from these diseases in the future.

Besides, the antibody of the present invention can be used for detecting the receptor of the present invention present in test samples such as body fluids, tissues, etc. The antibody can also be used for preparation of antibody columns used to purify the receptor of the present invention, for detection of the receptor of the present invention in each fraction upon purification, for analysis of the behavior of the receptor of the present invention in cells under inspection; etc.

[4] Gene Diagnostic Agent

By using the polynucleotide (DNA) of the present invention, e.g., as a probe, an abnormality (gene abnormality) of the DNA or mRNA encoding the receptor of the present invention in human or other warm-blooded animal (e.g., rat, mouse, guinea pig, rabbit, fowl, sheep, swine, bovine, horse, cat, dog, monkey, etc.) can be detected. Therefore, the DNA of the present invention is useful as a gene diagnostic agent for damages to the DNA or mRNA, its mutation or decreased expression, or increased expression or overexpression of the DNA or mRNA.

The gene diagnosis described above using the DNA of the present invention can be performed by, for example, publicly known Northern hybridization or PCR-SSCP assay (Genomics, 5, 874-879 (1989); Proceedings of the National Academy of Sciences of the United States of America, 86, 2766-2770 (1989)), DNA microarray, etc.

For example, when overexpression of the receptor of the present invention is detected, it can be diagnosed that one suffers from diseases, for example, mental disorders (e.g., schizophrenia, anxiety, cognitive impairment, panic disorder, phobic disorder, drug-induced psychotic disorder, delusional psychosis, neuroleptic-induced dyskinesia, Parkinson's disease, drug-induced Parkinson's syndrome, extrapyramidal syndrome, etc.), prolactin-related disorders [e.g., hyperprolactinemia (e.g., sterility, galactorrhea, amenorrhea, atrophy of ovary and uterus, etc.), pituitary tumor, diencephalon tumor, menstrual disorder, prolactin hyposecretion (e.g., hypoovarianism, spermatic underdevelopment, menopausal symptoms, hypothyroidism, etc.), etc.], hypertension, sleeping disorders [e.g., primary insomnia, circadian rhythm disorders (e.g., change in physical conditions caused by three-shift work, time zone change syndrome (jet lag), etc.], and the like (especially schizophrenia, cognitive impairment, prolactin hyposecretion, etc.); or it is highly likely that one would suffer from these diseases in the future. Also, when reduced expression of the receptor of the present invention is detected, it can be diagnosed that one suffers from diseases, for example, mental disorders (e.g., schizophrenia, anxiety, cognitive impairment, panic disorder, phobic disorder, drug-induced psychotic disorder, delusional psychosis, neuroleptic-induced dyskinesia, Parkinson's disease, drug-induced Parkinson's syndrome, extrapyramidal syndrome, etc.), prolactin-related disorders [e.g., hyperprolactinemia (e.g., sterility, galactorrhea, amenorrhea, atrophy of ovary and uterus, etc.), pituitary tumor, diencephalon tumor, menstrual disorder, prolactin hyposecretion (e.g., hypoovarianism, spermatic underdevelopment, menopausal symptoms, hypothyroidism, etc.), etc.], hypertension, sleeping disorders [e.g., primary insomnia, circadian rhythm disorders (e.g., change in physical conditions caused by three-shift work, time zone change syndrome (jet lag), etc.], and the like (especially Parkinson's disease, hyperprolactinemia (e.g., sterility, galactorrhea, amenorrhea, atrophy of ovary and uterus, etc.), etc.); or it is highly likely that one would suffer from these diseases in the future.

[5] Medicament Comprising Antisense Polynucleotide (e.g., DNA)

The antisense polynucleotide (e.g., antisense DNA) that can bind complementarily to the polynucleotide (e.g., DNA) of the present invention to suppress expression of the polynucleotide (e.g., DNA) can be used as a low toxic and safe medicament including an agent for the prevention/treatment of diseases, for example, mental disorders (e.g., schizophrenia, anxiety, cognitive impairment, panic disorder, phobic disorder, drug-induced psychotic disorder, delusional psychosis, neuroleptic-induced dyskinesia, Parkinson's disease, drug-induced Parkinson's syndrome, extrapyramidal syndrome, etc.), prolactin-related disorders [e.g., hyperprolactinemia (e.g., sterility, galactorrhea, amenorrhea, atrophy of ovary and uterus, etc.), pituitary tumor, diencephalon tumor, menstrual disorder, prolactin hyposecretion (e.g., hypoovarianism, spermatic underdevelopment, menopausal symptoms, hypothyroidism, etc.), etc.], hypertension, sleeping disorders [e.g., primary insomnia, circadian rhythm disorders (e.g., change in physical conditions caused by three-shift work, time zone change syndrome (jet lag), etc.], and the like (especially Parkinson's disease, hyperprolactinemia (e.g., sterility, galactorrhea, amenorrhea, atrophy of ovary and uterus, etc.), and so on.

For example, in the case of using the antisense DNA described above, the antisense DNA is administered solely, or the antisense DNA is inserted into an appropriate vector such as retrovirus vector, adenovirus vector, adenovirus-associated virus vector, etc., which is then administered in a conventional manner. The antisense DNA may be administered as it stands, or may be prepared into a dosage form together with a physiologically acceptable carrier such as an adjuvant to increase its uptake and administered by gene gun or through a catheter such as a catheter with a hydrogel.

In addition, the antisense DNA can also be employed as an oligonucleotide probe for diagnosis to examine the presence of the DNA of the present invention in tissues or cells and the state of its expression.

As in the antisense polynucleotide described above, the double-stranded RNA (siRNA (small (short) interfering RNA), shRNA (small (short) hairpin RNA) to the receptor of the present invention, etc.) containing a part of the RNA encoding the receptor of the present invention, the ribozyme containing a part of the RNA encoding the receptor of the present invention, etc. can suppress the expression of the polynucleotide and can suppress the in vivo functions of the receptor of the present invention or the polynucleotide of the present invention and they can be used as low toxic and safe medicaments such as agents for the prevention/treatment of, for example, mental disorders (e.g., schizophrenia, anxiety, cognitive impairment, panic disorder, phobic disorder, drug-induced psychotic disorder, delusional psychosis, neuroleptic-induced dyskinesia, Parkinson's disease, drug-induced Parkinson's syndrome, extrapyramidal syndrome, etc.), prolactin-related disorders [e.g., hyperprolactinemia (e.g., sterility, galactorrhea, amenorrhea, atrophy of ovary and uterus, etc.), pituitary tumor, diencephalon tumor, menstrual disorder, prolactin hyposecretion (e.g., hypoovarianism, spermatic underdevelopment, menopausal symptoms, hypothyroidism, etc.), etc.], hypertension, sleeping disorders [e.g., primary insomnia, circadian rhythm disorders (e.g., change in physical conditions caused by three-shift work, time zone change syndrome (jet lag), etc.], and the like; preferably as an agent for the prevention/treatment of Parkinson's disease, hyperprolactinemia, etc.

The double-stranded RNA can be manufactured by designing the same based on the sequence of the polynucleotide of the present invention, by modifications of publicly known methods (e.g., Nature, 411, 494, 2001).

The ribozyme can be manufactured by designing the same based on the sequence of the polynucleotide of the present invention, by modifications of publicly known methods (e.g., TRENDS in Molecular Medicine, 7, 221, 2001). For example, the ribozyme can be manufactured by ligating a publicly known ribozyme to a part of the RNA encoding the receptor of the present invention. The part of the RNA encoding the receptor of the present invention includes a contiguous part (RNA fragment) to the cleavage site on the RNA of the present invention, which can be cleaved by a publicly known ribozyme.

Where the double-stranded RNA or ribozyme described above is used as the agent for the prevention/treatment described above, the RNA or ribozyme can be prepared into pharmaceutical preparations, which are provided for administration, as in the antisense polynucleotide.

As in the antisense polynucleotide described above, the aptamers against the receptor of the present invention, etc. can be used as low toxic and safe medicaments such as agents for the prevention/treatment of, for example, mental disorders (e.g., schizophrenia, anxiety, cognitive impairment, panic disorder, phobic disorder, drug-induced psychotic disorder, delusional psychosis, neuroleptic-induced dyskinesia, Parkinson's disease, drug-induced Parkinson's syndrome, extrapyramidal syndrome, etc.), prolactin-related disorders [e.g., hyperprolactinemia (e.g., sterility, galactorrhea, amenorrhea, atrophy of ovary and uterus, etc.), pituitary tumor, diencephalon tumor, menstrual disorder, prolactin hyposecretion (e.g., hypoovarianism, spermatic underdevelopment, menopausal symptoms, hypothyroidism, etc.), etc.], hypertension, sleeping disorders [e.g., primary insomnia, circadian rhythm disorders (e.g., change in physical conditions caused by three-shift work, time zone change syndrome (jet lag), etc.], or the like; preferably as an agent for the prevention/treatment of Parkinson's disease, hyperprolactinemia etc.

The aptamers are prepared by using publicly known methods, for example, the SELEX (systematic evolution of ligands by exponential enrichment) method (Annual Review of Medicine, 56, 555-583, 2005). Structures of aptamers can be determined using publicly known methods; based on the structures, the aptamers are prepared by publicly known methods.

When the aforesaid aptamers are used as medicaments, the aptamers can be prepared into pharmaceutical preparations as in the antisense polynucleotide, and provided for administration.

[6] Medicament Comprising Antibody of the Present Invention

The antibody of the present invention is useful as a low toxic and safe medicament, for example, as an agent for the treatment/prevention of mental disorders (e.g., schizophrenia, anxiety, cognitive impairment, panic disorder, phobic disorder, drug-induced psychotic disorder, delusional psychosis, neuroleptic-induced dyskinesia, Parkinson's disease, drug-induced Parkinson's syndrome, extrapyramidal syndrome, etc.), prolactin-related disorders [e.g., hyperprolactinemia (e.g., sterility, galactorrhea, amenorrhea, atrophy of ovary and uterus, etc.), pituitary tumor, diencephalon tumor, menstrual disorder, prolactin hyposecretion (e.g., hypoovarianism, spermatic underdevelopment, menopausal symptoms, hypothyroidism, etc.), etc.], hypertension, sleeping disorders [e.g., primary insomnia, circadian rhythm disorders (e.g., change in physical conditions caused by three-shift work, time zone change syndrome (jet lag), etc.], or the like; preferably as an agent for the prevention/treatment of Parkinson's disease, hyperprolactinemia, etc.

The medicament comprising the antibody of the present invention described above can be administered to human or other warm-blooded animal (e.g., rats, rabbits, sheep, swine, bovine, cats, dogs, monkeys, etc.) orally or parenterally. The dose may vary depending upon subject to be administered, target disease, conditions, route of administration, etc. When the antibody is used for the purpose of treating a patient with, e.g., Parkinson's disease, it is advantageous to intravenously administer the antibody of the present invention normally at a single dose of about 0.01 to about 20 mg/kg body weight, preferably about 0.1 to about 10 mg/kg body weight, and more preferably about 0.1 to about 5 mg/kg body weight, approximately 1 to 5 times per day, preferably approximately 1 to 3 times per day. In other parenteral administration and oral administration, the antibody can be administered in a dose corresponding to the dose given above. When the condition is especially severe, the dose may be increased according to the condition.

The antibody of the present invention may be administered directly as it stands or as an appropriate pharmaceutical composition. The pharmaceutical composition used for the administration described above contains the aforesaid antibody or salts thereof and pharmacologically acceptable carriers, diluents or excipients. Such a composition is provided in the dosage form suitable for oral or parenteral administration.

That is, examples of the composition for oral administration include solid or liquid dosage form, specifically, tablets (including dragees and film-coated tablets), pills, granules, powdery preparations, capsules (including soft capsules), syrup, emulsions, suspensions, etc. Such a composition is manufactured by publicly known methods and contains a vehicle, a diluent or an excipient conventionally used in the field of pharmaceutical preparations. Examples of the vehicle or excipient for tablets are lactose, starch, sucrose, magnesium stearate, etc.

Examples of the composition for parenteral administration are injectable preparations, suppositories, vaccine, etc. The injectable preparations may include dosage forms such as intravenous, subcutaneous, intracutaneous and intramuscular injections, drip infusions, etc. These injectable preparations may be prepared by methods publicly known. The injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mols) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule. The suppository used for rectal administration may be prepared by blending the aforesaid antibody or its salt with conventional bases for suppositories.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to 500 mg per dosage forms in a unit dose; especially in the form of injection, it is preferred that the aforesaid antibody is contained in about 5 to 100 mg and in about 10 to 250 mg for the other dosage forms.

Each composition described above may further contain other active components unless formulation causes any adverse interaction with the antibody described above.

[7a] Agent for Preventing/Treating Schizophrenia or Cognitive Impairment, which Comprises the Compound or its Salt that Promotes the Activity of the Receptor of the Present Invention or the Ligand of the Present Invention, or the Ligand of the Present Invention The "compound or its salt that promotes the activity of the receptor of the present invention or the ligand of the present invention" may be a compound or its salt that promotes the activity of the receptor of the present invention or the ligand of the present invention (e.g., a peptide, protein, antibody, non-peptide compound, synthetic compound, fermentation product, cell extract, plant extract, animal tissue extract, blood plasma, etc.). The salts of these compounds used are the same salts as those of the receptor of the present invention described above.

When the compound or its salts and the ligand are used as medicaments (as preventive/therapeutic agents, etc.), they can be used in a conventional manner as in the compound or its salts obtained by the screening methods or screening kits of the present invention.

[7b] Agent for Preventing/Treating Prolactin Hyposecretion, which Comprises the Compound or its Salt that Promotes the Activity of the Receptor of the Present Invention or the Ligand of the Present Invention, or the Ligand of the Present Invention The "compound or its salt that promotes the activity of the receptor of the present invention or the ligand of the present invention" may be a compound or its salt that promotes the activity of the receptor of the present invention or the ligand of the present invention (e.g., a peptide, protein, antibody, non-peptide compound, synthetic compound, fermentation product, cell extract, plant extract, animal tissue extract, blood plasma, etc.). These salts used are the same salts as those of the receptor of the present invention described above.

When the compound or its salt and the ligand are used as the medicaments (as preventive/therapeutic agents, etc.), these compounds can be used in a conventional manner as in the compound or its salt obtained by the screening methods or screening kits of the present invention.

[8a] Agent for Preventing/Treating Parkinson's Disease, which Comprises the Compound or its Salt that Inhibits the Activity of the Receptor of the Present Invention or the Ligand of the Present Invention The "compound or its salt that inhibits the activity of the receptor of the present invention or the ligand of the present invention" may be a compound or its salt that inhibits the activity of the receptor of the present invention or the ligand of the present invention (e.g., a peptide, protein, antibody, non-peptide compound, synthetic compound, fermentation product, cell extract, plant extract, animal tissue extract, blood plasma, etc.). These salts used are the same salts as those of the receptor of the present invention described above.

When the compound or its salts are used as the medicaments (as preventive/therapeutic agents, etc.), these compounds can be used in a conventional manner as in the compound or its salts, which are obtained by the screening methods or screening kits of the present invention.

[8b] Agent for Preventing/Treating Hyperprolactinemia, which Comprises the Compound or its Salt that Inhibits the Activity of the Receptor of the Present Invention or the Ligand of the Present Invention The "compound or its salt that inhibits the activity of the receptor of the present invention or the ligand of the present invention" may be a compound or its salt that inhibits the activity of the receptor of the present invention or the ligand of the present invention (e.g., a peptide, protein, antibody, non-peptide compound, synthetic compound, fermentation product, cell extract, plant extract, animal tissue extract, blood plasma, etc.). These salts used are the same salts as those of the receptor of the present invention described above.

When the compound or its salts are used as the medicaments (as preventive/therapeutic agents, etc.), they can be used in a conventional manner as in the compound or its salts, which are obtained by the screening methods or screening kits of the present invention.

[9] DNA Transgenic Animal

The present invention provides a non-human mammal bearing the DNA encoding the receptor of the present invention which is exogenous (hereinafter briefly referred to as the exogenous DNA of the present invention) or its variant DNA (sometimes briefly referred to as the exogenous variant DNA of the present invention).

That is, the present invention provides:
(1) A non-human mammal bearing the exogenous DNA of the present invention or its variant DNA;
(2) The mammal according to (1), wherein the non-human mammal is a rodent;
(3) The mammal according to (2), wherein the rodent is mouse or rat; and,
(4) A recombinant vector containing the exogenous DNA of the present invention or its variant DNA and capable of expressing in a mammal; etc.

The non-human mammal bearing the exogenous DNA of the present invention or its variant DNA (hereinafter briefly referred to as the DNA transgenic animal of the present invention) can be produced by transferring a desired DNA into an unfertilized egg, a fertilized egg, a spermatozoon, a germinal cell containing a primordial germinal cell thereof, etc., preferably in the embryogenic stage in the development of a non-human mammal (more preferably in the single cell or fertilized cell stage and generally before the 8-cell phase), by means, such as the calcium phosphate method, the electric pulse method, the lipofection method, the agglutination method, the microinjection method, the particle gun method, the DEAE-dextran method, etc. Also, it is possible to transfer the exogenous DNA of the present invention into a somatic cell, a living organ, a tissue cell, etc. by the DNA transfer, and utilize the transformant for cell culture, tissue culture, etc. In addition, these cells may be fused with the above-described germinal cell by a publicly known cell fusion method to prepare the DNA transgenic animal of the present invention.

Examples of the non-human mammals that can be used include bovine, swine, sheep, goat, rabbits, dogs, cats, guinea pigs, hamsters, mice, rats, etc. Above all, preferred are rodents, especially mice (e.g., C57BL/6 strain, DBA2 strain, etc. for a pure line and for a cross line, $B6C3F_1$ strain, $BDF_1$ strain $B6D2F_1$ strain, BALB/c strain, ICR strain, etc.), rats (Wistar, SD, etc.) or the like, since they are relatively short in ontogeny and life cycle from a standpoint of producing model animals for human disease.

"Mammal" in a recombinant vector that can be expressed in the mammal includes the aforesaid non-human mammal and human.

The exogenous DNA of the present invention refers to the DNA of the present invention that is once isolated/extracted from a mammal, not the DNA of the present invention inherently possessed by a non-human mammal.

The mutant DNA of the present invention includes mutants resulting from variation (e.g., mutation, etc.) in the base sequence of the original DNA of the present invention, specifically DNAs resulting from base addition, deletion, substitution with other bases, etc. and further includes abnormal DNA.

The abnormal DNA is intended to mean such a DNA that expresses the abnormal receptor of the present invention and exemplified by the DNA that expresses the polypeptide to suppress the function of normal receptor of the present invention.

The exogenous DNA of the present invention may be any one of those derived from a mammal of the same species as or a different species from the target animal. In transferring the DNA of the present invention, it is generally advantageous to use the DNA as a DNA construct in which the DNA is ligated downstream a promoter capable of expressing the DNA in the target animal. For example, in the case of transferring the human DNA of the present invention, a DNA transgenic mammal that expresses the DNA of the present invention to a high level, can be prepared by microinjecting a DNA construct (e.g., vector, etc.) of the human DNA of the present invention ligated downstream of various promoters which are capable of expressing the DNA derived from various mammals (e.g., rabbits, dogs, cats, guinea pigs, hamsters, rats, mice, etc.) bearing the DNA of the present invention highly homologous to the human DNA into a fertilized egg of the target non-human mammal, for example, a fertilized egg of a mouse.

As expression vectors for the receptor of the present invention, there are *Escherichia coli*-derived plasmids, *Bacillus subtilis*-derived plasmids, yeast-derived plasmids, bacteriophages such as λ phage, retroviruses such as Moloney leukemia virus, etc., and animal viruses such as vaccinia virus, baculovirus, etc. Of these vectors, *Escherichia coli*-derived plasmids, *Bacillus subtilis*-derived plasmids, or yeast-derived plasmids, etc. are preferably used.

Examples of these promoters for regulating the DNA expression include (i) promoters for DNA derived from viruses (e.g., simian virus, cytomegalovirus, Moloney leukemia virus, JC virus, breast cancer virus, poliovirus, etc.), and (ii) promoters derived from various mammals (human, rabbits, dogs, cats, guinea pigs, hamsters, rats, mice, etc.), for example, promoters of albumin, insulin II, uroplakin II, elastase, erythropoietin, endothelin, muscular creatine kinase, glial fibrillary acidic protein, glutathione S-transferase, platelet-derived growth factor β, keratins K1, K10 and K14, collagen types I and II, cyclic AMP-dependent protein kinase βI subunit, dystrophin, tartarate-resistant alkaline phosphatase, atrial natriuretic factor, endothelial receptor tyrosine kinase (generally abbreviated as Tie2), sodium-potassium adenosine triphosphorylase (Na,K-ATPase), neurofilament light chain, metallothioneins I and IIA, metalloproteinase I tissue inhibitor, MHC class I antigen (H-2L), H-ras, renin, dopamine β-hydroxylase, thyroid peroxidase (TPO), polypeptide chain elongation factor 1α (EF-1α), β actin, α and β myosin heavy chains, myosin light chains 1 and 2, myelin base protein, thyroglobulins, Thy-1, immunoglobulins, H-chain variable region (VNP), serum amyloid component P, myoglobin, troponin C, smooth muscle α actin, preproencephalin A, vasopressin, etc. Among them, cytomegalovirus promoters, human polypeptide elongation factor 1α (EF-1α) promoters, human and fowl β actin promoters, etc., which are capable of high expression in the whole body are preferred.

Preferably, the vectors described above have a sequence that terminates the transcription of the desired messenger RNA in the DNA transgenic animal (generally termed a terminator); for example, a sequence of each DNA derived from viruses and various mammals, and SV40 terminator of the simian virus, and the like are preferably used.

In addition, for the purpose of increasing the expression of the desired exogenous DNA to a higher level, the splicing signal and enhancer region of each DNA, a portion of the intron of an eukaryotic DNA may also be ligated at the 5' upstream of the promoter region, or between the promoter region and the translational region, or at the 3' downstream of the translational region, depending upon purposes.

The translational region for the normal receptor of the present invention can be obtained using as a starting material the entire genomic DNA or its portion of liver, kidney, thyroid cell or fibroblast origin from human or various mammals (e.g., rabbits, dogs, cats, guinea pigs, hamsters, rats, mice, etc.) or of various commercially available genomic DNA libraries, or using cDNA prepared by a publicly known method from RNA of liver, kidney, thyroid cell or fibroblast origin as a starting material. Also, an exogenous abnormal DNA can produce the translational region through variation of the translational region of the normal polypeptide obtained from the cells or tissues described above by point mutagenesis.

The translational region can be prepared by a conventional DNA engineering technique, in which the DNA is ligated downstream the aforesaid promoter and if desired, upstream the translation termination site, as a DNA construct capable of being expressed in the transgenic animal.

The exogenous DNA of the present invention is transferred at the fertilized egg cell stage in a manner such that the DNA is certainly present in all the germinal cells and somatic cells of the target mammal. The fact that the exogenous DNA of the present invention is present in the germinal cells of the animal prepared by DNA transfer means that all offspring of the prepared animal will maintain the exogenous DNA of the present invention in all of the germinal cells and somatic cells thereof. The offspring of the animal that inherits the exogenous DNA of the present invention also have the exogenous DNA of the present invention in all of the germinal cells and somatic cells thereof.

The non-human mammal in which the normal exogenous DNA of the present invention has been transferred can be passaged as the DNA-bearing animal under ordinary rearing environment, by confirming that the exogenous DNA is stably retained by crossing.

By transfer of the exogenous DNA of the present invention at the fertilized egg cell stage, the DNA is retained to be excess in all of the germinal and somatic cells. The fact that the exogenous DNA of the present invention is excessively present in the germinal cells of the prepared animal after transfer means that the DNA of the present invention is excessively present in all of the germinal cells and somatic cells thereof. The offspring of the animal that inherits the exogenous DNA of the present invention have excessively the DNA of the present invention in all of the germinal cells and somatic cells thereof.

It is possible to obtain homozygous animals having the transferred DNA in both homologous chromosomes and breed male and female of the animal so that all the progeny have this DNA in excess.

In a non-human mammal bearing the normal DNA of the present invention, the normal DNA of the present invention has expressed at a high level, and may eventually develop hyperfunction in the function of the receptor of the present invention by promoting the function of endogenous normal DNA. Therefore, the animal can be utilized as a pathologic model animal for the disease. For example, using the normal DNA transgenic animal of the present invention, it is possible to elucidate the mechanism of hyperfunction in the function of the receptor of the present invention and the pathological mechanism of the disease associated with the receptor of the present invention and to investigate how to treat these diseases.

Furthermore, since a transgenic mammal with the exogenous normal DNA of the present invention exhibits symptoms of increasing the receptor of the present invention, the animal is usable in a test for screening the agent for the prevention/treatment of diseases associated with the receptor of the present invention [for example, mental disorders (e.g., schizophrenia, anxiety, cognitive impairment, panic disorder, phobic disorder, drug-induced psychotic disorder, delusional psychosis, neuroleptic-induced dyskinesia, Parkinson's disease, drug-induced Parkinson's syndrome, extrapyramidal syndrome, etc.), prolactin-related disorders [e.g., hyperprolactinemia (e.g., sterility, galactorrhea, amenorrhea, atrophy of ovary and uterus, etc.), pituitary tumor, diencephalon tumor, menstrual disorder, prolactin hyposecretion (e.g., hypoovarianism, spermatic underdevelopment, menopausal symptoms, hypothyroidism, etc.), etc.], hypertension, sleeping disorders [e.g., primary insomnia, circadian rhythm disorders (e.g., change in physical conditions caused by three-shift work, time zone change syndrome (jet lag), etc.], or the like].

On the other hand, a non-human mammal having the exogenous abnormal DNA of the present invention can be passaged under normal breeding conditions as the DNA-bearing animal by confirming stable retention of the exogenous DNA via crossing. Furthermore, the exogenous DNA of interest can be utilized as a starting material after inserting the DNA into the plasmid described above. The DNA construct with a promoter can be prepared by conventional DNA engineering techniques. The transfer of the abnormal DNA of the present invention at the fertilized egg cell stage is preserved to be present in all of the germinal and somatic cells of the target mammal. The fact that the abnormal DNA of the present invention is present in the germinal cells of the animal after DNA transfer means that all of the offspring of the prepared animal have the abnormal DNA of the present invention in all of the germinal and somatic cells. Such an offspring that passaged the exogenous DNA of the present invention will have the abnormal DNA of the present invention in all of the germinal and somatic cells. A homozygous animal having the introduced DNA on both of homologous chromosomes can be acquired, and by crossing these male and female animals, all the offspring can be bred to retain the DNA.

In a non-human mammal bearing the abnormal DNA of the present invention, the abnormal DNA of the present invention has expressed to a high level, and may eventually develop the function inactive type inadaptability to the receptor of the present invention by inhibiting the functions of endogenous normal DNA. Therefore, the animal can be utilized as a pathologic model animal for the disease. For example, using the abnormal DNA transgenic animal of the present invention, it is possible to elucidate the pathological mechanism of the function inactive type inadaptability to the receptor of the present invention and to investigate how to treat the disease.

Specifically, the transgenic animal of the present invention expressing the abnormal DNA at a high level is expected to serve as an experimental model to elucidate the mechanism of the functional inhibition (dominant negative effect) of normal polypeptide or receptor by the abnormal polypeptide of the present invention or the abnormal receptor of the present invention in the function inactive type inadaptability of the receptor of the present invention.

A mammal bearing the abnormal exogenous DNA of the present invention has a symptom increasing the receptor of the present invention and is thus also expected to serve for screening a candidate drug for the treatment of the function inactive type inadaptability of the receptor of the present invention.

Other potential applications of two kinds of the DNA transgenic animals of the present invention described above further include, for example:

(i) use as a cell source for tissue culture;
(ii) elucidation of the relation to the polypeptide or receptor that is specifically expressed or activated by the receptor of the present invention, through direct analysis of DNA or RNA in tissues of the DNA transgenic animal of the present invention or through analysis of tissues of the polypeptide or receptor expressed by the DNA;
(iii) research on the function of cells derived from tissues that are usually cultured only with difficulty, using cells in tissues bearing the DNA cultured by a standard tissue culture technique;
(iv) screening a medicament that enhances the functions of cells using the cells described in (iii) above; and,
(v) isolation and purification of the variant polypeptide or the receptor of the present invention and preparation of an antibody thereto; etc.

Furthermore, clinical conditions of the diseases associated with the receptor of the present invention, including the function inactive type inadaptability to the receptor of the present invention [for example, mental disorders (e.g., schizophrenia, anxiety, cognitive impairment, panic disorder, phobic disorder, drug-induced psychotic disorder, delusional psychosis, neuroleptic-induced dyskinesia, Parkinson's disease, drug-induced Parkinson's syndrome, extrapyramidal syndrome, etc.), prolactin-related disorders [e.g., hyperprolactinemia (e.g., sterility, galactorrhea, amenorrhea, atrophy of ovary and uterus, etc.), pituitary tumor, diencephalon tumor, menstrual disorder, prolactin hyposecretion (e.g., hypoovarianism, spermatic underdevelopment, menopausal symptoms, hypothyroidism, etc.), etc.], hypertension, sleeping disorders [e.g., primary insomnia, circadian rhythm disorders (e.g., change in physical conditions caused by three-shift work, time zone change syndrome (jet lag), etc.], and the like] can be determined by using the DNA transgenic animal of the present invention. Also, pathological findings on each organ in a disease model associated with the receptor of the present invention can be obtained in more detail, leading to the development of a new method for treatment as well as the research and therapy of any secondary diseases associated with the diseases.

It is also possible to obtain a liberated DNA-transferred cell by excising each organ from the DNA transgenic animal of the present invention, mincing the organ and degrading with a proteinase such as trypsin, etc., followed by establishing the line of its culture or cultured cells. Furthermore, the DNA transgenic animal can serve to identify cells capable of producing the receptor of the present invention, and to study the relation to apoptosis, differentiation or proliferation or the mechanism of signal transduction in these properties to inspect any abnormality therein. Thus, the DNA transgenic animal can provide an effective research material for the receptor of the present invention and for investigation of its function and effect.

To develop medicaments for treating the diseases associated with the receptor of the present invention, including the function inactive type inadaptability to the receptor of the present invention, using the DNA transgenic animal of the present invention, an effective and rapid method for screening can be provided by using the method for inspection and the method for quantification, etc. described above. It is also possible to investigate and develop a method for DNA therapy for treating the diseases associated with the receptor of the present invention, using the DNA transgenic animal of the present invention or a vector capable of expressing the exogenous DNA of the present invention.

[10] Knockout Animal

The present invention provides a non-human mammalian embryonic stem cell bearing the DNA of the present invention inactivated and a non-human mammal deficient in expressing the DNA of the present invention.

Thus, the present invention provides:

(1) a non-human mammalian embryonic stem cell in which the DNA of the present invention is inactivated;
(2) the embryonic stem cell according to (1), wherein the DNA is inactivated by introducing a reporter gene (e.g., β-galactosidase gene derived from *Escherichia coli*);
(3) the embryonic stem cell according to (1), which is resistant to neomycin;
(4) the embryonic stem cell according to (1), wherein the non-human mammal is a rodent;
(5) the embryonic stem cell according to (4), wherein the rodent is mouse;
(6) a non-human mammal deficient in expressing the DNA of the present invention, wherein the DNA is inactivated;
(7) the non-human mammal according to (6), wherein the DNA is inactivated by inserting a reporter gene (e.g., β-galactosidase derived from *Escherichia coli*) therein and the reporter gene is capable of being expressed under control of a promoter for the DNA of the present invention;
(8) the non-human mammal according to (6), which is a rodent;
(9) the non-human mammal according to (8), wherein the rodent is mouse; and,
(10) a method of screening a compound or its salt that promotes or inhibits the activity of a promoter for the DNA of the present invention, which comprises administering a test compound to the mammal of (7) and detecting expression of the reporter gene.

The non-human mammalian embryonic stem cell in which the DNA of the present invention is inactivated refers to a non-human mammalian embryonic stem cell (hereinafter abbreviated as ES cell) that suppresses the ability of the non-human mammal to express the DNA by artificially mutating the DNA of the present invention, or the DNA has no substantial ability to express the receptor of the present invention (hereinafter sometimes referred to as the knockout DNA of the present invention) by substantially inactivating the activities of the receptor of the present invention encoded by the DNA.

Examples of the non-human mammal used are the same as those given above.

Techniques for artificially mutating the DNA of the present invention include deletion of a part or all of the DNA sequence and insertion of or substitution with other DNA, by genetic engineering. By these variations, the knockout DNA of the present invention may be prepared, for example, by shifting the reading frame of a codon or by disrupting the function of a promoter or exon.

Specifically, the non-human mammalian embryonic stem cell, in which the DNA of the present invention is inactivated (hereinafter merely referred to as the ES cell with the DNA of the present invention inactivated or the knockout ES cell of the present invention), can be obtained by, for example, isolating the DNA of the present invention that the desired non-human mammal possesses, inserting a drug resistant gene such as a neomycin resistant gene or a hygromycin resistant gene, or a reporter gene such as lacZ (β-galactosidase gene) or cat (chloramphenicol acetyltransferase gene), etc. into its exon region thereby to disable the functions of exon, or integrating to a chromosome of the target animal by, e.g., homologous recombination, a DNA sequence that terminates gene transcription (e.g., polyA additional signal, etc.) in the intron between exons, thus inhibiting the synthesis of complete messenger RNA and eventually destroying the gene (hereinafter briefly referred to as a targeting vector). The thus-obtained ES cells to the southern hybridization analysis with a DNA sequence on or near the DNA of the present invention as a probe, or to PCR analysis with a DNA sequence on the targeting vector and another DNA sequence near the DNA of the present invention which is not included in the targeting vector as primers, to select the knockout ES cell of the present invention.

The parent ES cells to inactivate the DNA of the present invention by homologous recombination, etc. may be of a strain already established as described above, or may originally be established in accordance with a modification of the known method by Evans and Kaufman described above. For example, in the case of mouse ES cells, currently it is common practice to use ES cells of the 129 strain. However, since their immunological background is obscure, the C57BL/6 mouse or the BDF$_1$ mouse (F$_1$ hybrid between C57BL/6 and DBA/2), wherein the low ovum availability per C57BL/6 in the C57BL/6 mouse has been improved by crossing with DBA/2, may be preferably used, for the purpose of obtaining a pure line of ES cells with the clear immunological genetic background instead of the ES cells of the 129 strain and for other purposes. The BDF$_1$ mouse is advantageous in that, when a pathologic model mouse is generated using ES cells obtained therefrom, the genetic background can be changed to that of the C57BL/6 mouse by back-crossing with the C57BL/6 mouse, since its background is of the C57BL/6 mouse, as well as being advantageous in that ovum availability per animal is high and ova are robust.

In establishing ES cells, blastocysts at 3.5 days after fertilization are commonly used, and embryos are preferably collected at the 8-cell stage, after culturing until the blastocyst stage, the embryos are used to efficiently obtain a large number of early stage embryos.

Although the ES cells used may be of either sex, male ES cells are generally more convenient for generation of a germ cell line chimera. It is also desirable that sexes are identified as soon as possible to save painstaking incubation time.

Methods for sex identification of the ES cell include the method in which a gene in the sex-determining region on the Y-chromosome is amplified by the PCR process and detected. When this method is used, one colony of ES cells (about 50 cells) is sufficient for sex-determination analysis, whereas karyotype analysis requires about $10^6$ cells; therefore, the first selection of ES cells at the early stage of culture can be based on sex identification, and male cells can be selected early, which saves a significant amount of time at the early stage of culture.

Also, second selection can be achieved by, for example, confirmation of the number of chromosomes by the G-banding method. It is usually desirable that the chromosome number of the obtained ES cells be 100% of the normal number. However, when it is difficult to obtain the cells having the normal number of chromosomes due to physical operations, etc. in the cell establishment, it is desirable that the ES cell is again cloned to a normal cell (e.g., in a mouse cell having the number of chromosomes being 2n=40) after knockout of the gene of the ES cells.

Although the embryonic stem cell line thus obtained shows a very high growth potential, it must be subcultured with great care, since it tends to lose its ontogenic capability. For example, the embryonic stem cell line is cultured at about 37° C. in a carbon dioxide incubator (preferably 5% carbon dioxide and 95% air, or 5% oxygen, 5% carbon dioxide and 90% air) in the presence of LIF (1 to 10000 U/ml) on appropriate feeder cells such as STO fibroblasts, treated with a trypsin/EDTA solution (normally 0.001 to 0.5% trypsin/0.1 to about 5 mM EDTA, preferably about 0.1% trypsin/1 mM EDTA) at the time of passage to obtain separate single cells, which are then plated on freshly prepared feeder cells. This passage is normally conducted every 1 to 3 days; it is desirable that cells be observed at the passage and cells found to be morphologically abnormal in culture, if any, be abandoned.

Where ES cells are allowed to reach a high density in mono-layers or to form cell aggregates in suspension under appropriate conditions, it is possible to differentiate the ES cells to various cell types, for example, pariental and visceral muscles, cardiac muscle, or the like [M. J. Evans and M. H. Kaufman, Nature, 292, 154, 1981; G. R. Martin, Proc. Natl. Acad. Sci. U.S.A., 78, 7634, 1981; T. C. Doetschman et al., Journal of Embryology Experimental Morphology, 87, 27, 1985]. The cells deficient in expression of the DNA of the present invention, which are obtained from the differentiated ES cells of the present invention, are useful for cytological study of the receptor of the present invention in vitro.

The non-human mammal deficient in expression of the DNA of the present invention can be identified from a normal animal by measuring the mRNA level in the subject animal by a publicly known method, and indirectly comparing the degrees of expression.

Examples of the non-human mammal used are the same as those given above.

With respect to the non-human mammal deficient in expression of the DNA of the present invention, the DNA of the present invention can be made knockout by transferring a targeting vector, prepared as described above, to mouse embryonic stem cells or mouse oocytes, and conducting homologous recombination in which a targeting vector DNA sequence, wherein the DNA of the present invention is inactivated by the transfer, is replaced with the DNA of the present invention on a chromosome of a mouse embryonic stem cell or mouse embryo.

The knockout cells with the disrupted DNA of the present invention can be identified by the Southern hybridization analysis using as a probe a DNA fragment on or near the DNA of the present invention, or by the PCR analysis using as primers a DNA sequence on the targeting vector and another DNA sequence at the proximal region of other than the DNA of the present invention derived from mouse used in the targeting vector. When non-human mammal stem cells are used, a cell line wherein the DNA of the present invention is inactivated by homologous recombination is cloned; the resulting clones are injected to, e.g., a non-human mammalian embryo or blastocyst, at an appropriate stage such as the 8-cell stage. The resulting chimeric embryos are transplanted to the uterus of the pseudopregnant non-human mammal. The resulting animal is a chimeric animal constructed with both cells having the normal locus of the DNA of the present invention and those having an artificially mutated locus of the DNA of the present invention.

When some germ cells of the chimeric animal have a mutated locus of the DNA of the present invention, an individual, which entire tissue is composed of cells having a mutated locus of the DNA of the present invention can be selected from a series of offspring obtained by crossing between such a chimeric animal and a normal animal, e.g., by coat color identification, etc. The individuals thus obtained are normally deficient in heterozygous expression of the receptor of the present invention. The individuals deficient in homozygous expression of the receptor of the present invention can be obtained from offspring of the intercross between those deficient in heterozygous expression of the receptor of the present invention.

When an oocyte is used, a DNA solution may be injected, e.g., into the prenucleus by microinjection thereby to obtain a transgenic non-human mammal having a targeting vector introduced in its chromosome. From such transgenic non-human mammals, those having a mutation at the locus of the DNA of the present invention can be obtained by selection based on homologous recombination.

As described above, the individuals in which the DNA of the present invention is rendered knockout permit passage rearing under ordinary rearing conditions, after the individuals obtained by their crossing have proven to have been knockout.

Furthermore, the genital system may be obtained and retained by conventional methods. That is, by crossing male and female animals each having the inactivated DNA, homozygous animals having the inactivated DNA in both loci can be obtained. The homozygotes thus obtained may be reared so that one normal animal and two or more homozygotes are produced from a mother animal to efficiently obtain such homozygotes. By crossing male and female heterozygotes, homozygotes and heterozygotes having the inactivated DNA are proliferated and passaged.

The non-human mammalian embryonic stem cell, in which the DNA of the present invention is inactivated, is very useful for preparing a non-human mammal deficient in expression of the DNA of the present invention.

Since the non-human mammal, in which the DNA of the present invention is inactivated, lacks various biological activities derived from the receptor of the present invention, such an animal can be a disease model suspected of inactivated biological activities of the receptor of the present invention and thus, offers an effective study to investigate the causes for and therapy for these diseases.

The present invention provides a method of screening the compound or its salt that promotes or inhibits the activity of a promoter for the DNA of the present invention, which comprises administering a test compound to a non-human mammal deficient in expression of the DNA of the present invention and detecting expression of the reporter gene.

In the screening methods described above, an animal in which the DNA of the present invention is inactivated by introducing a reporter gene and the reporter gene is expressed under control of a promoter for the DNA of the present invention is used as the non-human mammal deficient in expression of the DNA of the present invention, which is selected from the aforesaid non-human mammals deficient in expression of the DNA of the present invention.

Examples of the test compound are the same as those described above.

Examples of the reporter gene used are the same as those described above, and preferred are β-galactosidase (lacZ), soluble alkaline phosphatase gene, luciferase gene and the like.

Since the reporter gene is present under control of a promoter for the DNA of the present invention in the non-human mammal deficient in expression of the DNA of the present invention wherein the DNA of the present invention is substituted with the reporter gene, the activity of the promoter can be detected by tracing the expression of a substance encoded by the reporter gene.

When a part of the DNA region encoding the receptor of the present invention is substituted with, e.g., β-galactosidase gene (lacZ) derived from *Escherichia coli*, β-galactosidase is expressed in a tissue where the receptor of the present invention should originally be expressed, instead of the receptor of the present invention. Thus, the expression state of the receptor of the present invention can be readily observed with an animal in vivo by staining with a reagent, e.g., 5-bromo-4-chloro-3-indolyl-β-galactopyranoside (X-gal) which is a substrate for β-galactosidase. Specifically, a mouse deficient in the receptor of the present invention, or its tissue section is fixed with glutaraldehyde, etc. After washing with phosphate buffered saline (PBS), the system is reacted with a staining solution containing X-gal at room temperature or about 37° C. for approximately 30 minutes to an hour. The β-galactosidase reaction is terminated by washing the tissue preparation with 1 mM EDTA/PBS solution, and the color formed is observed. Alternatively, mRNA encoding lacZ may be detected in a conventional manner.

The compound or its salt, which is obtained using the screening methods described above, is a compound selected from the test compounds described above, which promotes or inhibits the activity of a promoter for the DNA of the present invention.

The compound obtained by the screening method above may form salts, and may be used in the form of salts with physiologically acceptable acids (e.g., inorganic acids, etc.) or bases (e.g., organic acids, etc.), preferably in the form of physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

The compound or its salt that promotes the activity of a promoter for the DNA of the present invention can promote the expression of the receptor of the present invention to promote the activity or function of the receptor of the present invention. Therefore, the compound or its salt can be used as a low toxic and safe medicament, such as an agent for the prevention/treatment of diseases, for example, mental disorders (e.g., schizophrenia, anxiety, cognitive impairment, panic disorder, phobic disorder, drug-induced psychotic disorder, delusional psychosis, neuroleptic-induced dyskinesia, Parkinson's disease, drug-induced Parkinson's syndrome, extrapyramidal syndrome, etc.), prolactin-related disorders hyperprolactinemia (e.g., sterility, galactorrhea, amenorrhea, atrophy of ovary and uterus, etc.), pituitary tumor, diencephalon tumor, menstrual disorder, prolactin hyposecretion (e.g., hypoovarianism, spermatic underdevelopment, menopausal symptoms, hypothyroidism, etc.), etc.], hypertension, sleeping disorders [e.g., primary insomnia, circadian rhythm disorders (e.g., change in physical conditions caused by three-shift work, time zone change syndrome (jet lag), etc.], or the like; especially schizophrenia, cognitive impairment, prolactin hyposecretion, and the like.

The compound or its salt that inhibits the activity of a promoter for the DNA of the present invention can inhibit the expression of the receptor of the present invention to inhibit the activity or function of the receptor of the present invention, and can be used as a low toxic and safe medicament such as an agent for the prevention/treatment of diseases, for example, mental disorders (e.g., schizophrenia, anxiety, cognitive impairment, panic disorder, phobic disorder, drug-induced psychotic disorder, delusional psychosis, neuroleptic-induced dyskinesia, Parkinson's disease, drug-induced Parkinson's syndrome, extrapyramidal syndrome, etc.), prolactin-related disorders [e.g., hyperprolactinemia (e.g., sterility, galactorrhea, amenorrhea, atrophy of ovary and uterus, etc.), pituitary tumor, diencephalon tumor, menstrual disorder, prolactin hyposecretion (e.g., hypoovarianism, spermatic underdevelopment, menopausal symptoms, hypothyroidism, etc.), etc.], hypertension, sleeping disorders [e.g., primary insomnia, circadian rhythm disorders (e.g., change in physical conditions caused by three-shift work, time zone change syndrome (jet lag), etc.], or the like; preferably Parkinson's disease, hyperprolactinemia, etc.

In addition, compounds derived from the compounds obtained by the screening described above can be used as well.

The medicament comprising the compound or its salt obtained by the above screening methods can be manufactured as in the medicament comprising the compound or its salt obtained by the screening methods of the present invention described above.

The pharmaceutical preparation thus obtained is safe and low toxic, and can be administered to, for example, human or other mammal (e.g., rat, mouse, guinea pig, rabbit, sheep, swine, bovine, horse, cat, dog, monkey, etc.).

The dose of the compound or its salt that promotes the activity of a promoter for the DNA of the present invention may vary depending on subject to be administered, target disease, route for administration, etc.; in oral administration of the compound for the treatment of, e.g., schizophrenia, the compound is administered to an adult (as 60 kg body weight) normally at a daily dose of about 0.1 mg to about 100 mg, preferably about 1.0 to about 50 mg, and more preferably about 1.0 to about 20 mg. In parenteral administration, the dose of the compound may vary depending on subject to be administered, target disease, conditions, route for administration, etc. When the compound is administered in the form of an injectable preparation for the treatment of, e.g., schizophrenia, the compound is advantageously administered intravenously to an adult (as 60 kg body weight) normally at a daily dose of about 0.01 to about 30 mg, preferably about 0.1 to about 20 mg, and more preferably about 0.1 to about 10 mg. For other animal species, the corresponding dose as converted per 60 kg body weight can be administered.

On the other hand, for example, when the compound that inhibits the promoter activity for the DNA of the present invention is orally administered, the compound is administered to the adult patient (as 60 kg body weight) with Parkinson's disease normally in a daily dose of about 0.1 to 100 mg, preferably about 1.0 to 50 mg and more preferably about 1.0 to 20 mg. In parenteral administration, a single dose of the compound varies depending on subject to be administered, target disease, etc. For example, when the compound that inhibits the promoter activity for the DNA of the present invention is administered to the adult patient (as 60 kg body weight) with schizophrenia in the form of injectable preparation, it is advantageous to administer the compound intravenously to the patient in a daily dose of about 0.01 to about 30 mg, preferably about 0.1 to about 20 mg and more preferably about 0.1 to about 10 mg. For other animal species, the corresponding dose as converted per 60 kg weight can be administered.

As stated above, the non-human mammal deficient in expression of the DNA of the present invention is extremely useful for screening the compound or its salt that promotes or inhibits the activity of a promoter for the DNA of the present invention and can greatly contribute to elucidation of causes for various diseases derived from deficiency in expression of the DNA of the present invention and for the development of preventive/therapeutic drugs for these diseases.

Also, a so-called transgenic animal (gene transferred animal) can be prepared by using a DNA containing the promoter region of the receptor of the present invention, ligating genes encoding various proteins at the downstream and injecting the same into oocyte of an animal. It is thus possible to synthesize the polypeptide specifically and study its activity in vivo. When an appropriate reporter gene is ligated to the promoter site described above and a cell line that expresses the gene is established, the resulting system can be utilized as the search system for a low molecular compound having the action of specifically promoting or inhibiting (suppressing) in vivo productivity of the receptor of the present invention itself.

In the specification and drawings, where bases, amino acids, etc. are shown by their codes, these codes are denoted in accordance with the IUPAC-IUB Commission on Biochemical Nomenclature or by the common codes in the art, examples of which are given below. For amino acids that may have the optical isomer, L form is presented unless otherwise indicated.

DNA: deoxyribonucleic acid
cDNA: complementary deoxyribonucleic acid
A: adenine
T: thymine
G: guanine
C: cytosine
RNA: ribonucleic acid
mRNA: messenger ribonucleic acid
dATP: deoxyadenosine triphosphate
dTTP: deoxythymidine triphosphate
dGTP: deoxyguanosine triphosphate
dCTP: deoxycytidine triphosphate
ATP: adenosine triphosphate
EDTA: ethylenediaminetetraacetic acid
SDS: sodium dodecyl sulfate
Gly: glycine
Ala: alanine
Val: valine
Leu: leucine
Ile: isoleucine
Ser: serine
Thr: threonine
Cys: cysteine
Met: methionine
Glu: glutamic acid
Asp: aspartic acid
Lys: lysine
Arg: arginine
His: histidine
Phe: phenylalanine
Tyr: tyrosine
Trp: tryptophan
Pro: proline
Asn: asparagine
Gln: glutamine
pGlu: pyroglutamic acid
Sec: selenocysteine Substituents, protecting groups and reagents frequently used in this specification are presented by the codes described below.

Me: methyl group
Et: ethyl group
Bu: butyl group
Ph: phenyl group
TC: thiazolidine-4(R)-carboxamido group
Tos: p-toluenesulfonyl
CHO: formyl
Bzl: benzyl
$Cl_2$-Bzl: 2,6-dichlorobenzyl
Bom: benzyloxymethyl
Z: benzyloxycarbonyl
Cl-Z: 2-chlorobenzyloxycarbonyl
Br-Z: 2-bromobenzyl oxycarbonyl
Boc: t-butoxycarbonyl
DNP: dinitrophenol
Trt: trityl
Bum: t-butoxymethyl
Fmoc: N-9-fluorenyl methoxycarbonyl
HOBt: 1-hydroxybenztriazole
HOOBt: 3,4-dihydro-3-hydroxy-4-oxo-1,2,3-benzotriazine
HONB: 1-hydroxy-5-norbornene-2,3-dicarboxylmide
DCC: N,N'-dicyclohexylcarbodiimide The sequence identification numbers in the sequence listing of the specification indicate the following sequences.

[SEQ ID NO: 1]
This shows the amino acid sequence of human GPR52.
[SEQ ID NO: 2]
This shows the base sequence of cDNA encoding human GPR52.
[SEQ ID NO: 3]
This shows the amino acid sequence of rat GPR52.
[SEQ ID NO: 4]
This shows the base sequence of cDNA encoding rat GPR52.
[SEQ ID NO: 5]
This shows the amino acid sequence of mouse GPR52.
[SEQ ID NO: 6]
This shows the base sequence of cDNA encoding mouse GPR52.
[SEQ ID NO: 7]
This shows the base sequence of primer 1 used in EXAMPLE 1 and EXAMPLE 2.
[SEQ ID NO: 8]
This shows the base sequence of primer 2 used in EXAMPLE 1 and EXAMPLE 2.
[SEQ ID NO: 9]
This shows the base sequence of primer 1 used in EXAMPLE 6.
[SEQ ID NO: 10]
This shows the base sequence of primer 2 used in EXAMPLE 6.
[SEQ ID NO: 11]
This shows the base sequence of probe 1 used in EXAMPLE 6 [FAM (6-carboxy-fluorescein) was labeled at the 5' end as a reporter dye and TAMRA (6-carboxy-tetramethyl-rhodamine) at the 3' end as a quencher].
[SEQ ID NO: 12]
This shows the base sequence of primer 3 used in EXAMPLE 6.
[SEQ ID NO: 13]
This shows the base sequence of primer 4 used in EXAMPLE 6.
[SEQ ID NO: 14]
This shows the base sequence of probe 2 used in EXAMPLE 6 [FAM (6-carboxy-fluorescein) was labeled at the 5' end as a reporter dye and TAMRA (6-carboxy-tetramethyl-rhodamine) at the 3' end as a quencher].
[SEQ ID NO: 15]
This shows the base sequence of primer 5 used in EXAMPLE 6.
[SEQ ID NO: 16]
This shows the base sequence of primer 6 used in EXAMPLE 6.

[SEQ ID NO: 17]

This shows the base sequence of probe 3 used in EXAMPLE 6 [FAM (6-carboxy-fluorescein) was labeled at the 5' end as a reporter dye and TAMPA (6-carboxy-tetramethyl-rhodamine) at the 3' end as a quencher].

EXAMPLES

Hereinafter, the present invention will be described in more detail with reference to REFERENCE EXAMPLE and EXAMPLES but is not deemed to be limited thereto.

Reference Example 1

Preparation of Human GPR52 Expression CHO Cell Line

The DNA fragment encoding human GPR52 was cloned from MTC panels (Clontech) using PCR in accordance with the sequence described in Molecular Brain Research, 64, 193-198, 1999. The base sequence was analyzed so that the base sequence (SEQ ID NO: 2) of cDNA encoding human GPR52 having the amino acid sequence represented by SEQ ID NO: 1 was obtained. The resulting DNA fragment was introduced into the SalI/SpeI sites of pAKKO-111 vector [Biochem. Biophys. Acta, 1219, 251 (1994)] to construct the expression plasmid. Subsequently, the expression plasmid was transfected to CHO (dhfr$^-$) cells by publicly known methods, and the expression plasmid-transfected cells were selected in thymidine-free medium to obtain the human GPR52 stable expression cells.

Example 1

Cloning of Rat GPR52

Using rat (SD) brain cDNA (BD Biosciences) as a template, PCR was performed using primer 1 (SEQ ID NO: 7) and primer 2 (SEQ ID NO: 8). Pyrobest DNA polymerase (Takara Shuzo) was used for PCR, which was performed, after (1) denaturation at 98° C. for 10 seconds, by (2) repeating 35 times the cycle set to include 98° C. for 10 seconds and 68° C. for 60 seconds, followed by (3) extension at 68° C. for 7 minutes. The amplified product was inserted into pCR-Blunt2-TOPO vector (Invitrogen), which was then introduced into *Escherichia coli* JM109 (Takara Shuzo) for cloning. As a result of analysis of the base sequence, the base sequence (SEQ ID NO: 4) of cDNA encoding rat GPR52 having the amino acid sequence represented by SEQ ID NO: 3 was obtained.

Example 2

Cloning of Mouse GPR52

Using mouse (C57BL/6) brain cDNA (BD Biosciences) as a template, PCR was performed using primer 1 (SEQ ID NO: 7) and primer 2 (SEQ ID NO: 8). Pyrobest DNA polymerase (Takara Shuzo) was used for PCR, which was performed, after (1) denaturation at 98° C. for 10 seconds, by (2) repeating 35 times the cycle set to include 98° C. for 10 seconds and 68° C. for 60 seconds, followed by (3) extension at 68° C. for 7 minutes. The amplified product was inserted into pCR-Blunt2-TOPO vector (Invitrogen), which was then introduced into *Escherichia coli* JM109 (Takara Shuzo) for cloning. As a result of analysis of the base sequence, the base sequence (SEQ ID NO: 6) of cDNA encoding mouse GPR52 having the amino acid sequence represented by SEQ ID NO: 5 was obtained.

Example 3

Search for Ligand of GPR52

The stable expression cell line (CNGC-E583M/HEK293 cell line) of rat olfactory cyclic nucleotide-gated channel (CNGC-E583M), which was used as a host cell, was obtained by inserting rat olfactory cyclic nucleotide-gated channel (CNGC-E583M) cDNA into expression vector pcDNA3.1(+) neo (Invitrogen) (pcDNA3.1-CNGC), transfecting pcDNA3.1-CNGC into HEK293 cells (purchased from ATCC) in a conventional manner, and incubating the cells in DMEM (Dulbecco's modified Eagle medium) supplemented with 10% fetal calf serum (Invitrogen) and 800 mg/l geneticin (Invitrogen) under 5% $CO_2$ at 37° C. [Fagan et al., FEBS, 500, 85 (2001); Reinescheid et al., European Journal of Pharmacology, 478, 27 (2003)]. The CNGC-E583M/HEK293 cells were incubated in a collagen-coated 75 $cm^2$ flask. When the cells reached about 70% confluent, the human GPR52 expression plasmid prepared in REFERENCE EXAMPLE 1 was transfected. The transfection was performed using Lipofectamine reagent (Invitrogen) according to a modification of the protocol attached to the reagent. First, two 15 ml centrifuge tubes were prepared and 600 μl of Opti-MEM (Invitrogen) was dispensed into each tube. Next, after 2.4 μg of the pAKKO-GPR52 expression vector (REFERENCE EXAMPLE 1) was charged in one tube and 36 μl of the Lipofectamine reagent was charged in the other tube, both were mixed with each other and the mixture was settled for 20 minutes at room temperature. A mixture for transfection prepared by adding 6 ml of Opti-MEM to the resulting solution was added to CNGC-E583M/HEK293 cells, which had been previously washed in Opti-MEM, was incubated in a $CO_2$ incubator (5% $CO_2$, 37° C.) for 5 hours. Thereafter, the mixture for transfection was removed and 10% fetal calf serum-containing DMEM was exchanged in place of the mixture. After rinsing with PBS (Invitrogen) on the following day, the cells were detached with 0.05% trypsin/EDTA solution (Invitrogen), recovered by centrifugal operation and diluted in $4 \times 10^4$ cells/100 μl. Then, the dilution was dispensed in a poly-D-lysine black walled 96-well plate (Becton Dickenson) in 100 μl each/well, followed by incubation overnight in a $CO_2$ incubator (hereinafter referred to as the cell plate). Various test compounds were added to the CNGC-E583M/HEK293 cells in which the receptor was transiently expressed by the transfection procedure described above, whereby changes in intracellular calcium levels were assayed on FLIPR (Molecular Device). To assay for the changes in intracellular calcium levels on FLIPR, the following pretreatment was performed. First, an assay buffer was prepared to add fluorescence dye Fluo-3AM (DOJIN) to the cells or to wash the cells immediately before the FLIPR assay. To 1000 ml of HBSS (Invitrogen) supplemented with 20 ml of 1M HEPES (pH7.4) (DOJIN) (hereinafter HBSS/HEPES solution), 10 ml of a solution prepared by dissolving 710 mg of Probenecid (Sigma) in 5 ml of 1N NaOH and further adding 5 ml of the HBSS/HEPES solution was added. The resulting solution was used as the assay buffer. Next, 50 μg of Fluo-3AM was dissolved in 21 μl of DMSO (DOJIN) and an equal volume of 20% Pluronic acid (Molecular Device) was further added to and mixed with the solution. The mixture was then added to 10.6 ml of the assay buffer supplemented with 105 μl of fetal calf serum, and 20 μl of 500 mM IBMX/DMSO was further added to prepare a fluorescence dye solution. The fluorescence dye solution was dispensed onto the cell plate by 100 μl each/well using an 8-channel pipette and the cells were incubated at 37° C. in a 5% $CO_2$ incubator for an hour (dye loading).

The solution containing a test compound was added to 220 μl of H/HBSS containing 0.5 mM IBMX and 2.5 mM Probenecid for dilution. The dilution was transferred to a 96-well plate for FLIPR (V-Bottom Plate, Costar) (hereinafter referred to as the sample plate). After completion of the dye loading onto the cell plate, the cell plate was washed with a wash buffer composed of H/HBSS supplemented with 2.5 mM Probenecid, using a plate washer (ELX405, Bio-Tek Instruments). After washing, 100 μl of the wash buffer was saved for further procedures. This cell plate and the sample plate were set on FLIPR (by FLIPR, 50 μl of the sample was transferred from the sample plate to the cell plate) to assay changes in fluorescence intensities thereby to determine the activity of increasing intracellular calcium ion levels.

Figure 2:
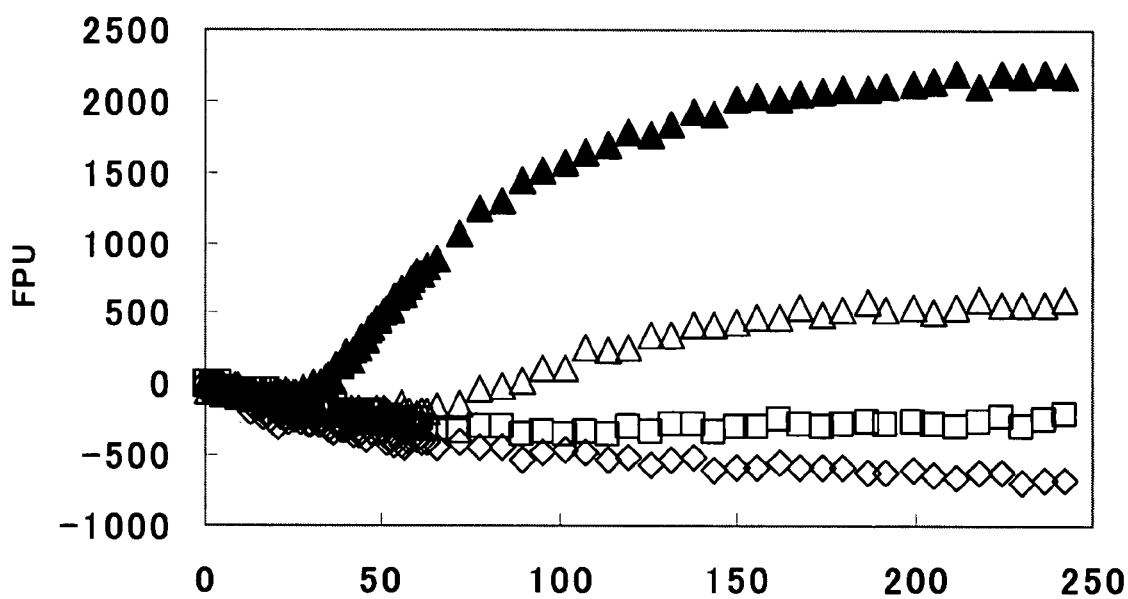
FIG. 2 shows the results obtained by monitoring changes in intracellular $Ca^{2+}$ levels when human GPR52 expression plasmid is transiently expressed in the CNGC-E583M/HEK293 cell line and methoctramine is added. In the figure, the ordinate denotes fluorescence intensities showing the intracellular $Ca^{2+}$ levels and the abscissa denotes passage of time (second) after starting the measurements, in which ◇ (open diamond) represents HBSS buffer (Base), □ (open square) represents 15 µM methoctramine, Δ (open triangle) represents 45 µM methoctramine and ▲ (closed triangle) represents 75 µM methoctramine.

The results reveal that the intracellular calcium ion levels were increased dose-dependently by adding reserpine (FIG. 1) and methoctramine (FIG. 2).

In the other receptor expression vector-transfected CNGC-E583M/HEK293 for control, such a response was not observed.

Example 4

Increase of Intracellular cAMP Levels in Human GPR52 Expression CHO Cell Line

The human GPR52 expression CHO cells obtained in REFERENCE EXAMPLE 1 was washed in the assay medium (HBSS (Gibco BRL) supplemented with 0.2 mM isobutylmethylxanthine), followed by incubation for 30 minutes under conditions at 37° C. in 5% $CO_2$. Then, reserpine diluted in the assay medium was added in various concentrations. The assay buffer alone was used as a Base. After the addition, incubation was conducted for 30 minutes under conditions at 37° C. in 5% $CO_2$. The culture supernatant was discarded and the intracellular cAMP level was assayed on the plate reader (EnVision, Perkin-Elmer) in accordance with the protocol of cAMP Screen Kit (Applied Biosystems). As negative controls, the CHO cell line (Mock) wherein no exogenous receptor was expressed and the CHO cell line (TGR5) wherein Gs-conjugated receptor TGR5 was stably expressed were co-assayed.

Figure 3:
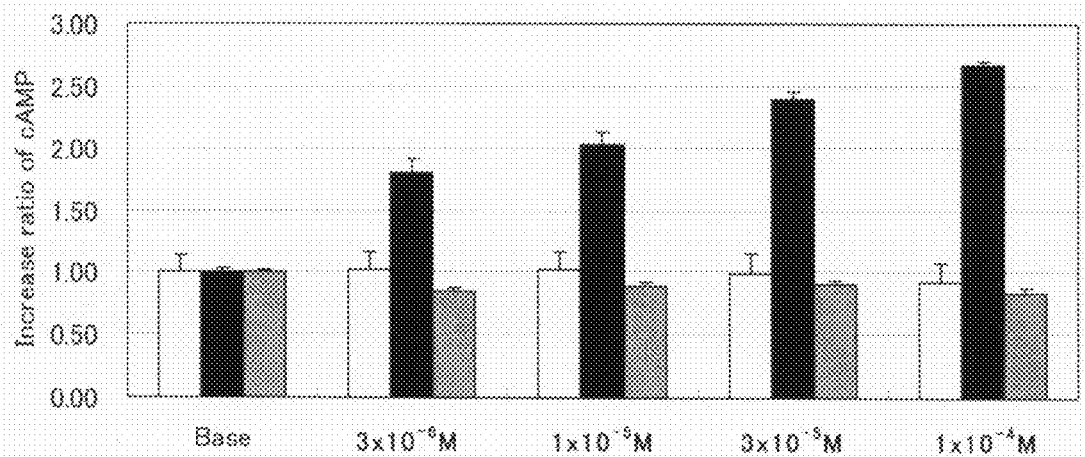
FIG. 3 shows the results obtained by monitoring intracellular cAMP levels in CHO cells wherein human GPR52 is stably expressed, which levels are increased by reserpine stimulation. In the figure, the ordinate denotes the increase ratio of cAMP and the abscissa denotes amounts of reserpine added, in which white bar shows the results with Mock CHO cell line, black bar shows the results with GPR52-expressed CHO cell line and hatched bar shows the results with TGR5-expressed cell line.

As a result, the increased intracellular cAMP levels caused by the addition of reserpine were detected dose-dependently only in the human GPR52 expression CHO cell line (FIG. 3).

Example 5

Internalization of GPR52-GFP Fusion Protein Expressed in CHO Cells by Addition of Reserpine An expression plasmid was constructed to express a fused protein of Green Fluorescent Protein (GFP) cDNA isolated from jellyfish or *Auquorea victoria*, fused to GPR52 at the C-terminus to fit the translation frame. In this case, a fragment excised from GFP expression vector pQBI25 (Takara Shuzo) was used as GFP cDNA. In GPR52, its termination codon was modified by PCR to recognition sequence with restriction enzyme NheI, and the GFP fragment was ligated thereto, which was inserted into the expression vector pAKKO-111H [Biochem. Biophys. Acta, 1219, 251 (1994)] and transfected to CHO cells in a conventional manner to obtain the human GPR52-GFP expression CHO cell line. The human GPR52-GFP expression CHO cells were suspended in a growth medium [αMEM (containing nucleic acids: Invitrogen) supplemented with 10% fetal calf serum (GIBCO BRL)] and plated on a Lab-TekII cover glass chamber with 4 chambers (Nalgen Nunc) in a concentration of $0.6 \times 10^5$ cells/chamber. After incubation overnight at 37° C. in 5% $CO_2$, the medium was replaced by a medium for confocal microscopic observation [Hanks' Balanced Salt Solution (GIBCO BRL)] and the fluorescent images of GFP were observed with a confocal microscope (Leica). In this case, GFP was excited at 488 nm.

As a result, the GPR52-GFP fused protein was observed on the cell membrane. When reserpine was added to the medium in $10^{-4}$ M, it was found that the fluorescence of GFP was not observed on the cell membrane but moved to the cytoplasm 30 minutes after. This indicates that GPR52 was a G protein-coupled type receptor expressed on the cell membrane and at the same time, GPR52 was reacted with reserpine to move to the cytoplasm, namely, internalization occurred.

Example 6

Analysis on Tissue Distribution of Human GPR52, Mouse GPR52 and Rat GPR52 mRNA (1) For cDNAs to be used as templates for analysis of gene expression distribution in human, the products synthesized by the following procedures using polyA+RNA (Clontech) derived from various tissues of human were used.

Following the manual attached, the reaction was carried out at 42° C. using a random primer from 1 μg of RNA and SuperScriptII reverse transcriptase (Invitrogen) as a reverse transcriptase. After completion of the reaction, the mixture was precipitated with ethanol and the precipitate was dissolved in 100 μl. RT-PCR was carried out using Sequence Detection System Prism 7700 (Applied Biosystems), and primer 1 (SEQ ID NO: 9), primer 2 (SEQ ID NO: 10) and probe 1 (SEQ ID NO: 11) were employed. The RT-PCR solution was prepared by adding to 12.5 μl of TaqMan Universal PCR Master Mix (Applied Biosystems) 0.05 μl each of 100 μM primer solutions, 0.5 μl of 5 μM probe 1 and 0.5 μl of the cDNA solution prepared above. Distilled water was added to the reaction solution to make the total volume 25 μl. PCR was carried out, after maintaining at 50° C. for 2 minutes and 95° C. for 10 minutes, by repeating 40 times one cycle to set to include 95° C. for 15 seconds and 60° C. for 1 minute.

As a result, human GPR52 was abundantly expressed in the putamen and caudate nucleus.

(2) For cDNAs to be used as templates for analysis of expression in mice, the products synthesized from total RNAs derived from various tissues of mice by the following procedures were used.

Following the manual attached, the reaction was carried out at 42° C. using a random primer from 1 μg of RNA and SuperScriptII reverse transcriptase (Invitrogen) as a reverse transcriptase. After completion of the reaction, the mixture was precipitated with ethanol and the precipitate was dissolved in 100 μl. RT-PCR was carried out using Sequence Detection System Prism 7700 (Applied Biosystems), and primer 3 (SEQ ID NO: 12), primer 4 (SEQ ID NO: 13) and probe 2 (SEQ ID NO: 14) were employed. The RT-PCR solution was prepared by adding to 12.5 μl of TaqMan Universal PCR Master Mix (PE Biosystems) 0.05 μl each of 100 μM primer solutions, 0.5 μl of 5 μM probe 2 and 0.5 μl of the cDNA solution prepared above. Distilled water was added to the reaction solution to make the total volume 25 μl. PCR was carried out, after maintaining at 50° C. for 2 minutes and 95° C. for 10 minutes, by repeating 40 times one cycle to set to include 95° C. for 15 seconds and 60° C. for 1 minute.

As a result, mouse GPR52 mRNA was abundantly expressed specifically in the striatum and female pituitary gland.

(3) Various organs were isolated from Wistar rats and total RNA was collected by Isogen (Nippon Gene). From the total RNA obtained, poly(A)+RNA was prepared using an mRNA Purification Kit (Pharmacia). All were prepared following the manuals, respectively. After 1 µg of poly(A)+RNA was treated with Dnase I (Amplification Grade, GIBCO BRL), cDNA was synthesized from 160 ng of the product at 42° C. in accordance with the manual attached, using an RNA PCR Kit (Takara). A solution of 4 ng/µl when calculated as poly (A)+RNA was prepared from the cDNA synthesized and the solution was used as a template for subsequent RT-PCR. RT-PCR was performed using Sequence Detection System Prism 7700 (Applied Biosystems), and primer 5 (SEQ ID NO: 15), primer 6 (SEQ ID NO: 16) and probe 3 (SEQ ID NO: 17) were employed. The RT-PCR solution was prepared by adding to 12.5 µl of TaqMan Universal PCR Master Mix (PE Biosystems) 0.05 µl each of 100 µM primer solutions, 0.5 µl of 5 µM probe 3 and 0.5 µl of the cDNA solution prepared above. Distilled water was added to the reaction solution to make the total volume 25 µl. PCR was carried out, after maintaining at 50° C. for 2 minutes and 95° C. for 10 minutes, by repeating 40 times one cycle to set to include 95° C. for 15 seconds and 60° C. for 1 minute. The mRNA expression levels of GPR52 obtained in various rat tissues were calculated in terms of the copy number per 1 ng of poly(A)+RNA.

As a result, rat GPR52 was abundantly expressed in the striatum, pituitary gland and female pituitary gland.

Example 7

Analysis of Expression Distribution of GPR52 mRNA in Brain and Pituitary Gland by In Situ Hybridization Digoxigenin-labeled GPR52 probe was prepared by the following procedures. First, rat GPR52 cDNA was inserted into plasmid vector pCR-Blunt II-TOPO (Invitrogen) by publicly known methods. This cDNA was amplified and linearized by PCR using M13 primer (Invitrogen) and Advantage cDNA PCR-Kit (Clontech). The product was purified by ethanol precipitation. The cDNAs obtained were subjected to in vitro transcription with SP6 or T7 (40 µl scale) using a DIG RNA Labeling KIT (SP6/T7) (Roche). After ethanol precipitation the transcript was hydrolyzed to 400 bp under conditions of 40 mM $NaHCO_3$, 60 mM $Na_2CO_3$, pH 10.2 and 60° C. Following further ethanol precipitation, the products were dissolved in 100 µl of distilled water to give digoxigenin-labeled rat GPR52cRNA probes (antisense probe and sense probe).

Male mature SD rats (Charles River Japan) were sacrificed and the brain was taken out. After rinsing with PBS, the brain was embedded in OCT compound and frozen in liquid nitrogen, which was stored at −80° C. In addition, female mature SD rats were sacrificed and the pituitary gland was taken out. After rinsing with PBS, the pituitary gland was embedded in OCT compound and frozen in liquid nitrogen, which was stored at −80° C. The brain and pituitary gland tissues were sliced in a thickness of 16 µm on a MAS-coated slide (Matsunami Glass) using Cryostat CM3050 (Leica). The slice was fixed in 4% paraformaldehyde-containing ¹⁄₁₅M phosphate buffer, pH 7.4 (Wako Pure Chemicals) at room temperature for 10 minutes. After washing 3 times with PBS, the slide was immersed in 0.25% acetic anhydride-containing 0.1M triethanolamine at room temperature for 10 minutes. After washing the slide 3 times with PBS, the digoxigenin-labeled rat GPR52cRNA probes were diluted to 200-fold in a hybridization buffer (50% formamide, 10 mM Tris-HCl pH 7.5, 1× Denhardt's solution, 200 µg/ml tRNA, 10% dextran sulfate, 600 mM NaCl, 0.25% SDS, 1 mM EDTA pH 8.0) and 60 µl of the dilution was dropwise added onto the slice on the slide (covered with parafilm), followed by hybridization overnight at 60° C. in a moisture chamber with 50% formamide. Subsequently, the following procedures were performed to wash off the probes non-specifically hybridized from the slice on the slide. 1) A treatment with 2×SSC (SSC; 1×SSC=150 mM NaCl, 15 mM sodium citrate, pH 7.0)/50% formamide (60° C. for 30 minutes, once), 2) a treatment with 2×SSC (60° C. for 20 minutes, once) and 3) a treatment with 0.1×SSC (60° C. for 20 minutes, twice). Following these procedures, immunohistochemistry was applied to detect the digoxigenin-labeled probes. First, after washing the slide with wash buffer (100 mM Tris-HCl pH 7.5, 150 mM NaCl, 0.1% Tween 20), non-specific reactions were blocked by a treatment (room temperature for an hour) with the wash buffer containing 1.5% Blocking Reagent (Roche), and anti-DIG fab-fragment antibody conjugated with alkaline phosphatase (Roche), which was diluted in the wash buffer to 1000-fold, was reacted at room temperature for an hour. After washing the slide 3 times with the wash buffer at room temperature for 15 minutes, the tissue was rinsed with a color development buffer (100 mM Tris-HCl pH 9.5, 100 mM NaCl, 50 mM $MgCl_2$), followed by color development reaction overnight at room temperature in a color development solution (color development buffer containing 50 mg/ml BCIP (Roche), 100 mg/ml NBT (Roche), 3% polyvinyl alcohol). After the color formation was appropriately terminated by washing with PBS, the tissue was permanently sealed with Pristine Mount (Falma) and observed/photographed. As a result, signals specific to the antisense probe were observed in wide areas in the rat brain to show the expression of GPR52 mRNA. In the basal ganglion, GPR52 mRNA was very abundantly expressed in the striatum, nucleus accumbens and olfactory tubercle. GPR52 mRNA was widely expressed in the cerebral cortex, focusing on the frontal lobe and temporal lobe. In the amygdale, GPR52 mRNA was expressed in the basolateral nucleus, lateral nucleus, medial nucleus, etc. In the hippocampus, GPR52 mRNA was expressed in the Ammon's horn, dentate gyrus, subiculum. In the thalamus, GPR52 mRNA was very strongly expressed in the medial habenular nucleus and also expressed in the thalamic reticular nucleus, paraventricular thalamic nucleus, nigrostriatal bundle, etc. In the hypothalamus, GPR52 mRNA was expressed somewhat strongly in the medial mammillary nucleus and further expressed in the arcuate nucleus, lateral hypothalamus, etc. In the midbrain, GPR52 mRNA was expressed somewhat strongly in the dorsolateral/ventrolateral geniculate nucleus and also expressed in the ventral tegmental area, midbrain aqueductal grey matter, etc. In the pituitary gland, GPR52 mRNA was expressed in the anterior lobe, and its expression levels in the intermediate lobe and posterior lobe were below the detection limit (TABLE 1).

These results suggest that GPR52 would be widely involved in various functions of the brain.

TABLE 1

| Tissue | Rat GPR52 mRNA |
| --- | --- |
| frontal association area | ++ |
| prelimbic cortex | ++ |
| infralimbic cortex | ++ |
| dorsal cortex | ++ |
| medial orbital cortex | ++ |
| orbital cortex | ++ |
| piriform cortex | ++ |
| anterior olfactory nucleus | ++ |
| dorsal septal nucleus | ++ |
| ventral pallidum | + |
| striatum | +++ |
| nucleus accumbens | +++ |
| olfactory tubercle | +++ |

TABLE 1-continued

| Tissue | Rat GPR52 mRNA |
| --- | --- |
| interstitial nucleus | ++ |
| bed nucleus of stria terminalis | ++ |
| cingulate cortex | ++ |
| motor cortex | + |
| sensory cortex | + |
| granular insular cortex | + |
| perirhinal cortex | + |
| ectorhinal cortex | ++ |
| entorhinal cortex | ++ |
| visual cortex | + |
| auditory cortex | + |
| lateral amygdaloid nucleus | + |
| basolateral amygdaloid nucleus | + |
| medial amygdaloid nucleus | + |
| basomedial amygdaloid nucleus | + |
| amygdalopiriform transition area | + |
| cortical amygdaloid nucleus | + |
| amygdalohippocampal area | + |
| granular layer of dentate gyrus | + |
| pyramidal layer of hippocampus CA1-CA3 | + |
| subiculum | + |
| paratenial nucleus | ++ |
| lateral habenular nucleus | ++ |
| medial habenular nucleus | +++ |
| paraventricular thalamic nucleus | ++ |
| centromedian thalamic nucleus | + |
| centromedian thalamic nucleus | + |
| rhomboid thalamic nucleus | + |
| reuniens thalamic nucleus | ++ |
| posterior hypothalamic region | + |
| thalamic reticular nucleus | + |
| posterior commissural nucleus | + |
| globus pallidus medial segment | ++ |
| anterior hypothalamus | + |
| lateral hypothalamus | ++ |
| hypothalamic arcuate nucleus/medial posterior | + |
| mammillary nucleus | + |
| medial mammillary nucleus | ++ |
| substantia nigra pars compacta | + |
| substantia nigra pars reticulata | + |
| tegmental nucleus | + |
| midbrain periaqueductal grey matter | + |
| interpeduncular nucleus | + |
| medial vestibular nucleus, parvocellular part | ++ |
| anterior nucleus of hypoglossal nerve | + |

Example 8

Comparison in Localization of GPR52 mRNA and Dopamine D1 Receptor mRNA or Dopamine D2 Receptor mRNA in Brain Using Double In Situ Hybridization For codetection of GPR52 mRNA and the dopamine D1 receptor mRNA or the dopamine D2 receptor mRNA, double in situ hybridization was performed using the digoxigenin-labeled GPR52cRNA probe and the fluorescein-labeled dopamine D1 receptor cRNA probe or the fluorescein-labeled dopamine D2 receptor cRNA probe.

The digoxigenin-labeled GPR52cRNA probe was prepared in a manner similar to EXAMPLE 7.

The fluorescein-labeled dopamine D1 receptor cRNA probe and the fluorescein-labeled dopamine D2 receptor cRNA probe were prepared by the following procedures. First, the dopamine D1 receptor and D2 receptor cDNAs were cloned from the striatum of male Wistar rats by publicly known methods. These cDNAs were inserted into plasmid vector pCRII-TOPO (Invitrogen) by publicly known methods. These cDNAs were amplified and linearized by PCR using M13 primer (Invitrogen)/Advantage cDNA PCR-Kit (Clontech), and the products were purified by ethanol precipitation. The cDNAs obtained were subjected to in vitro transcription with SP6 or T7 (40 μl scale) using a DIG RNA Labeling KIT (SP6/T7) (Roche). Fluorescein RNA Labeling Mix (Roche) was used for labeling. After ethanol precipitation, the products were dissolved in 100 μl of distilled water to give the fluorescein-labeled dopamine D1 receptor cRNA probes (antisense probe and sense probe) and the fluorescein-labeled dopamine D2 receptor cRNA probes (antisense probe and sense probe).

Male mature SD rats (Charles River Japan) were sacrificed and the brain was taken out. After rinsing with PBS, the brain was embedded in OCT compound and frozen in liquid nitrogen, which was stored at −80° C. The brain was sliced in a thickness of 16 μm on a MAS-coated slide (Matsunami Glass) using Cryostat CM3050 (Leica). The slice was fixed in 4% paraformaldehyde-containing 1/15M phosphate buffer, pH 7.4 (Wako Pure Chemicals) at room temperature for 10 minutes. After washing the slide 3 times with PBS, the slide was immersed in 0.25% acetic anhydride-containing 0.1M triethanolamine (TEA) at room temperature for 10 minutes. After washing the slide 3 times with PBS, the digoxigenin-labeled GPR52cRNA probes and fluorescein-labeled dopamine D1 receptor cRNA probes were diluted to 200-fold and 500-fold, respectively, in a hybridization buffer, or the digoxigenin-labeled GPR52cRNA probes and fluorescein-labeled dopamine D2 receptor cRNA probes were diluted to 200-fold and 500-fold, respectively, in a hybridization buffer, and total 60 μl of the dilutions was dropwise added to the slide (covered with parafilm), followed by hybridization overnight at 60° C. in a moisture chamber with 50% formamide. Subsequently, the following procedures were performed to wash off the probes non-specifically hybridized. 1) A treatment with 2×SSC(SSC; 1×SSC=150 mM NaCl, 15 mM sodium citrate, pH 7.0)/50% formamide (60° C. for 30 minutes, once), 2) a treatment with 2×SSC (60° C. for 20 minutes, once) and 3) a treatment with 0.1×SSC (60° C. for 20 minutes, twice). Following these procedures, tyramide signal amplification using GenPoint™ Fluorescein (DAKO) was applied to detect the fluorescein-labeled probes. After HRP labeling of the fluorescein-labeled probes was performed according to the manual of GenPoint™ Fluorescein (DAKO), a color (brown color) was developed by a DAB substrate-chromogen solution. After the color formation was appropriately terminated by immersing in DW for 1 minute, immunohistochemistry was subsequently applied to detect the digoxigenin-labeled GPR52cRNA probes. First, after the slide was washed with a wash buffer (100 mM Tris-HCl pH 7.5, 150 mM NaCl, 0.1% Tween 20), the slide was treated with the wash buffer containing 1.5% Blocking Reagent (Roche) (room temperature for an hour) to block non-specific reactions. Next, the anti-DIG fab-fragment antibody conjugated with alkaline phosphatase (Roche), which was diluted in the wash buffer to 1000-fold, was reacted at room temperature for an hour. After washing the slide 3 times with the wash buffer at room temperature for 15 minutes, the tissue was rinsed with a color development buffer (100 mM Tris-HCl pH 9.5, 100 mM NaCl, 50 mM MgCl$_2$), followed by color (blue color) development reaction overnight at room temperature in a color development solution (color development buffer containing 50 mg/ml BCIP (Roche), 100 mg/ml NBT (Roche), 3% polyvinyl alcohol). After the color formation was appropriately terminated by washing with PBS, the tissue was permanently sealed with Pristine Mount (Falma) and observed/photographed.

As a result, GPR52 mRNA was expressed in neurons different from the dopamine D1 receptor in the rat striatum, nucleus accumbens and olfactory tubercle. On the other hand, GPR52 mRNA was expressed in the same neurons as in the dopamine D2 receptor mRNA. These results reveal that GPR52 specifically coexists with the D2 receptor in the rat striatum, nucleus accumbens and olfactory tubercle. In the rat cerebral cortex, GPR52 mRNA was expressed in the medial prefrontal cortex (hereinafter referred to as mPFC) in the frontal lobe as the dopamine D1 receptor mRNA and D2 receptor mRNA were. In mPFC, GPR52 was also co-expressed with neurons expressing the dopamine D1 receptor or D2 receptor. In mPFC, the dopamine D1 receptor was expressed more widely than the dopamine D2 receptor mRNA. GPR52 mRNA was likewise expressed widely in mPFC. Therefore, coexistence with neurons expressing the dopamine D1 receptor mRNA was observed much more frequently. Also in the cingulate cortex, GPR52 mRNA was co-expressed with neurons expressing the dopamine D1 or D2 receptor mRNA. In the piriform cortex or olfactory nucleus, GPR52 mRNA and dopamine D1 receptor mRNA were expressed clearly in the same cells, whereas the dopamine D2 receptor was not expressed or weakly expressed in the cells expressing GPR52 mRNA.

The foregoing results suggested that GPR52 could be a target molecule for abnormalities in the dopaminergic mesencephalostriatal pathways (e.g., Parkinson's disease), abnormalities in the mesolimbic pathways (e.g., positive schizophrenia symptoms), abnormalities in the mesocortical pathways (e.g., negative schizophrenia symptoms), etc.

Example 9

Activation of NMDA-Type Glutamate Receptor in Cerebral Cortex by Methoctramine

Neurons from rat embryonic cerebral cortex (CAMBREX) were cultured in a 48-well poly-L-lysine (Sumitomo Bakelite) for 14-15 days by a modification of the method attached. A neuron culture medium (Dainippon Pharmaceutical) was used as a medium, unless otherwise indicated. Changes in intracellular calcium levels were assayed using AQUACOSMOS (Hamamatsu Photonics). For assaying the changes in intracellular calcium levels, the following pretreatment was made. First, in order to add fluorescence dye fura-2/AM (Molecular Probes) to cells, an assay buffer used to wash the cells immediately before the assay was prepared. To 1000 ml of HBSS (Invitrogen) supplemented with 20 ml of 1M HEPES (pH7.4) (DOJIN) (hereinafter HBSS/HEPES solution), 10 ml of a solution prepared by dissolving 710 mg of Probenecid (Sigma) in 5 ml of 1N NaOH and further adding 5 ml of the HBSS/HEPES solution thereto was added, and the resulting solution was used as the assay buffer. Next, an equal volume of 20% Pluronic acid (Molecular Device) was added to and mixed with the fura-2/AM stock solution. The mixture was dissolved in the assay buffer in a final concentration of 5 μM fura-2 to prepare the fura-2 fluorescence dye solution. The fura-2 fluorescence dye solution was loaded on neurons from the rat embryonic cerebral cortex, followed by incubation for 30-60 minutes. Thereafter, the changes in calcium levels in the individual neurons were determined using AQUACOSMOS (Hamamatsu Photonics).

Figure 4:
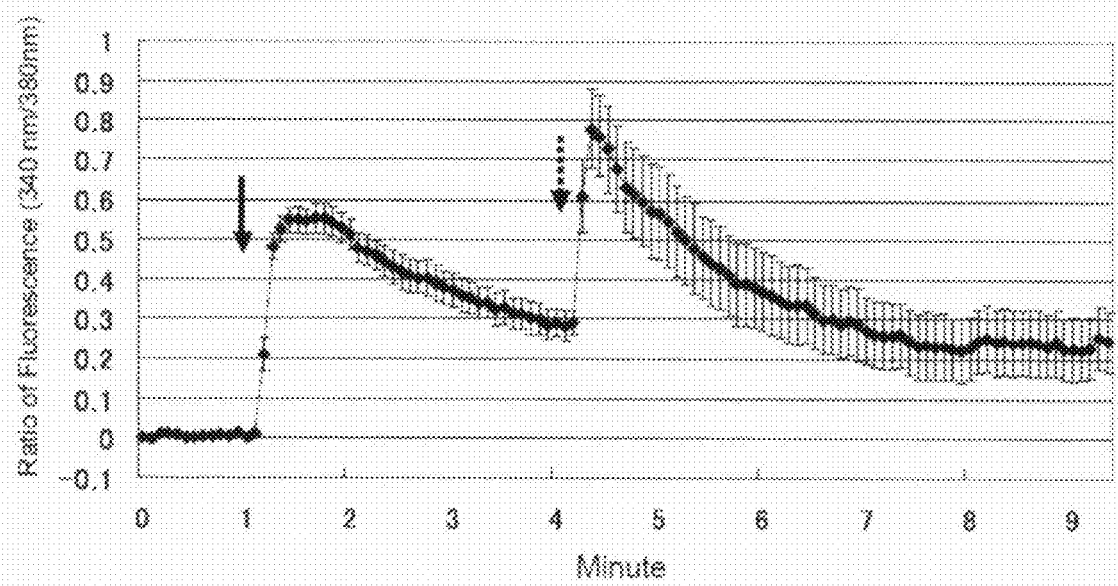
FIG. 4 shows the measurement results of increase in calcium levels. In the figure, the ordinate denotes fluorescence intensities showing the intracellular $Ca^{2+}$ levels and the abscissa denotes passage of time (minute) after starting the measurements. At the point of time shown by black arrow, 10 µM glutamate was added and 0.2 mM methoctramine was added at the point of time shown by dashed arrow.
Figure 5:
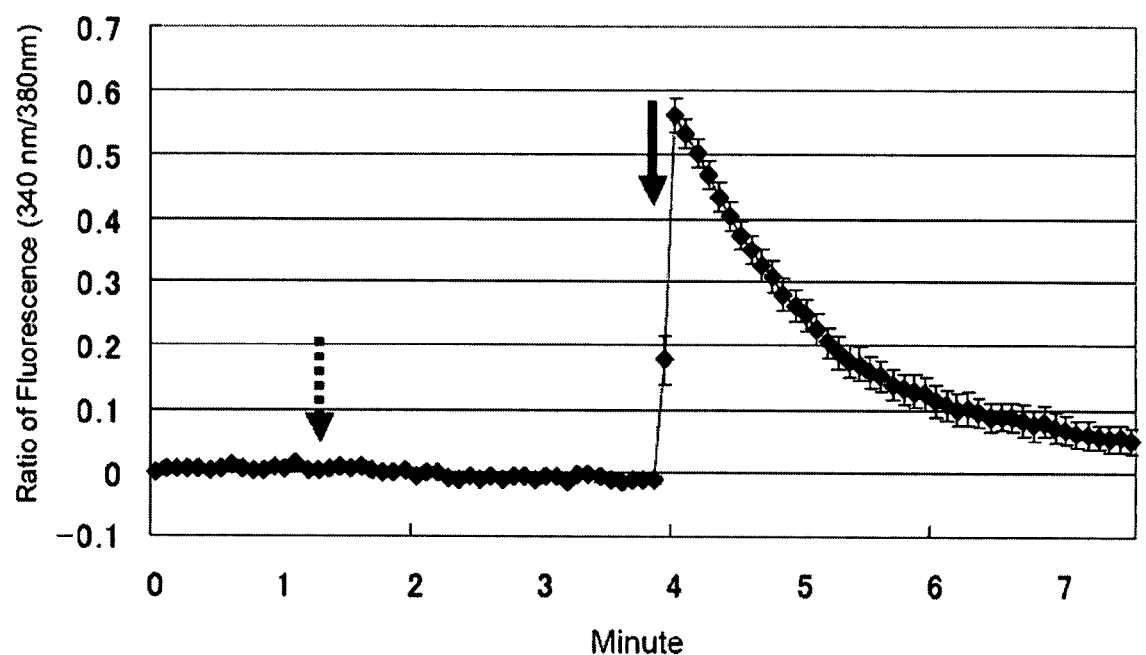
FIG. 5 shows the measurement results of increase in calcium levels. In the figure, the ordinate denotes fluorescence intensities showing the intracellular $Ca^{2+}$ levels and the abscissa denotes passage of time (minute) after starting the measurements. At the point of time shown by dashed arrow, 0.2 mM methoctramine was added and 5 μM glutamate was added at the point of time shown by black arrow.

The results reveal that an increase in the intracellular calcium levels showing activation of the NMDA-type glutamate receptor by glutamate was observed and subsequent diminution of the increased calcium levels occurred, during which methoctramine was added so that the NMDA-type glutamate receptor was reactivated to induce the calcium level increase (FIG. 4). The calcium level increase was shown in terms of the ratio of Fura-2 fluorescence (340 nm/380 μm) for the individual neurons (n=11) (FIG. 4). To the contrary, when glutamate was not added but methoctramine alone was added, any increase in calcium levels was not observed (FIG. 5). The calcium level increase was shown in terms of the ratio of Fura-2 fluorescence (340 nm/380 nm) for the individual neuron (n=27) (FIG. 5).

The results revealed that methoctramine having the ligand activity for GPR52 acts as a potentiator having the activity to potentiate activation of the NMDA-type glutamate receptor. The NMDA-type glutamate receptor is strongly associated with schizophrenia; since it became clear that negative schizophrenia symptoms or cognitive impairment is improved by potentiating activation of this receptor, it is expected that potentiation of the NMDA-type glutamate activity by these GPR52 agonists results in improving these symptoms (Science, 296, 692, 2002, etc.).

Example 10

Screening of GPR52 Agonists (1)

Using the CNGC-E583M/HEK293 cell line described in EXAMPLE 3, screening of agonists was performed as follows. The CNGC-E583M/HEK293 cells were incubated in a collagen-coated 75 cm$^2$ flask. When the cells reached about 70% confluent, the human GPR52 expression plasmid prepared in REFERENCE EXAMPLE 1 was transfected. The transfection was performed using Lipofectamine reagent (Invitrogen) according to a modification of the protocol attached to the reagent. First, two 15 ml centrifuge tubes were prepared and 600 μl of Opti-MEM (Invitrogen) was dispensed into each tube. Next, after 2.4 μg of the pAKKO-GPR52 expression vector (REFERENCE EXAMPLE 1) was charged in one tube and 36 μl of the Lipofectamine reagent was charged in the other, both were mixed with each other and the mixture was settled for 20 minutes at room temperature. A mixture for transfection prepared by adding 6 ml of Opti-MEM to the resulting solution was added to CNGC-E583M/HEK293 cells, which had been previously rinsed once in Opti-MEM, was incubated in a $CO_2$ incubator (5% $CO_2$, 37° C.) for 5 hours. Thereafter, the mixture for transfection was removed and 10% fetal calf serum-containing DMEM was exchanged in place of the mixture. On the following day, the cells were detached with 0.05% trypsin/EDTA solution (Invitrogen), recovered by centrifugal operation and diluted in $4 \times 10^5$ cells/μl. Then, the dilution was dispensed in a poly-D-lysine black walled 96-well plate (Becton Dickenson) in 100 μl each/well, followed by incubation overnight in a $CO_2$ incubator (hereinafter referred to as the cell plate). Various test compounds were added to the CNGC-E583M/HEK293 cells in which GPR52 was transiently expressed by the transfection procedures described above, whereby the changes in intracellular calcium levels were assayed on FLIPR (Molecular Device) by the procedures described in EXAMPLE 3.

As a result, a plurality of compounds (agonist candidate compounds) received hits as increasing the intracellular calcium levels specifically to the GPR52 expression CNGC-E583M/HEK293 cells.

Example 11

Screening of GPR52 Agonists (2)

The GPR52 stable expression cells prepared in REFERENCE EXAMPLE 1 were incubated in a 150 cm$^2$ at 37° C. overnight in a $CO_2$ incubator. After the incubation, the cells were detached with 0.5 mM EDTA/PBS, and washed in PBS. The cells were then suspended at a density of $1 \times 10^7$ cells/ml in Buffer 1 (HBSS+0.1% BSA, 25 mM HEPES, pH 7.3, 0.5 mM IBMX). This cell suspension, 440 μl, was mixed with 22 μl of Anti-cAMP Acceptor Beads of AlphaScreen cAMP Assay Kit (Perkin Elmer) and 638 μl of Buffer 1. The resulting mixture was dispensed on a white 96-well plate (Costar) by 10 µl each. Next, 10 µl each of the test compound dilutions in Buffer 1 was added to each well. After shaking at room temperature for 30 minutes, 20 µl of Biotinyl cAMP and 82 µl of Streptavidin Donor Beads of AlphaScreen cAMP Assay Kit was added to 40 ml of Buffer 2 (HBSS+0.1% BSA, 25 mM HEPES, pH 7.3, 1.5% Tween 20) and the resulting mixture was added to all wells of the plate by 30 µl each. The plate was kept shaken at room temperature for 3 hours and the fluorescence intensities were measured by Fusion α (Perkin Elmer).

As a result, a plurality of compounds (agonist candidate compounds) received hits as increasing the intracellular cAMP levels specifically to the GPR52 stable expression cells.

Example 12

Screening of GPR52 Agonists (3)

Using the procedures described in EXAMPLE 11, various compounds were first subjected to primary screening in a final concentration of 30 µM and a plurality of compounds (agonist candidate compounds) were found to increase the intracellular cAMP in the GPR52 stable expression cells. Secondary screening was applied to these compounds in various concentrations (100 µM, 30 µM, 10 µM, 3 µM, 1 µM and 0.1 µM) using the procedures described in EXAMPLE 11 (detailed analysis).

As a result, N-[3-(3-chlorophenoxy)phenyl]-2-methyl-8-[3-(1-piperazinyl)propyl]-5,6,7,8-tetrahydropyrido[2,3-d]pyrimidine-5-amine tetrahydrochloride (EXAMPLE 175 in Japanese Laid-Open Patent Publication (TOKKAI) No. 2003-321472) (hereinafter briefly referred to as Compound A) showed a relatively potent activity. $EC_{50}$ of this compound to GPR52 was 2.1 µM.

Example 13

Activation of NMDA-Type Glutamate Receptor in Cerebral Cortex by Compound A

Activation of the NMDA-type glutamate receptor in the cerebral cortex was analyzed by the procedures described in EXAMPLE 9.

The results reveal that an increase in the intracellular calcium levels showing activation of the NMDA-type glutamate receptor by 10 µM glutamate was observed and subsequent diminution of the increased calcium levels occurred, during which 10 µM Compound A was added so that the NMDA-type glutamate receptor was reactivated to induce the calcium level increase. To the contrary, when glutamate was not added but 15 µM Compound A alone was added, any increase in calcium levels was not observed.

The results revealed that Compound A having the ligand activity for GPR52 acts as a potentiator having the activity to potentiate activation of the NMDA-type glutamate receptor. The cerebral cortex plays a crucial role for advanced information processing including cognition, etc. It is thus expected to improve negative schizophrenia symptoms or cognitive impairment by potentiating the activities of the NMDA-type glutamate by these GPR52 agonists.

Example 14

Phosphorylation of NMDA-Type Glutamate Receptor of Primary Culture Cells in Rat Cerebral Cortex by Compound A Using primary culture neurons from the rat hippocampus, phosphorylation of the NMDA-type glutamate receptor by GPR52 agonists was studied. Rat (Wistar, Charles River Japan) embryonic brain (E19) was dissected to isolate the cerebral cortex, and the cells were prepared using Neuron Dispersion Set (Dainippon Pharmaceutical). The cells were plated on a 24-well poly-L-lysine plate ($3\times10^5$ cells/well) and incubated for 2 weeks in Neuro Basal (B27, containing 0.5 mM glutamine, GIBCO) medium. Compound A was added to the above cells at a final concentration of 50 µM, and the cells were recovered 1, 2, 5, 15 and 30 minutes after. After the cells were lysed in Invitrogen's NuPAGE Sample Buffer (containing DTT), western blot analysis was performed using antibody Anti-phospho-NR1 (Ser897) (Upstate).

The results revealed that Compound A induced phosphorylation (Ser897) of the NMDA-type glutamate receptor. It becomes clear that as a molecular mechanism, phosphorylation (Ser897) of the NMDA-type glutamate receptor mediated by increased intracellular cAMP levels is important for the action of potentiating the activities of the NMDA-type glutamate receptor. Therefore, the NMDA-type glutamate receptor-potentiating action by Compound A described in EXAMPLE 13 was considered to be induced by phosphorylation (Ser897) of the NMDA-type glutamate receptor by GPR52-mediated intracellular cAMP level increase. It was biochemically supported that the GPR52 agonists act as potentiators of the NMDA-type glutamate receptor.

INDUSTRIAL APPLICABILITY

The compound or its salts that promote or inhibit the activities of the receptor (e.g., GPR52, etc.) of the present invention, the compound or its salts that promote or inhibit the expression of a gene for the receptor of the present invention, the compound or its salts (e.g., GPR52 agonists, GPR52 antagonists) which are obtainable by the screening method or screening kit of the present invention, and the like are useful as agents for the prevention/treatment of, for example, mental disorders (e.g., schizophrenia, anxiety, cognitive impairment, panic disorder, phobic disorder, drug-induced psychotic disorder, delusional psychosis, neuroleptic-induced dyskinesia, Parkinson's disease, drug-induced Parkinson's syndrome, extrapyramidal syndrome, etc.), prolactin-related disorders [e.g., hyperprolactinemia (e.g., sterility, galactorrhea, amenorrhea, atrophy of ovary and uterus, etc.), pituitary tumor, diencephalon tumor, menstrual disorder, prolactin hypersecretion [e.g., hyperprolactinemia (e.g., sterility, galactorrhea, amenorrhea, atrophy of ovary and uterus, etc.), pituitary tumor, diencephalon tumor, menstrual disorder, prolactin hyposecretion (e.g., hypoovarianism, spermatic underdevelopment, menopausal symptoms, hypothyroidism, etc.), etc.], hypertension, sleeping disorders [e.g., primary insomnia, circadian rhythm disorders (e.g., change in physical conditions caused by three-shift work, time zone change syndrome (jet lag), etc.], and the like.

In addition, the compound or its salts that promote the activities of the receptor of the present invention, the compound or its salts that promote the expression of a gene for the receptor of the present invention, the agonist for the receptor of the present invention, the ligand for the receptor of the present invention and the like increase the intracellular cAMP levels in neurons wherein the receptor (e.g., GPR52, etc.) of the present invention is expressed and thus can prevent overactive mesolimbic dopamine pathway, which is considered as one of the causes for positive schizophrenia symptoms, to improve the positive schizophrenia symptoms. Furthermore, these compounds can improve hypofunction of the NMDA-type receptor in the cerebral cortex considered as one of the causes for negative schizophrenia symptoms or cognitive impairment to improve the negative schizophrenia symptoms or cognitive impairment. Accordingly, the aforesaid compounds or their salts, agonists, ligands and the like are useful preferably as agents for the prevention/treatment of schizophrenia, cognitive impairment, etc.

Moreover, the compound or its salts that promote the activities of the receptor of the present invention, the compound or its salts that promote the expression of a gene for the receptor of the present invention, the agonist for the receptor of the present invention, the ligand for the receptor of the present invention and the like can promote prolactin release and are thus useful as agents for the prevention/treatment of, prolactin hyposecretion (e.g., hypoovarianism, spermatic underdevelopment, menopausal symptoms, hypothyroidism, etc.), and so on.

The compound or its salts that inhibit the activities of the receptor of the present invention, the compound or its salts that inhibit the expression of a gene for the receptor of the present invention, the antagonist against the receptor of the present invention, and the like can decrease the intracellular cAMP levels in neurons wherein the receptor (e.g., GPR52, etc.) of the present invention is expressed, and can thus improve failure in suppression of intracellular cAMP production induced by dopamine deficiency in the nigrostriatal dopamine pathway, which is considered as one of the causes for Parkinson's disease. Preferably, these compounds are useful as agents for the prevention/treatment of Parkinson's disease, etc.

In addition, the compound or its salts that inhibit the activities of the receptor of the present invention, the compound or its salts that inhibit the expression of a gene for the receptor of the present invention, the antagonist against the receptor of the present invention, and the like can suppress prolactin release and are thus useful as agents for the prevention/treatment of prolactin hypersecretion [e.g., hyperprolactinemia (e.g., sterility, galactorrhea, amenorrhea, atrophy of ovary and uterus, etc.), pituitary tumor, diencephalon tumor, menstrual disorder, etc.), and the like.

Besides, the receptor (e.g., GPR52, etc.) of the present invention or/and its ligands (e.g., reserpine, methoctramine, etc.) are useful for screening the compound or its salts having the preventive/therapeutic action on mental disorders, etc.

The invention claimed is:

1. A method of screening a compound or a salt thereof that changes the binding property of a protein comprising the amino acid sequence represented by SEQ ID NO: 1 or the amino acid sequence having at least about 90% homology to the amino acid sequence represented by SEQ ID NO: 1, or a salt thereof, to a ligand capable of specifically binding to said protein or a salt thereof,
which comprises assaying the binding amounts of said ligand to said protein, or a salt thereof, (a) in the case of contacting said ligand with said protein, or a salt thereof and (b) in the case of contacting said ligand and a test compound with said protein, or a salt thereof, and comparing the binding amounts, wherein a change in binding amounts of said ligand with said protein compared to the binding amounts of said ligand and test compound with said protein indicates that the compound changes the binding property of a protein, the ligand being a reserpine compound, methoctramine compound, or N-[3-(3-chlorophenoxy)phenyl]-2-methyl-8-[3-(1-piperazinyl)propyl]-5, 6, 7, 8-tetrahydro-pyrido[2, 3-d]pyrimidine-5-amine tetrahydrochloride.

2. The screening method according to claim 1, wherein the reserpine compound is a compound represented by the formula:

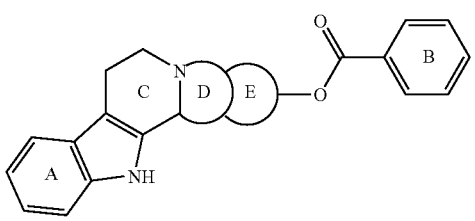

wherein each of Ring A and Ring B is an optionally substituted benzene ring,

Ring C is an optionally substituted 6-membered ring,

Ring D is an optionally substituted 5- to 7-membered nitrogen-containing hetero ring, and, Ring E is an optionally substituted 5- to 7-membered ring; or a salt thereof.

3. The screening method according to claim 1 wherein the ligand is reserpine.

4. The screening method according to claim 1, wherein the methoctramine compound is a compound represented by the formula:

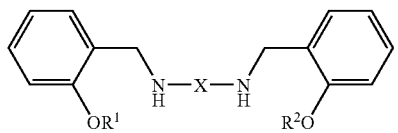

wherein each of $R^1$ and $R^2$ represents an optionally substituted hydrocarbon group and X represents a spacer; or a salt thereof.

5. The screening method according to claim 1, wherein the ligand is methoctramine.

6. The screening method according to claim 1, wherein the amino acid sequence having at least about 90% homology to the amino acid sequence represented by SEQ ID NO: 1 is the amino acid sequence represented by SEQ ID NO: 3 or SEQ ID NO: 5.

7. A method of screening a compound or a salt thereof that changes the binding property of a protein comprising the amino acid sequence represented by SEQ ID NO: 1 or the amino acid sequence having at least about 90% homology to the amino acid sequence represented by SEQ ID NO: 1, or a salt thereof, to a ligand capable of specifically binding to said protein or a salt thereof, which comprises assaying the binding amounts of the ligand to a cell containing said protein, or a salt thereof, or a membrane fraction expressing said protein of the cell, (a) in the case of contacting said ligand with said cell or a membrane fraction expressing said protein of the cell and (b) in the case of contacting said ligand and a test compound with said cell or said membrane fraction, and comparing the binding amounts, wherein a change in the binding amounts of said ligand with said cell, or a membrane fraction expressing said protein of the cell, compared to the binding amounts of said ligand and test compound with said cell, or a membrane fraction expressing said protein of the cell, indicates that the compound changes the binding property of a protein, the ligand being a reserpine compound, methoctramine compound, or N-[3-(3-chlorophenoxy)phenyl]-2-methyl-8-[3-(1-piperazinyl)propyl]-5, 6, 7, 8-tetrahydropyrido[2, 3-d]pyrimidine-5-amine tetrahydrochloride.

8. The screening method according to claim 1, wherein the protein comprising the amino acid sequence represented by SEQ ID NO: 1, or the amino acid sequence having at least about 90% homology to the amino acid sequence represented by SEQ ID NO: 1, or a salt thereof is a protein, or a salt thereof, wherein said protein is expressed on a cell membrane by culturing a transformant containing a DNA encoding said protein, or a salt thereof.

9. The screening method according to claim 1 or 7, wherein the ligand is a labeled ligand.

10. A method of screening a compound or a salt thereof that changes the binding property of a protein comprising the amino acid sequence represented by SEQ ID NO: 1 or the amino acid sequence having at least about 90% homology to the amino acid sequence represented by SEQ ID NO: 1, or a salt thereof, to a ligand capable of specifically binding to said protein or a salt thereof, which comprises assaying cell-stimulating activities mediated by said protein, or a salt thereof, (a) in the case of contacting the ligand with said protein, or a salt thereof and (b) in the case of contacting said ligand and a test compound with said protein, or a salt thereof, and comparing the cell-stimulating activities, wherein a change in the cell stimulating activities mediated by the binding of said ligand with said protein compared to the cell stimulating activities mediated by the binding of said ligand and test compound with said protein indicates that the compound changes the binding property of a protein, the cell-stimulating activities being the activity that promotes or suppresses arachidonic acid release, acetylcholine release, intracellular $Ca^{2+}$ release, intracellular cAMP production, intracellular cAMP production suppression, intracellular cGMP production, inositol phosphate production, change in cell membrane potential, phosphorylation of intracellular proteins, activation of c-fos, pH reduction, GTPγS binding activity, activation of cAMP-dependent protein kinase, activation of cGMP-dependent protein kinase, activation of phospholipid-dependent protein kinase, activation of mitogen-activated protein kinase (MAP kinase), or activities that promote increased expression of serum responsive factor gene; or receptor internalization activity, and the ligand being a reserpine compound, methoctramine compound, or N-[3-(3-chlorophenoxy)phenyl]-2-methyl-8-[3-(1-piperazinyl)propyl]-5, 6, 7, 8-tetrahydropyrido[2, 3-d]pyrimidine-5-amine tetrahydrochloride.

11. A method of screening a compound or a salt thereof that changes the binding property of a protein comprising the amino acid sequence represented by SEQ ID NO: 1 or the amino acid sequence having at least about 90% homology to the amino acid sequence represented by SEQ ID NO: 1, or a salt thereof, to a ligand capable of specifically binding to said protein or a salt thereof, which comprises assaying cell-stimulating activities mediated by said protein, or a salt thereof, (a) in the case of contacting the ligand with a cell containing said protein, or a salt thereof or a membrane fraction expressing said protein of said cell and (b) in the case of contacting said ligand and a test compound with a cell containing said protein, or a salt thereof, or a membrane fraction expressing said protein of said cell, and comparing the cell-stimulating activities, wherein a change in the cell stimulating activities mediated by the binding of said ligand with said protein, or a membrane fraction expressing said protein of said cell, compared to the cell stimulating activities mediated by the binding of said ligand and test compound with said protein, or a membrane fraction expressing said protein of said cell, indicates that the compound changes the binding property of a protein, the cell-stimulating activities being the activity that promotes or suppresses arachidonic acid release, acetylcholine release, intracellular $Ca^{2+}$ release, intracellular cAMP production, intracellular cAMP production suppression, intracellular cGMP production, inositol phosphate production, change in cell membrane potential, phosphorylation of intracellular proteins, activation of c-fos, pH reduction, GTPγS binding activity, activation of cAMP-dependent protein kinase, activation of cGMP-dependent protein kinase, activation of phospholipid-dependent protein kinase, activation of mitogen-activated protein kinase (MAP kinase), or activities that promote increased expression of serum responsive factor gene; or receptor internalization activity, and the ligand being a reserpine compound, methoctramine compound, or N-[3-(3-chlorophenoxy)phenyl]-2-methyl-8-[3-(1-piperazinyl)propyl]-5, 6, 7, 8-tetrahydropyrido[2, 3-d]pyrimidine-5-amine tetrahydrochloride.

12. The screening method according to claim 11, wherein the cell-stimulating activity is a Gs activity.

13. The screening method according to claim 11, wherein the protein comprising the amino acid sequence represented by SEQ ID NO: 1, or the amino acid sequence having at least about 90% homology to the amino acid sequence represented by SEQ ID NO: 1, or a salt thereof is a protein, or a salt thereof, wherein said protein is expressed on a cell membrane expressing said protein by culturing a transformant containing a DNA encoding said protein, or a salt thereof.

14. A method of screening a potential agonist for a protein comprising the amino acid sequence represented by SEQ ID NO: 1, or the amino acid sequence having at least about 90% homology to the amino acid sequence represented by SEQ ID NO: 1, or a salt thereof, which comprises (i) assaying cell-stimulating activities mediated by said protein, or a salt thereof, (a) in the case of contacting a ligand capable of specifically binding to said protein, or a salt thereof with a cell containing said protein, or a salt thereof, and (b) in the case of contacting a test compound with a cell containing said protein, or a salt thereof, and comparing the cell-stimulating activities, or (ii) assaying cell-stimulating activities mediated by said protein, or a salt thereof, in the case of contacting a test compound with a cell containing said protein, or a salt thereof, wherein a change in the cell stimulating activities mediated by the binding of said ligand with said protein, compared to the cell stimulating activities mediated by the binding of said ligand and test compound with said protein, indicates that the compound is a potential agonist, the ligand being a reserpine compound, methoctramine compound, or N-[3-(3-chlorophenoxy)phenyl]-2-methyl-8-[3-(1-piperazinyl)propyl]-5, 6, 7, 8-tetrahydropyrido[2, 3-d]pyrimidine-5-amine tetrahydrochloride, and the cell-stimulating activities being the activity that promotes or suppresses arachidonic acid release, acetylcholine release, intracellular $Ca^{2+}$ release, intracellular cAMP production, intracellular cAMP production suppression, intracellular cGMP production, inositol phosphate production, change in cell membrane potential, phosphorylation of intracellular proteins, activation of c-fos, pH reduction, GTPγS binding activity, activation of cAMP-dependent protein kinase, activation of cGMP-dependent protein kinase, activation of phospholipid-dependent protein kinase, activation of mitogen-activated protein kinase (MAP kinase), or activities that promote increased expression of serum responsive factor gene; or receptor internalization activity.

15. A method of screening a potential antagonist to a protein comprising the amino acid sequence represented by SEQ ID NO: 1, or the amino acid sequence having at least about 90% homology to the amino acid sequence represented by SEQ ID NO: 1, or a salt thereof, which comprises assaying cell-stimulating activities mediated by said protein, or a salt thereof, in the case of contacting a test compound with a cell containing said protein, or a salt thereof, in the presence of a ligand capable of specifically binding to said protein, or a salt thereof, wherein a change in the cell stimulating activities mediated by the binding of said ligand with said protein, compared to the cell stimulating activities mediated by the binding of said ligand and test compound with said protein, indicates that the compound is a potential antagonist, the ligand being a reserpine compound, methoctramine compound, or N-[3-(3-chlorophenoxy)phenyl]-2-methyl-8-[3-(1-piperazinyl)propyl]-5, 6, 7, 8-tetrahydropyrido[2, 3-d]pyrimidine-5-amine tetrahydrochloride, and the cell-stimulating activities being the activity that promotes or suppresses arachidonic acid release, acetylcholine release, intracellular $Ca^{2+}$ release, intracellular cAMP production, intracellular cAMP production suppression, intracellular cGMP production, inositol phosphate production, change in cell membrane potential, phosphorylation of intracellular proteins, activation of c-fos, pH reduction, GTPγS binding activity, activation of cAMP-dependent protein kinase, activation of cGMP-dependent protein kinase, activation of phospholipid-dependent protein kinase, activation of mitogen-activated protein kinase (MAP kinase), or activities that promote increased expression of serum responsive factor gene; or receptor internalization activity.

16. A kit for screening a compound or a salt thereof that changes the binding properties of a protein comprising the amino acid sequence represented by SEQ ID NO: 1, or the amino acid sequence having at least about 90% homology to the amino acid sequence represented by SEQ ID NO: 1, or a salt thereof to a ligand capable of specifically binding to said protein or a salt thereof, which comprises (a) said protein or a salt thereof and (b) said ligand, the ligand being a reserpine compound, methoctramine compound, or N-[3-(3-chlorophenoxy)phenyl]-2-methyl-8-[3-(1-piperazinyl)propyl]-5, 6, 7, 8-tetrahydropyrido[2, 3-d]pyrimidine-5-amine tetrahydrochloride.

17. The screening method according to claim 7, 10, 11, 14 or 15 wherein the reserpine compound is a compound represented by the formula:

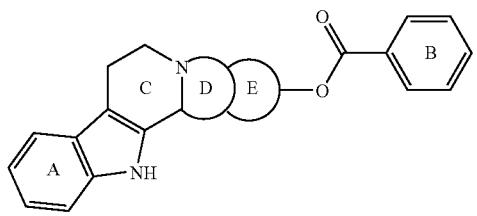

wherein each of Ring A and Ring B is an optionally substituted benzene ring,
Ring C is an optionally substituted 6-membered ring,
Ring D is an optionally substituted 5- to 7-membered nitrogen-containing hetero ring, and,
Ring E is an optionally substituted 5- to 7-membered ring; or a salt thereof.

18. The screening method according to claim 7, 10, 11, 14 or 15, wherein the ligand is reserpine.

19. The screening method according to claim 7, 10, 11, 14 or 15, wherein the methoctramine compound is a compound represented by the formula:

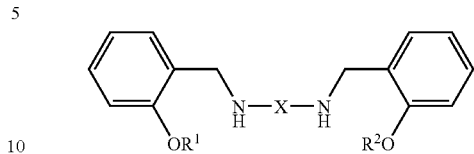

wherein each of $R^1$ and $R^2$ represents an optionally substituted hydrocarbon group and X represents a spacer; or a salt thereof.

20. The screening method according to claim 7, 10, 11, 14 or 15, wherein the ligand is methoctramine.

21. The screening method according to claim 7, 10, 11, 14 or 15, wherein the amino acid sequence having at least about 90% homology to the amino acid sequence represented by SEQ ID NO: 1 is the amino acid sequence represented by SEQ ID NO: 3 or SEQ ID NO: 5.

* * * * *